(12) United States Patent
Neal et al.

(10) Patent No.: US 12,220,170 B2
(45) Date of Patent: Feb. 11, 2025

(54) ABERROMETER WITH A DYNAMICALLY ADJUSTABLE VIDEO FIXATION TARGET

(71) Applicant: Wavefront Dynamics, Inc., Albuquerque, NM (US)

(72) Inventors: Daniel R. Neal, Tijeras, NM (US); James Copland, Albuquerque, NM (US); Xifeng Xiao, Albuquerque, NM (US); Alan Blair, Albuquerque, NM (US); Lyle Kordonowy, Sandia Park, NM (US); Paul Pulaski, Albuquerque, NM (US); Jeff Kolberg, Laguna Beach, CA (US)

(73) Assignee: WaveFront Dynamics, Inc., Albuquerque, NM (US)

( * ) Notice: Subject to any disclaimer, the term of this patent is extended or adjusted under 35 U.S.C. 154(b) by 926 days.

(21) Appl. No.: 17/183,327

(22) Filed: Feb. 23, 2021

(65) Prior Publication Data

US 2021/0263497 A1     Aug. 26, 2021

Related U.S. Application Data

(60) Provisional application No. 62/980,097, filed on Feb. 21, 2020, provisional application No. 62/980,337, filed on Feb. 23, 2020.

(51) Int. Cl.
*A61B 3/10* (2006.01)
*A61B 3/00* (2006.01)
(Continued)

(52) U.S. Cl.
CPC .......... *A61B 3/1015* (2013.01); *A61B 3/0091* (2013.01); *A61B 3/102* (2013.01);
(Continued)

(58) Field of Classification Search
CPC ....... A61B 3/1015; A61B 3/103; A61B 3/107; A61B 3/14; A61B 3/0025; A61B 3/102;
(Continued)

(56) References Cited

U.S. PATENT DOCUMENTS

| 5,777,719 A | 7/1998 | Williams |
| 5,949,521 A | 9/1999 | Williams |

(Continued)

FOREIGN PATENT DOCUMENTS

WO     WO 04072709     12/2004

OTHER PUBLICATIONS

Bullimore "The repeatability of automated and clinician refraction", Optom Vis Sci Aug. 1998.75(8) p. 617-622.
(Continued)

*Primary Examiner* — Brandi N Thomas
(74) *Attorney, Agent, or Firm* — Quinn IP Law

(57) ABSTRACT

This invention relates to methods and devices for designing customized contact lenses, by initially making dynamic wavefront sensor measurements through a trial contact lens that is fitted on an eye, and then calculating a WaveFront Guided (WFG) correction to be applied to the trial contact lens that reduces the RMS level of aberrations as much as practically possible. The output of the wavefront correction program is a customized lathe file that the manufacturer can use to make customized contact lenses on a lathe. The method works best for soft contact lenses and scleral lenses.

38 Claims, 58 Drawing Sheets

(51) Int. Cl.
| | |
|---|---|
| *A61B 3/103* | (2006.01) |
| *A61B 3/107* | (2006.01) |
| *A61B 3/14* | (2006.01) |
| *G01B 11/24* | (2006.01) |
| *G01M 11/02* | (2006.01) |
| *G02C 7/02* | (2006.01) |
| *G02C 7/04* | (2006.01) |
| *G05B 19/4099* | (2006.01) |
| *G06T 7/521* | (2017.01) |
| *G06T 7/55* | (2017.01) |
| *G16H 50/30* | (2018.01) |
| *G16H 50/70* | (2018.01) |
| *B33Y 50/00* | (2015.01) |
| *B33Y 80/00* | (2015.01) |

(52) U.S. Cl.
CPC .............. *A61B 3/103* (2013.01); *A61B 3/107* (2013.01); *A61B 3/14* (2013.01); *G01B 11/24* (2013.01); *G01M 11/0242* (2013.01); *G02C 7/027* (2013.01); *G02C 7/04* (2013.01); *G02C 7/047* (2013.01); *G02C 7/049* (2013.01); *G05B 19/4099* (2013.01); *G06T 7/521* (2017.01); *G06T 7/55* (2017.01); *G16H 50/30* (2018.01); *G16H 50/70* (2018.01); *B33Y 50/00* (2014.12); *B33Y 80/00* (2014.12); *G02C 2202/24* (2013.01); *G05B 2219/35134* (2013.01); *G05B 2219/36199* (2013.01); *G05B 2219/36204* (2013.01); *G05B 2219/49023* (2013.01); *G06T 2207/10028* (2013.01); *G06T 2207/30041* (2013.01)

(58) Field of Classification Search
CPC ......... A61B 3/101; A61B 3/156; A61B 3/158; A61B 2034/102; A61B 3/1005; A61B 3/0091; A61B 3/028; A61B 3/10; A61B 3/112; A61B 3/117; A61B 3/1173; A61B 3/1225; A61B 3/145; A61B 3/152; A61B 3/18; A61B 5/0066; A61F 2009/00872; A61F 2009/0088; A61F 2009/00882; A61F 9/00804; A61F 2009/00848; A61F 2009/00851; A61F 2009/0087; A61F 2009/00887; A61F 9/008; A61F 9/00812; A61F 9/00827
See application file for complete search history.

(56) References Cited

U.S. PATENT DOCUMENTS

| | | | |
|---|---|---|---|
| 6,086,204 | A | 7/2000 | Magnante |
| 6,095,651 | A | 8/2000 | Williams |
| 6,299,311 | B1 | 10/2001 | Williams |
| 6,379,008 | B1 | 4/2002 | Chataeu |
| 6,499,843 | B1 | 12/2002 | Cox |
| 6,511,180 | B2 | 1/2003 | Guirao |
| 6,550,917 | B1 | 4/2003 | Neal |
| 6,554,425 | B1 | 4/2003 | Roffman |
| 6,655,803 | B1 | 12/2003 | Rubenstein |
| 6,830,712 | B1 | 12/2004 | Roffman |
| 7,530,691 | B1 | 5/2009 | Davis |
| 7,967,440 | B1 | 6/2011 | Copland |
| 7,976,163 | B2 | 7/2011 | Campbell |
| 7,980,699 | B2 | 7/2011 | Neal |
| 8,197,064 | B2 | 6/2012 | Copland |
| 8,260,024 | B2 | 9/2012 | Farrer |
| 9,022,570 | B2 | 5/2015 | Applegate |
| 9,486,137 | B2 | 11/2016 | Raymond |
| 9,504,376 | B2 | 11/2016 | Neal |
| 10,201,276 | B2 | 2/2019 | Neal |
| 10,485,417 | B2 | 11/2019 | Copland |
| 10,492,680 | B2 | 12/2019 | Farrer |
| 10,506,923 | B2 * | 12/2019 | Neal ................ G02B 27/286 |
| 10,555,669 | B2 | 2/2020 | Pulaski |
| 10,682,056 | B2 | 6/2020 | Neal |
| 10,849,493 | B2 | 12/2020 | Copland |
| 10,849,495 | B2 | 12/2020 | Pulaski |
| 2018/0104514 | A1 * | 4/2018 | Gertner ................ A61N 7/00 |

OTHER PUBLICATIONS

Perez-Straziota, Randleman, Stulting, "Objective and subjective preoperative refraction techniques for wavefront-optimized and wavefront-guided laser in situ keratomileusis", J Cataract Refract Surg 2009;35:256-259.

Schallhorn—"Wavefront-Guided Photorefractive Keratectomy with a new Hartmann Shack Aberrometer in Patients with Myopia and Compound Myopic Astigmatism," JOPH2015-514837.

Blanton, US "Meta-analysis of six excimer laser platforms for safety and efficacy in myopic laser-assisted in situ keratomileusis," Ophthalmic Review vol. 8, Issue 1 Spring 2015.

Moussa "Visual aberrometric photic patient satisfaction LASIK w high resolution aberrometer," Opth-10-2489.

* cited by examiner

NextWave™ Aberrometer:

Upper Section

NextWave™ Aberrometer:

Middle Section

NextWave™ Aberrometer:

Lower Section

NextWave™ Aberrometer

Motorized Micro Video Display

Wavefront Profile

Wavefront Profile

Wavefront Corrected Contour

Wavefront Corrected Contour

Conventional Contact Lens

WFG Customized Contact Lens (axisymmetric)

Conventional Contact Lens

Conventional Contact Lens

WFG Customized Contact Lens with Non-Axisymmetric Offset

WFG Customized Contact Lens with Non-Axisymmetric Offset

SHC = Serial Host Commands

ABERROMETER WITH A DYNAMICALLY ADJUSTABLE VIDEO FIXATION TARGET

CROSS-REFERENCES TO RELATED APPLICATIONS

This application claims a priority benefit of U.S. Provisional 62/980,097 filed Feb. 21, 2020; and U.S. Provisional 62/980,337 filed Feb. 23, 2020, both of which are incorporated herein by reference in their entirety.

FIELD OF THE INVENTION

The general field of the invention includes ophthalmology and optometry, and methods for designing customized contact lens that includes using wavefront sensors for measuring aberrations of an eye's optics through a contact lens, and methods for correcting these aberrations to improve visual acuity.

BACKGROUND OF THE INVENTION

There are certain corneal conditions (such as keratoconus, pellucid marginal degeneration, and corneal ectasia) that lead to the distortion of the corneal shape. Surgical complications, penetrating keratoplasty, scars, and injury can also lead to undesired distortion. Distortions in the cornea degrade the performance of the optical elements in the eye (cornea and lens). For a normal emmetrope, the cornea and lens work together to collect incident light and create an image on the retina. If one of these elements, namely the cornea, is distorted, then these images are no longer sharp. In fact, a strong distortion can lead to a significant degradation in the overall quality of vision. This can reduce the visual acuity of the subject, affect the contrast sensitivity, create double images, or generally degrade the image quality. The problem with this type of distortion is that it is difficult to correct. These effects are irregular, and as such, are not correctable with the smooth surfaces normally used for correcting vision. So, patients with these distortions cannot be corrected with conventional glasses and contact lenses.

While these conditions are relatively rare, up to 1% of the worldwide population suffers from some condition that includes degraded vision from corneal distortion. Thus, in the US alone there are more than 3 million people that need some enhance form of correction. While there are comprise solutions that provides some level of function, these result in sub-optimal vision.

Corneal crosslinking has recently been approved as a method for stiffening the cornea. This involves the use of UV radiation and Riboflavin to induce crosslinking of corneal fibers. While this technique has been shown to be effective in reducing the progression of corneal ectasia, it does not correct the underlying distortion. It merely freezes it so that it doesn't get any worse.

The wavefront aberrometer has been used effectively to measure the ocular aberrations of the human eye. A small spot of light is projected onto the retina and the scattered light is collected by the lens and cornea and imaged onto a wavefront sensor (Shack-Hartmann, pyramid, interferometer, etc.) [US 5, FIG. 1, 180, U.S. Pat. No. 6,550,917]. The wavefront sensor measures the wavefront of the light to determine optical properties of the eye [U.S. Pat. No. 10,201,276B2, U.S. Pat. No. 6,550,917B1, Ser. No. 06/511, 180, U.S. Pat. No. 6,299,311, Ser. No. 05/777,719]. The measurement can be analyzed in terms of standard orthogonal polynomials, which provides information about the ocular optical system. Wavefront-based refraction has been shown to closely match the refraction measured with subjective methods [Bullimore "The repeatability of automated and clinician refraction", Optom Vis Sci 1998 August 75(8) p 617-622]. The refraction is derived primarily from the low order aberration (LOA) terms while higher order terms (HOA) describe additional aberrations of the eye. These higher-order aberrations can affect vision, as well as the base refraction.

Measured wavefront aberrations have been used as a guide for surgical correction of a patient's vision. Laser Refractive Surgery has developed systems and methods for using the wavefront information to either optimize [Perez-Straziota, Randleman, Stulting, "Objective and subjective preoperative refraction techniques for wavefront-optimized and wavefront-guided laser in situ keratomileusis", J Cataract Refract Surg 2009; 35:256-259] or directly guide the surgery [U.S. Pat. Nos. 5,949,521, 6,095,651]. Specialty instruments have been developed that incorporate both wavefront aberrometry and corneal topography in a single instrument, which allows for co-aligned measurement of the total aberrations and anterior cornea along a single (and known) fixation axis. This provides information needed for guiding the surgery and for planning a laser treatment that incorporates known reflection and beam footprint calibrations [Schallhorn—"Wavefront-Guided Photorefractive Keratectomy with a new Hartmann Shack Aberrometer in Patients with Myopia and Compound Myopic Astigmatism," JOPH2015-514837]. The wavefront guided treatment methodology has been shown to be effective at producing excellent patient outcomes for laser refractive surgery [Blanton, US "Meta-analysis of six excimer laser platforms for safety and efficacy in myopic laser-assisted in situ keratomileusis," Ophthalmic Review Volume 8, Issue 1 Spring 2015; Moussa "Visual aberrometric photic patient satisfaction LASIK w high resolution aberrometer," Opth-10-2489].

The wavefront guided approach has also been applied to other treatment modalities [U.S. Pat. Nos. 5,777,719, 6,086, 204] including contact lenses [U.S. Pat. Nos. 6,499,843, 6,554,425, 6,830,712, WO 04072709A], with some success. However, these techniques have not been used in wide clinical practice, partially due to the stability of the contact lens on the eye. This is difficult to overcome because the comfort of the contact lens depends to some extent on the fact that it moves on the eye, spreading the tear film and providing oxygen to the cornea.

For keratoconus, there are localized regions in the cornea (and hence across the pupil) that have significantly different power. 10-15D changes in power over 2-3 mm are not uncommon. Thus, any correction must maintain its position over the same structure size. There are contact lens technologies that do not move appreciably. The use of a rigid material (usually a Rigid Gas Permeable lens) that rests on the sclera can provide a stable lens. These are usually much larger than the iris and are called scleral lenses. These are often used for these cases with irregular cornea because, to some extent, the tear film between the lens and the cornea fills in some of the irregularity. However, this is only a partial correction in most cases. While many patients find these an acceptable solution, they are very expensive and may require up to 10 visits to the doctor to get a good fit. Since they are so much bigger, they are difficult to put in and remove, often requiring a special tool with a suction cup. And, since they are much thicker in profile, they require some adjustment on the part of the patient, who must slowly adapt by wearing them a few more minutes each day. In addition, they can fill with proteins that make vision cloudy or uncomfortable. While it is possible to use a wavefront customization of a scleral lens (U.S. Pat. No. 9,554,889), this only adds complexity to an already complex system, requiring potentially even more Eye Care Practitioners (ECP) visits.

Soft contacts, by contrast, are used by 90% of those using contact lenses for vision correction. They are generally quite comfortable and require little adaptation. Most patients that use soft contacts for vision correction have no sensation of wear and can wear them for up to 16 hours/day. The lenses themselves are made from Edifilcon™, silica hydrogel, or other porous material, so they transmit water and are oxygen permeable. Since soft contacts are in such common use, the fitting process is well understood, and is very commonplace among ECPs.

While various approaches have been proposed for using a wavefront-guided customization on contact lenses [U.S. Pat. Nos. 6,086,204, 6,095,651, 6,379,008, 6,499,843, U.S. Ser. No. 06/511,180, U.S. Pat. Nos. 6,554,425, 6,655,803B1, 7,530,691, 9,022,570, 9,658,470B2, and WO 04072709], in general these attempts have not enjoyed much success. Certainly, there has not been a successful commercialization of any of these techniques. This is primarily due to the instability of the contact lens, or the inability to get an accurate measurement of the contact lens' position and rotation on the eye. The workflow for the patient and ECP requires many iterative attempts and may not result in a successful conclusion. Part of the problem is that the equipment did not provide feedback on the lens stability at the time of fitting.

Thus, a key part of the process for making a customize contact lens, particularly for a keratoconic eye that has large aberrations, is an instrument that can make accurate, repeatable measurement with a simple workflow. This instrument can have several different workflows:

1. Bare eye measurement for fitting. The instrument should be able to measure the eye with no correction to determine basic parameters of the eye, provide information for fitting contact lenses, and provide an accurate refraction.
2. Over-refraction with trial lens. The instrument should be capable of recording sequences of measurements and images for determining the physical stability of candidate contact lenses and simultaneously determining the appropriate correction.
3. Aberrations. The instrument should be capable of measuring aberrations dynamically to evaluate effectiveness of the candidate correction.
4. Data integration. The instrument should integrate functions such as Electronic Medical Records (EMR) connectivity, order processing, data review, and diagnostics.
5. The instrument should minimize human/machine interactions to obtain accurate refraction.

SUMMARY

This invention relates to improved methods and devices for designing customized contact lenses, by providing an instrument that is optimized for making the appropriate measurements. The instrument can be used to determine fitting parameters for a contact lens, measuring lens stability, and then making dynamic wavefront sensor measurements through a trial contact lens that is fitted on an eye. This data is then used to calculate a WaveFront Guided (WFG) correction to be applied to the contact lens that reduces the RMS level of aberrations as much as practically possible. The output of the wavefront correction program is a customized lathe file that the manufacturer can use to make customized contact lenses on a lathe. The method works best for soft contact lenses and scleral lenses. Finally, the instrument can be used to evaluate the performance of the contact lens both objectively and subjectively.

DETAILED DESCRIPTION OF THE INVENTION

Figure 1:
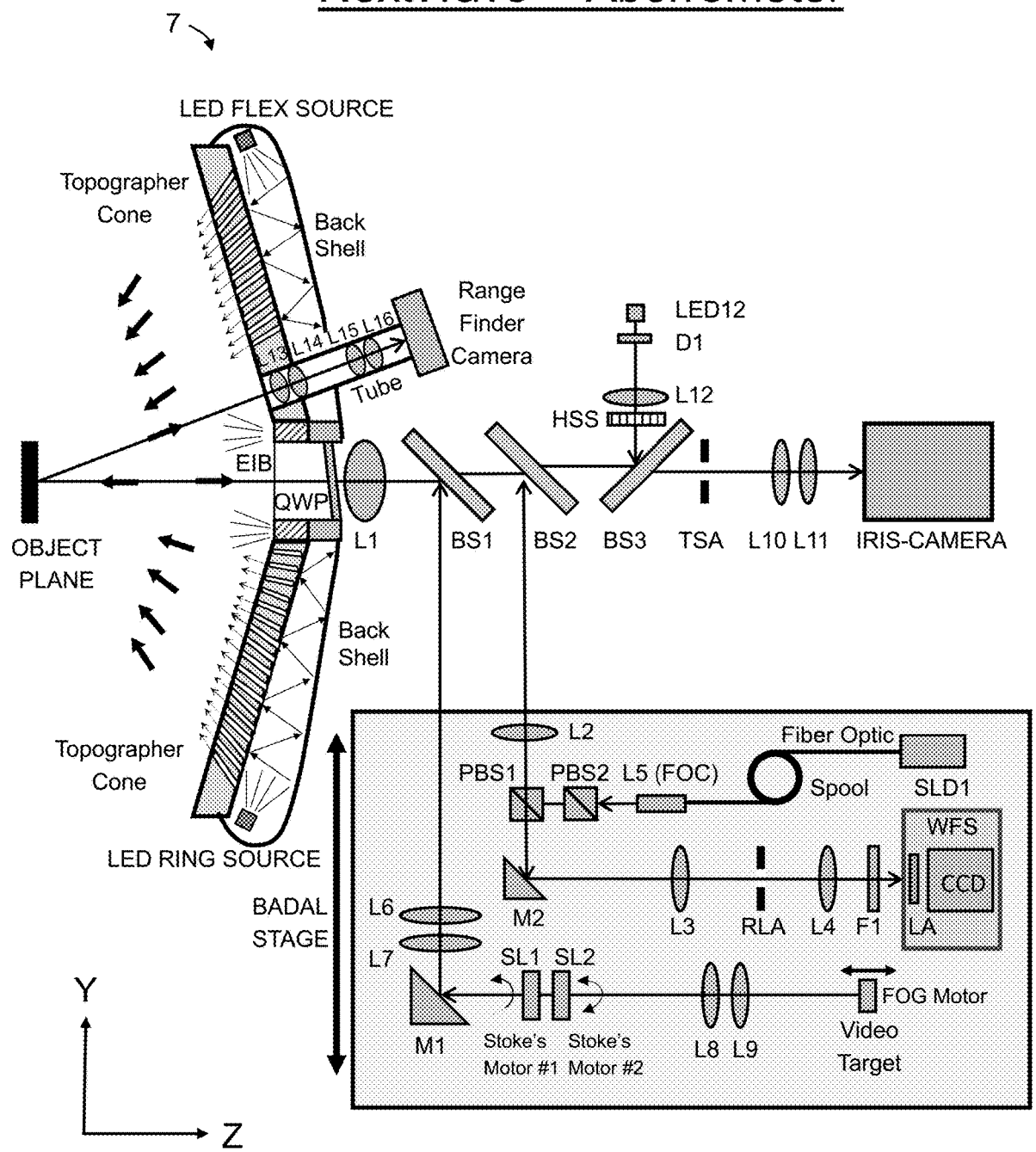
FIG. 1 shows a schematic optical layout of a first embodiment of an improved aberrometer, NextWave™, that is optimized for making measurements of eyes that are fitted with a contact lens, according to the present invention.

The following acronyms are used herein: WF=WaveFront; WFD=WaveFront Dynamics, LLC; WFG=Wavefront Guided; WFE=Wavefront Error; WFS=WaveFront Sensor; LOA=Lower Order Aberration, HOA=Higher Order Aberration, RMS=Root Mean Square; CL=Contact Lens; CCL=Customized Contact Lens; SCA=Sphere, Cylinder, and Axis; Pt=patient, SLD=Super Luminescent Diode, Seq=Spherical Equivalent; BS=BeamSplitter; RLA=Range Limiting Aperture; OD=right eye; OS=left eye; DTF=Dynamic Tear Film, HORMS=Higher Order RMS, ECPs=Eye Care Practitioners; OCT=Ocular Coherence Tomography. All references cited herein are incorporated by reference in their entirety.

The words "accommodate" and "accommodative" both refer to the condition where the eye automatically adjusts the shape of its natural crystalline lens to re-focus the eye when the gaze target distance changes. Typically, "accommodation" results in an increase in optical power and a reduction in pupil size; whereas "non-accommodation" results in a decrease in optical power and an increase in pupil size. The words "sequential" and "sequence" refers to a dynamic, time-dependent set or series of measurements. increase in optical power (accommodation) and a reduction in pupil size. The phrase "alignment camera" and "Eye Imaging Camera" mean the same thing. The word "aberrometer" is an optical instrument that is broadly construed to include both refractometer and autorefractor systems. The HOA's can be described by Zernike polynomials, or a wavefront error surface. Note: the phrase "conventional contact lens" refers to a contact lens that is un-corrected with respect to higher-order aberrations (HOA's). A conventional contact lens corrects for low order aberrations (defocus and astigmatism) but not higher order aberrations (i.e., HOAs are un-corrected when using a conventional contact lens). The phrase "secondary optics group" and "Badal stage" refer to the same configuration of optical components.

Wavefront Measurement Instrument:

In order to measure the wavefront aberrations of the eye with sufficient accuracy and dynamic range, a high-dynamic range aberrometer system must be designed. Wavefront aberrations can be measured with a Hartmann-Shack sensor, scanning deflectometer, pyramid sensor, sciascopy, or other methods. However, to measure a keratoconus eye, sufficient resolution must be achieved to detect and characterize the large variations in power from one region to another. Note that the optical power of the eye can vary from the superior pupil to the inferior pupil (3 mm) by more than 10D for a subject with strong keratoconus. This creates challenges for some types of instrumentation. However, with modern high resolution, high speed cameras, it is possible to design systems with sufficient accuracy and dynamic range to measure most eyes. For a Hartmann-Shack sensor, the techniques of U.S. Pat. No. 6,550,917 (which is incorporated herein by reference) can be effectively applied, using a Range Limiting Aperture (RLA) to limit crosstalk between lenslet channels in the wavefront sensor.

In order to sample the optics of the eye, a small spot of light is projected onto the retina by a probe beam. This can be a laser, SLD, LED, or other low intensity light source. Advantageously, a fiber-coupled, infrared SLD can be used to provide a good quality beam that can be imaged onto the retina. The use of a fiber-coupling component provides opportunities to splice multiple fibers with different sources at different wavelengths. This will provide additional information useful for multifocal optics.

One of the key limitations of objective instruments for measuring the eye is the human/machine interaction. Placing a large instrument close to the patient's face can cause something called instrument accommodation. In this condition the patient accommodates to focus on a near object. The measurement device has an internal fixation target that is intended to provide a stable line-of-sight reference, and to encourage the patient to focus at a desired plane. However, aberrations degrade the appearance of this target, and can lead to errors in the fixation location. For a subject with large astigmatism, there are two focal planes that are apparent to the subject, one for each of the astigmatic meridians. These may appear to be separated in space by a significant apparent distance. To the patient, this manifests as lines at different orientations that appear to focus at different planes. If the patient fixates on the wrong one due to accommodation, the measurement accuracy will be degraded, even if the instrument perfectly measures the eye.

Figure 18:
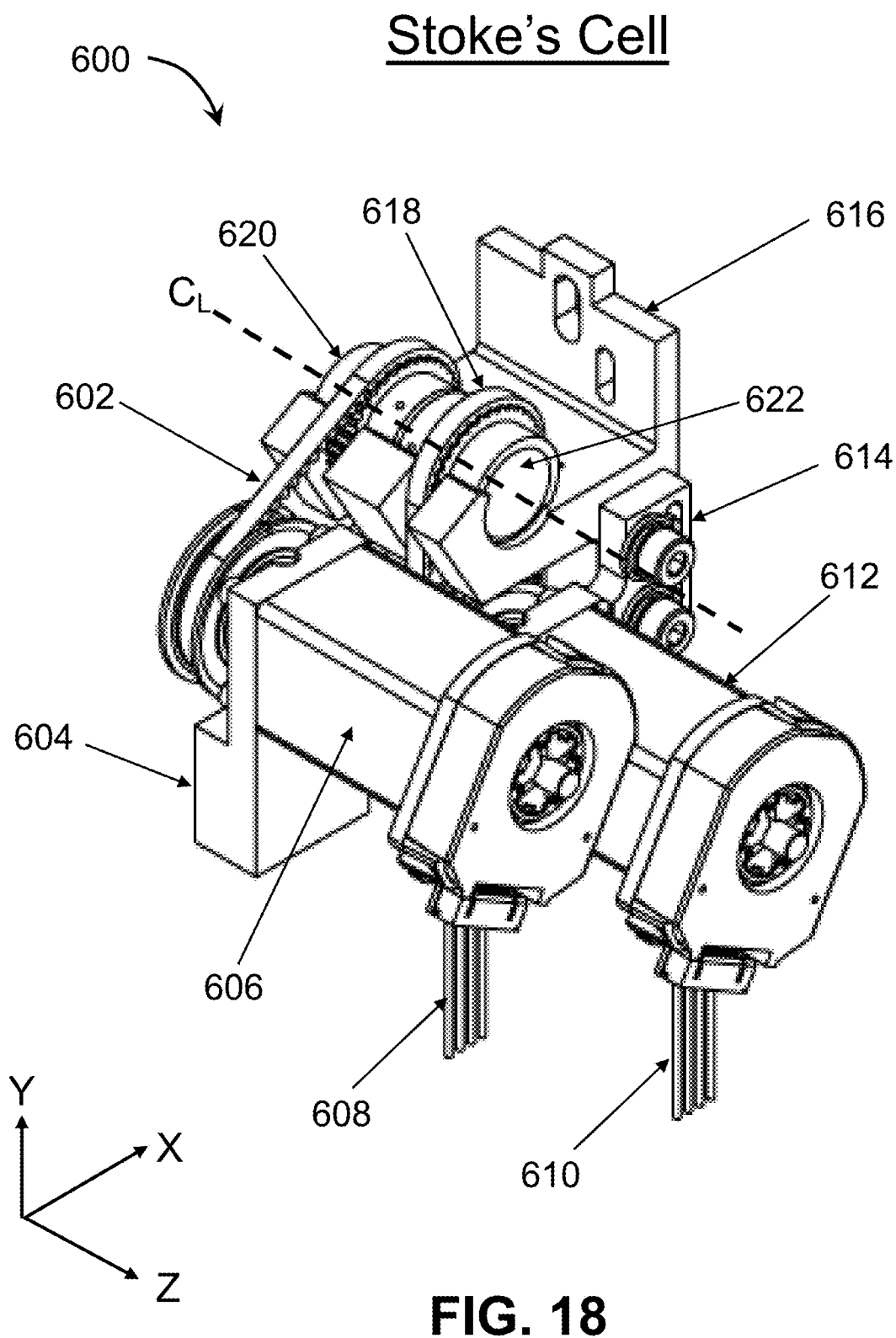
FIG. 18 shows a perspective view of a paired Stoke's lenses, according to the present invention.

Thus, it is necessary to provide a fixation target that properly conditions the eye for the appropriate measurement. This can be done by compensating the target for the patient's astigmatism with a variable optical system. FIG. 18 shows an astigmatic optical system (Astigmatic Compensation System (ACS)), also called a Stoke's cell 600, which consists of two cylindrical lenses (620 and 622) of opposite and equal power, for example a +4D cylinder lens and a −4D cylinder lens, placed closed together and arranged so that they can rotate independently under control of motors. Preferably stepper motors with encoders (608 and 610) are used to monitor the exact position and ensure proper calibration and repeatability. When the lenses are arranged along the same meridian, the + power and the − power cancel out, and the net optical power is zero. However, when the optical axis of one relative to the other is adjusted by 90 degrees, the powers add, and so the effective lens has double the power of each independent lens. By adjusting the relative angle, a continuously-variable power of any programmable amount can be achieved. Once the desired angle between lenses has been set, the pair can be rotated together as a single unit to adjust the axis of the effective lens. Thus, the astigmatism and astigmatic axis can be adjusted and controlled with relatively simple optics.

FIG. 18 shows an example of such a configuration, including the stepper motors (606 and 612), encoders (608 and 610), optics (620 and 622), and structure (604, 614, 616). In this embodiment, the lenses are rotated using belts to drive the rotation, however, many other arrangements are possible, including direct drive, gear driven, etc. that would be apparent to one skilled in the art. In further embodiments, alternative methods of generating an astigmatic wavefront could be used. These alternative methods include, but are not limited to, deformable mirrors (e.g., MEMS mirror) and liquid crystal lenses. The deformable MEMS mirror generates a defined wavefront by changing the shape of the mirror surface so that light reflected from the mirror will have the desired wavefront. The liquid crystal lens uses liquid crystal molecules which align in response to applied electric fields. The phase of light transmitted through the liquid crystal is changed to produce the desired wavefront.

Figure 5:
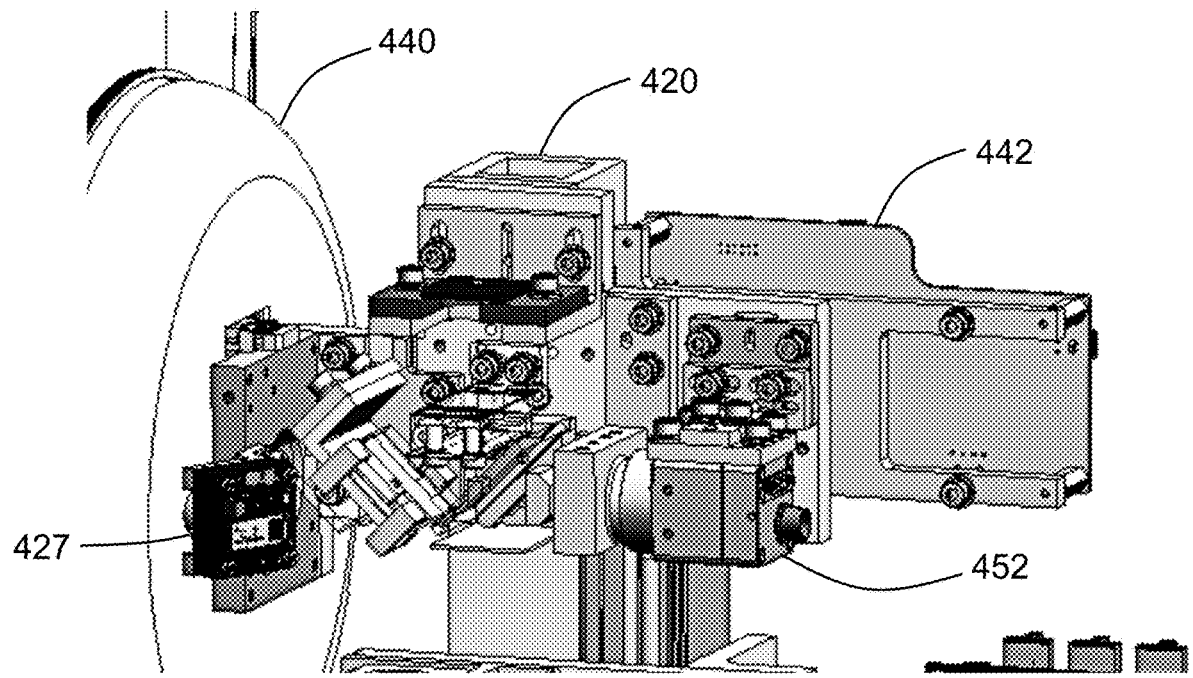
FIG. 5 shows a perspective elevation view of an example of upper internal components and movable stages of a NextWave™ aberrometer, according to the present invention.
Figure 5:
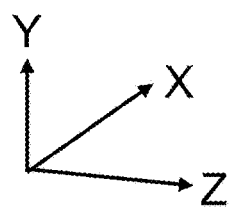

During the measurement process, a signal can be derived to feed the astigmatism compensation system. This can be derived from the wavefront sensor itself. When the eye is first placed in front of the instrument, the wavefront sensor begins to make measurements. Usually, there is also a period of autorefraction where the Badal stage's position is adjusted to match the optical system power to the eye's spherical equivalent ($S_{eq}$). As shown in FIG. 1, during this process, the wavefront sensor makes a sequence of measurements of the eye, while continuously adjusting the Badal stage's position. The Badal Stage has a secondary group of optics and components that are fixed relative to each other (FIG. 6), but move together relative to the primary optics (FIG. 5). Once a sufficient accuracy measurement can be obtained (which completes the Sphere measurement, S), the astigmatism and axis values can also be determined from the wavefront measurement. These values are then used to drive the Astigmatic Compensation System (item 600 on FIG. 6) to the desired position. As these elements move, the target will slowly come into better focus and the differences in apparent position between the astigmatic meridians will be reduced. This process usually takes a few seconds.

In addition to compensating for astigmatism, the focus of the target must be controlled. If the target is arranged so that the fixation target appears virtually at a finite distance, then the patient will focus on this target, and the instrument will measure the refraction needed for the patient to achieve good focus at this distance. It is often desired to measure the "distance refraction" or the "infinite refraction". For this the target must be imaged at infinity, or arranged to stimulate the patient to attempt to dis-accommodate. This can be accomplished, for example, by "fogging" the target. To this end, a small amount of hyperopic defocus is used to create a target that is slightly out of focus ("fogged") in the hyperopic direction. As the patient cannot adjust his accommodation system to image past infinity, this helps assure that the far-point of the refraction is measured. This same goal is accomplished during a typical manifest refraction, where the patient provides subjective feedback. In this case, the ECP will add about 2 Diopters of "plus", while adjusting the sphere with a phoropter, to make sure that the patient is not accommodating.

For a measurement instrument, this should be as simple and automatic as possible. To this end, the fixation target (502 on FIG. 17) is placed on a small electromechanical stage (504 on FIG. 17) that can be controlled using an actuator. The position of the target relative to an imaging pair of lenses, L8+L9, determines the vergence, or focus position of the target. This is also called "fogging" since by adjusting the target vergence, a similar "fogging" process that that used in the subjective method can be achieved. This is monitored using an encoder (510 on FIG. 17). Initially, this stage is adjusted to provide a constant offset (1.5-2D) between the Badal optical system and the fixation target so that the autorefraction process converges. This fixation target fogging or vergence control mechanism provides a continuous adjustment of the apparent target position. The target itself is preferably, a micro-video-display 502 that can be programmed with different targets and illumination levels. This feature can also be used to measure the accommodative range of a patient. The vergence is adjusted in steps while the patient is being measured. The accommodation range is the range over which the patient was able to adequately track the fixation target using their accommodating mechanism.

The fixation target itself is preferably, a micro-video-display 502 that can be programmed with different targets and illumination levels. This can be used to project eye charts, individual letters, geometric patterns, and scene targets. It is even possible to project short movie loops or GIFs. This feature can also be used through motor 508 to measure the accommodative range of a patient. The target vergence is adjusted in steps while the patient is being measured. The accommodation range is the range over which the patient was able to adequately track the fixation target using their natural accommodating mechanism.

Figure 48A:
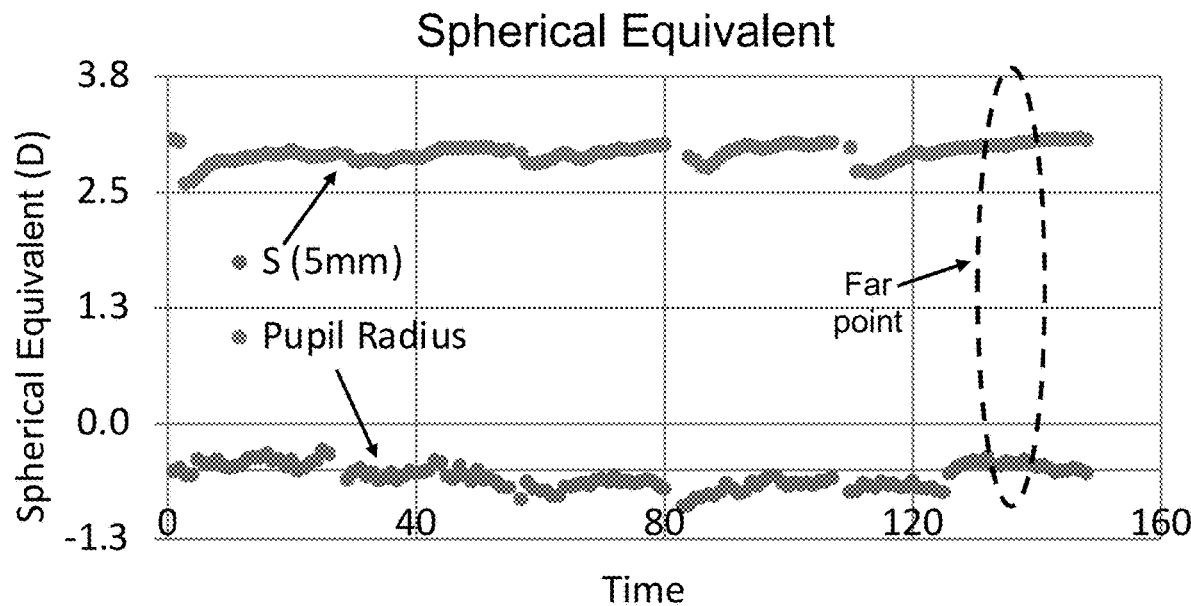
FIG. 48A shows a dynamic measurement of the spherical equivalent and the pupil's radius of a patient's eye, according to the present invention.
Figure 48B:
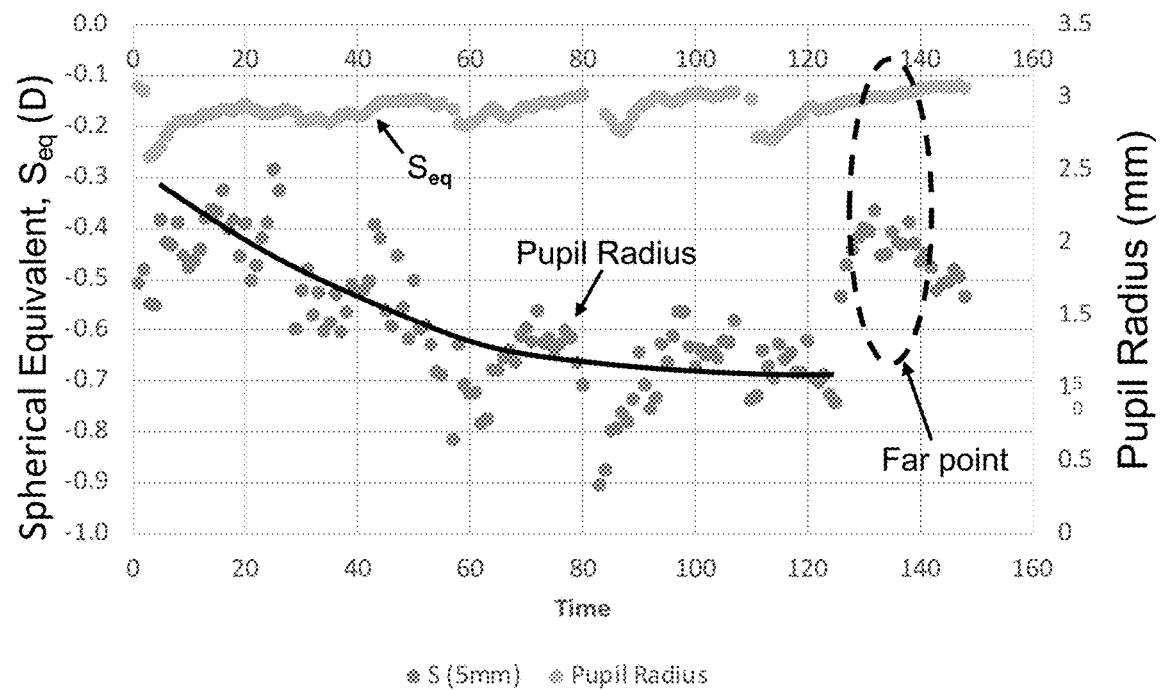
FIG. 48B shows a dynamic measurement of the spherical equivalent and the pupil's radius of a patient's eye, according to the present invention.

The final cue for making an accurate refraction measurement is the time-dependent dynamics of the process. The eye is constantly moving and adjusting itself. As the patient looks at a target, their accommodative muscles constantly adjust by small amounts, essentially searching for the best focus (as shown in FIGS. 48A and 48B). But the eye may only focus on the far-point for a short period time. The ciliary body that controls the accommodation mechanism of the eye is also attached to the iris. So, when an accommodative effort is induced, the ciliary body contracts and causes both an increase in optical power (i.e., accommodation) and a reduction in pupil size. This fact can be used to analyze a sequence of measurements to determine the optimum refraction. The "far-point" is the point at which the measured spherical equivalent has highest (most positive) value, and the pupil size is maximum. This can be readily determined using the present invention because it is designed to capture a sequence of measurements over a period of time.

It should be noted that the fixation target controls are Sphere (S), Cylinder (C) and Axis. This is exactly the same as are present in a conventional phoropter instrument, except that in this case these are able to control the fixation target continuously (where a typical phoropter is limited to 0.25D steps). These are controls for the components shown on FIG. 17. FIG. 18 shows the opto-mechanical components for controlling the Stoke's cell lenses SL1 and SL2; and the position of the target FOG motor 508 in FIGS. 1 and 17. Thus, once the patient has been measured with the instrument, adjustments of the SCA controls would lead to variations in the target appearance. This provides a mechanism for subjective refinement. Controls are provided on either the software Graphical Use Interface or directly as electronic input. The operator or the patient can adjust these controls to optimize optical presentation of the image projected on the micro-display. Reading the position of the cylinders in the Stoke's cell, and of position of fogging (or vergence control) lenses (L8+L9) in FIG. 1 from the encoders provides a means of confirming the objective measurement. This method might be particularly useful for those that have strong higher order aberrations but are unable to wear customized lenses. In this case it might be desirable for the patient to select the combination of SCA that gives them the best vision. This may not be the same as the objective refraction calculated from the wavefront.

One key element for a practical instrument to be useful in the clinical for fitting and designing contact lenses is the alignment of the instrument to the patient's eye. Typical ophthalmic instruments mount the instrument on some type of stage. A slit-lamp base is very common and appears in most commercial instruments. While this is common and understood by most users, it has several disadvantages. With a mechanical stage, the alignment itself is accomplished by a skilled operator who controls X, Y and Z positions using a Patient Alignment Stage (PAS) to optimize alignment and focus. It is the skill of the operator that determines the consistency of the alignment. These can lead to an operator dependence on the measurement quality. Also, given that we are interested in acquisition of dynamic information or sequence, potentially lasting 20-40 seconds, there is often a need to continuously monitor and adjust the alignment of the system. For this present invention, we have conceived incorporation of an auto-alignment system to overcome the disadvantages of purely manual alignment.

Figure 3:
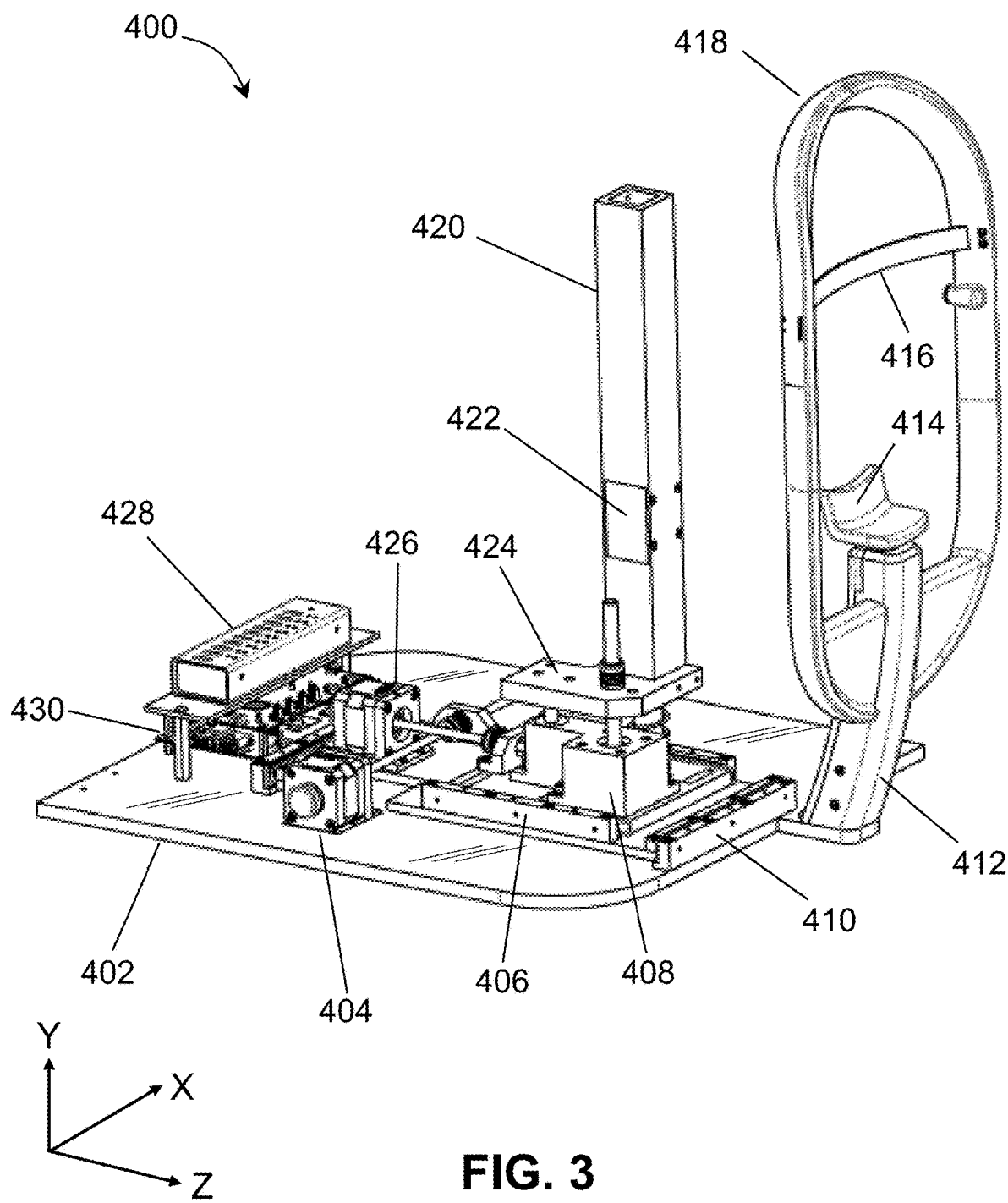
FIG. 3 shows a perspective view of an example of an internal support structure and movable stages of a NextWave™ aberrometer, according to the present invention.

To this end, the improved aberrometer mounts on a Patient Alignment Stage (PAS) platform that is movable in three orthogonal directions (X, Y, and Z) as shown in FIG. 3. The patient is arranged to sit at 90° from the operator. This facilitates the interaction between operator and patient and allows the operator to hold up an eyelid and observe the alignment process. Each motion is controlled by a stepper motor 404, 426, and 408, and has encoders to monitor the position. The encoders can be used in a "closed loop" control system to linearize and smooth out the response to position commands. These positions may be controlled either manually with a joystick input, or automatically. The encoder positions provide positioning for various test and fixture elements of the stage; and in particular, there are two positions that are pre-determined:

1) Park position. At a certain X-Z position (horizontal plane) a park position is identified that has a pin attached to the Y-stage and an associated set of holes for the X-Z stages. Positioning the X-Z to this location and then lowering the Y-stage inserts the pin into the hole, thereby locking any motion of the X-Z stages. This park position is effective for minimizing instrument damage during shipment and/or movement.

2) Test eye position. A test eye or model eye (415 in FIG. 11) with a simulated cornea, iris, and retina is built into the side of the chin rest frame 418. This test eye has known optical properties and can be measured with the instrument simply by positioning the stage at the appropriate location. This provides for daily verification that the instrument is functioning properly within specification. It can also be used for service and manufacturing operations to calibrate the instrument (either at the manufacturer site or in the field) should components need to be replaced.

In order to take full advantage of the motorized patient alignment stage, a feedback mechanism for determining the position of the cornea relative to the instrument is needed. XY position can be determined fairly readily using the built-in iris camera or WFS, as shown in FIG. 1. There are several features that can be examined in the image, such as the pupil, the retro-reflected pupil from the WFS, or various Purkinje reflections. The Z position is somewhat more difficult to determine. It very common to use focus and some type of optimization algorithm to find the best focus, usually of the iris. However, this suffers from several difficulties. The iris is imaged through the cornea (which may be distorted), and so may not be the correct object plane to use as the instrument reference. But the biggest problem is that when the eye is a long way out of focus (i.e., when the patient first puts an eye in front of the instrument), then it is difficult to tell which way to initially move the Z-stage to make it better. It would be desirable to have an automated means to determine the best Z-position across the full range of travel of the electro-mechanical stages.

Figure 4:
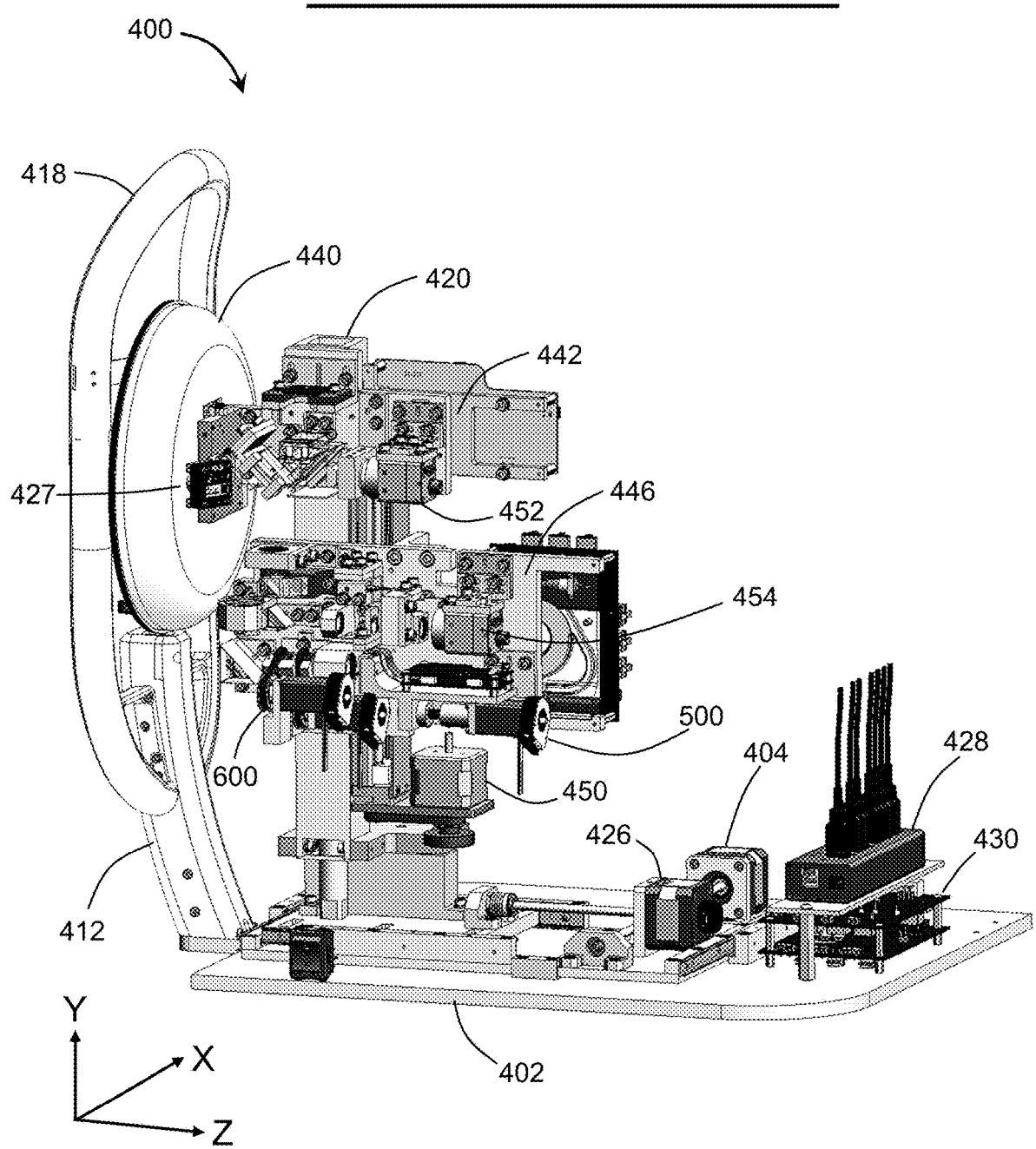
FIG. 4 shows a perspective elevation view of an example of internal components and movable stages of a NextWave™ aberrometer, according to the present invention.

This can be readily accomplished with a second imaging camera (e.g., the Range Finder Camera as shown in FIG. 1), arranged to create an image of the cornea region at a small off-axis angle (also shown as item 427 in FIG. 4 and FIG. 5). This camera can look at the same features and provide feedback in the form of an error signal to the control system for the stage. But, the advantage is that the signal will monotonically increase with Z-position. Consider the position with the instrument at its farthest position from the eye. Assume for the moment that the X-Y position is centered, and only Z is mispositioned. In this case the rangefinder camera will report an image that is off to the left. As the stage moves to bring the eye closer to the desired object plane, the image moves closer to the center. The desired location is a position that has been pre-determined in manufacturing as the correct optical object plane. This is not necessarily exactly centered on any camera, but may include offsets to compensate for minor fabrication irregularities. If the system continues to move closer to the eye then the rangefinder camera will report an image that is off to the right. Thus, the signal changes monotonically in Z. For this type of system, the X, Y and Z control loops can be implemented independently, as there is little cross-coupling between the three signals.

Figure 51:
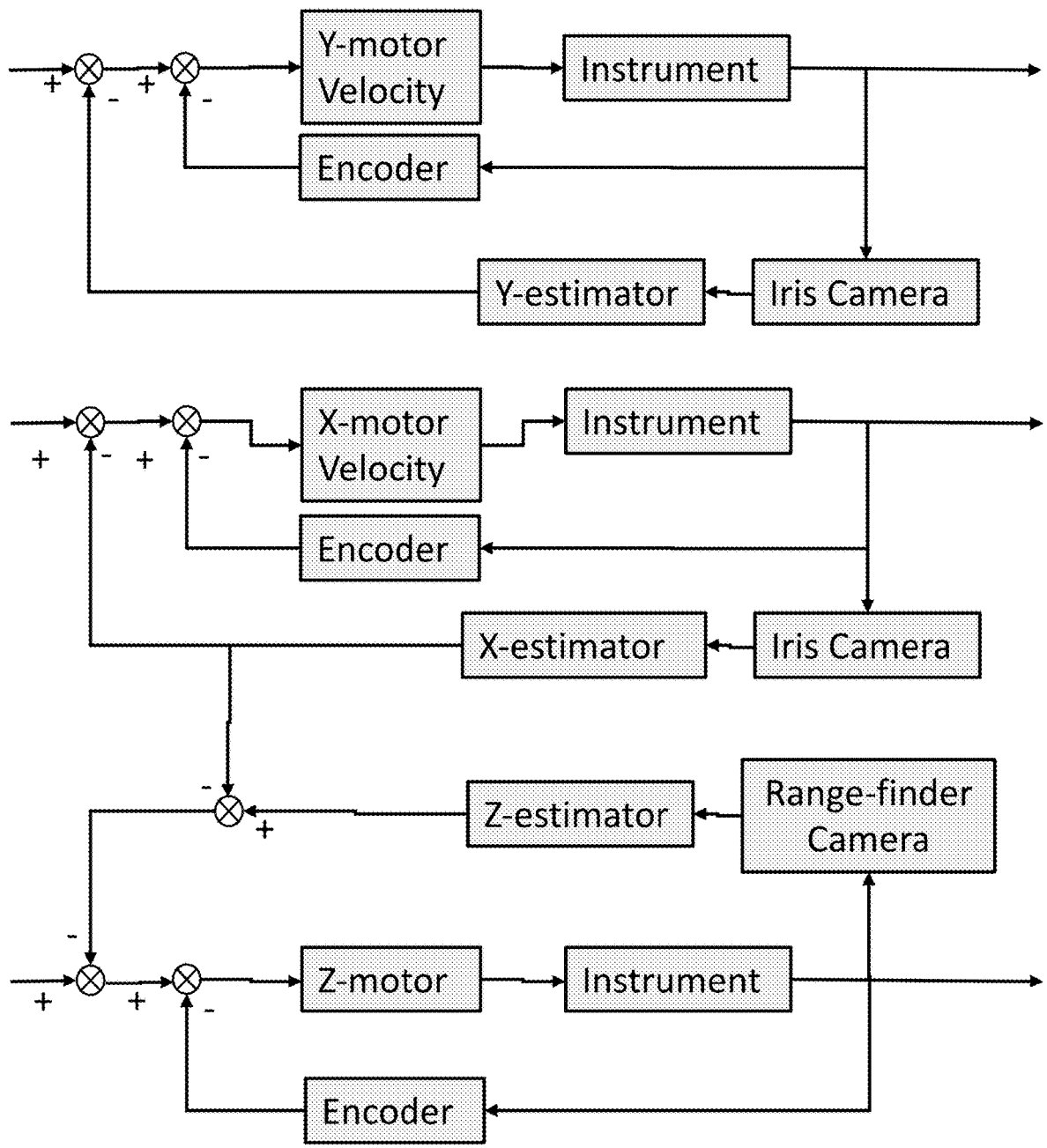
FIG. 51 shows a first schematic example of a control system block diagram for automatically positioning the instrument relative to the eye, according to the present invention.

FIG. 51 shows a block diagram of an example of a patient-to-instrument alignment control system. The X, Y, and Z motors are fixed to the Instrument's rigid frame, which also contains the iris camera and rangefinder cameras. So, a motion of the X, Y or Z motors results in a movement of the whole instrument and cameras. As the instrument is moved relative to the eye, the cameras detect a shift in the eye. The system includes an estimator program that converts the camera signal to a XY position. This can be done by image processing and may include analysis of the image to find the pupil, Purkinje reflection, or other object(s) of interest. It may be advantageous to capture the $1^{st}$ Purkinje images from the illumination LEDs, as these are usually very bright. When the alignment process is just beginning, these images may be significantly out of focus. However, the control system will continuously update the estimates while the stage moves, using the digital control system, and as the alignment gets closer to the desired location, the images will come into sharp focus. The control system may be designed to drive the velocity of the various motors in response to an error signal, or directly determine a position.

There is a cross-coupling between the X-position (as measured by the Iris Camera) and the Rangefinder Image X-position. As the instrument moves in Z, the range finder camera estimator would show an X-direction shift. To compensate, the X-position from the Iris Camera can be subtracted from the signal that drives the Z-motor. This is shown as the cross-connection between Z and X channels in FIG. 51. The control system functions as a classic digital linear control system, with sampling and filters as needed to damp vibration and minimize noise. Typically, the sample bandwidth (frame rate) is 10 times the closed loop bandwidth. For the purposes of eye tracking and maintaining eye alignment during the measurement, it is not necessary (or desirable) to track fast eye movement or saccades. Rather the system needs to correct for long term drift and decentration while recording long sequences (20-40 seconds). This requires about 2-3 Hz closed loop bandwidth, which in turn implies a 20-30 Hz sample rate. This is consistent with typical camera frame rate of 30 fps.

Figure 52A:
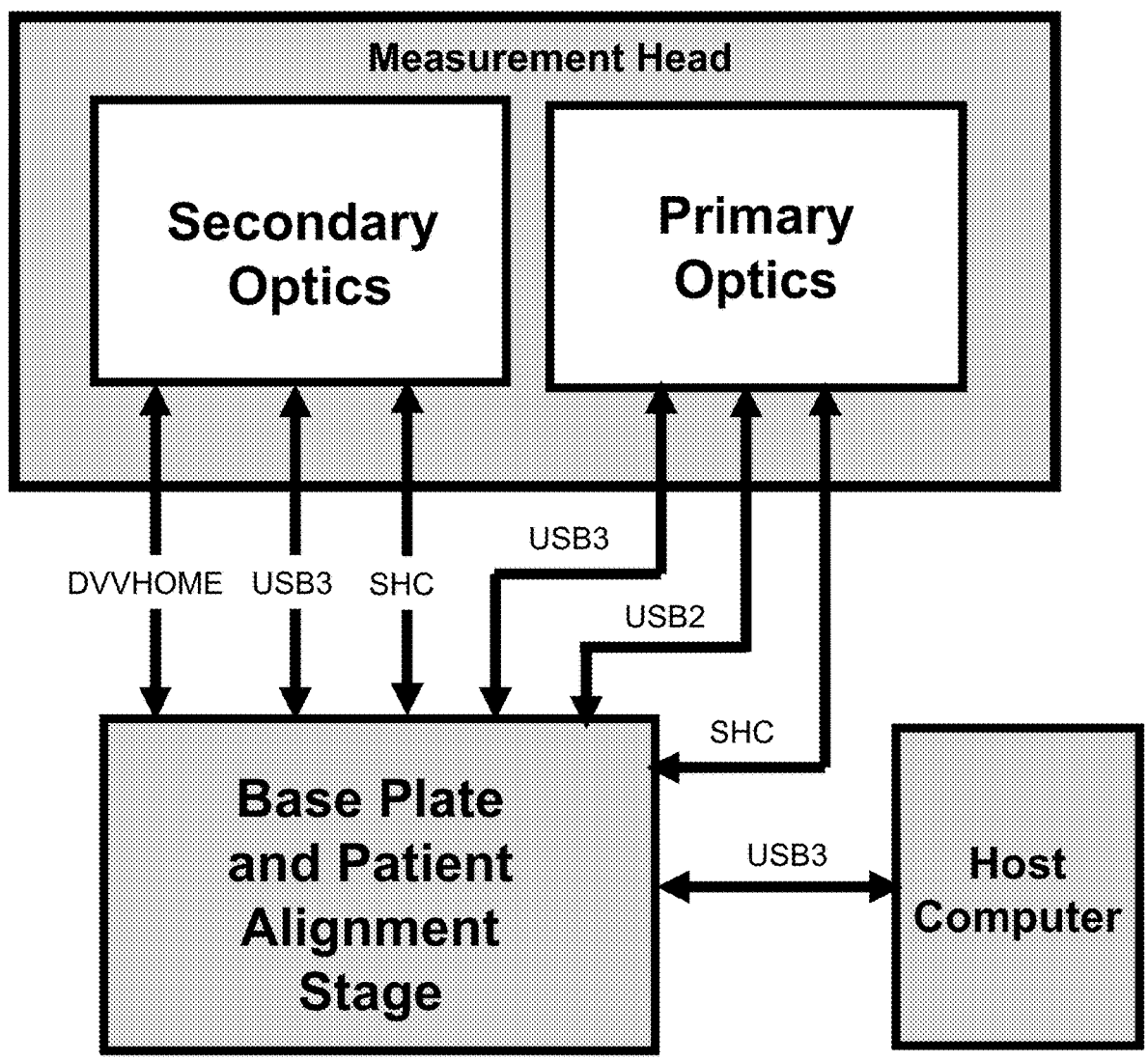
FIG. 52A shows a first schematic example of a control system block diagram for the Aberrometer Hardware Architecture, according to the present invention.
Figure 52B:
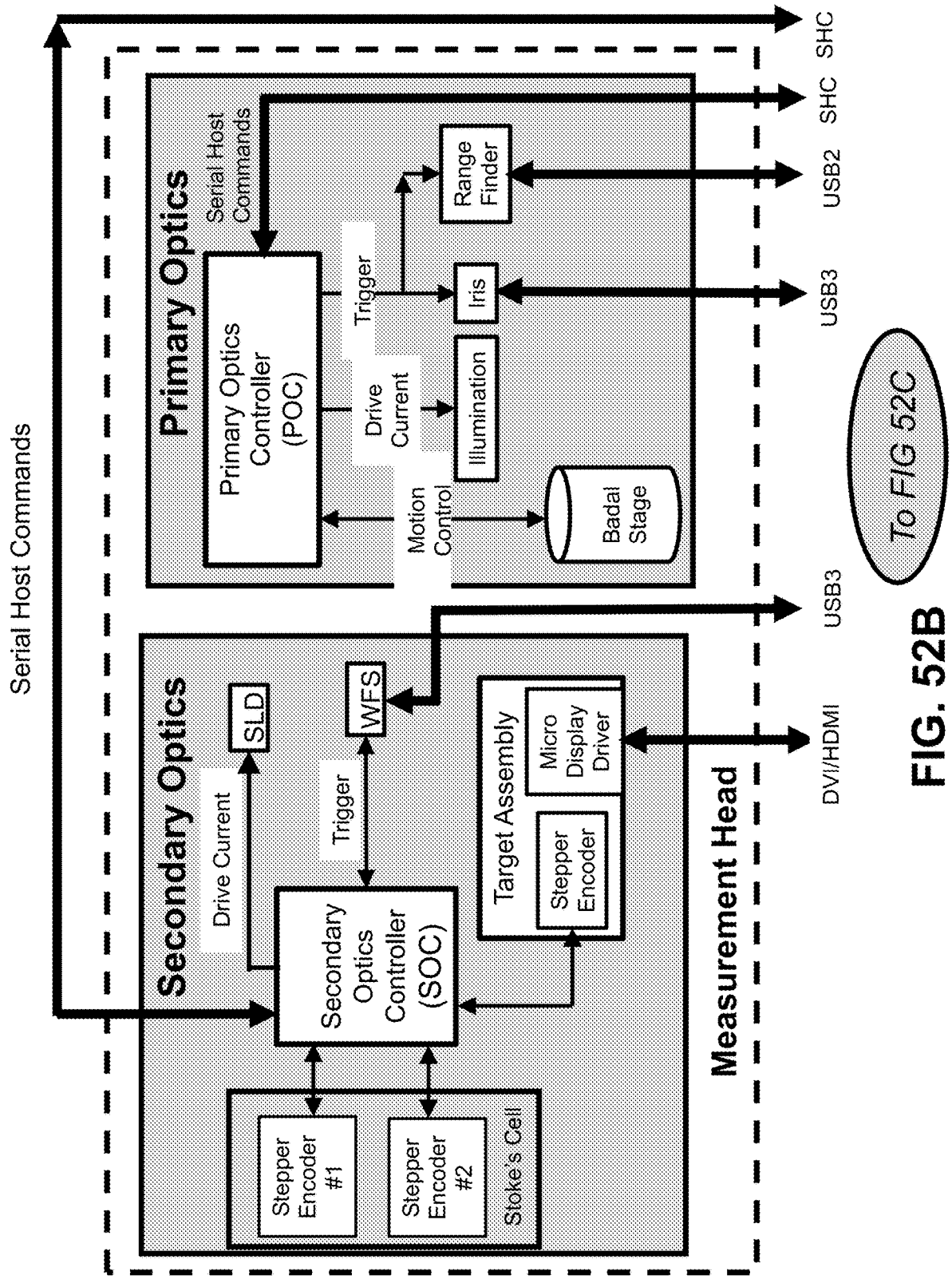
FIG. 52B shows a first schematic example of a control system block diagram for the Aberrometer Hardware Architecture, according to the present invention.
Figure 52C:
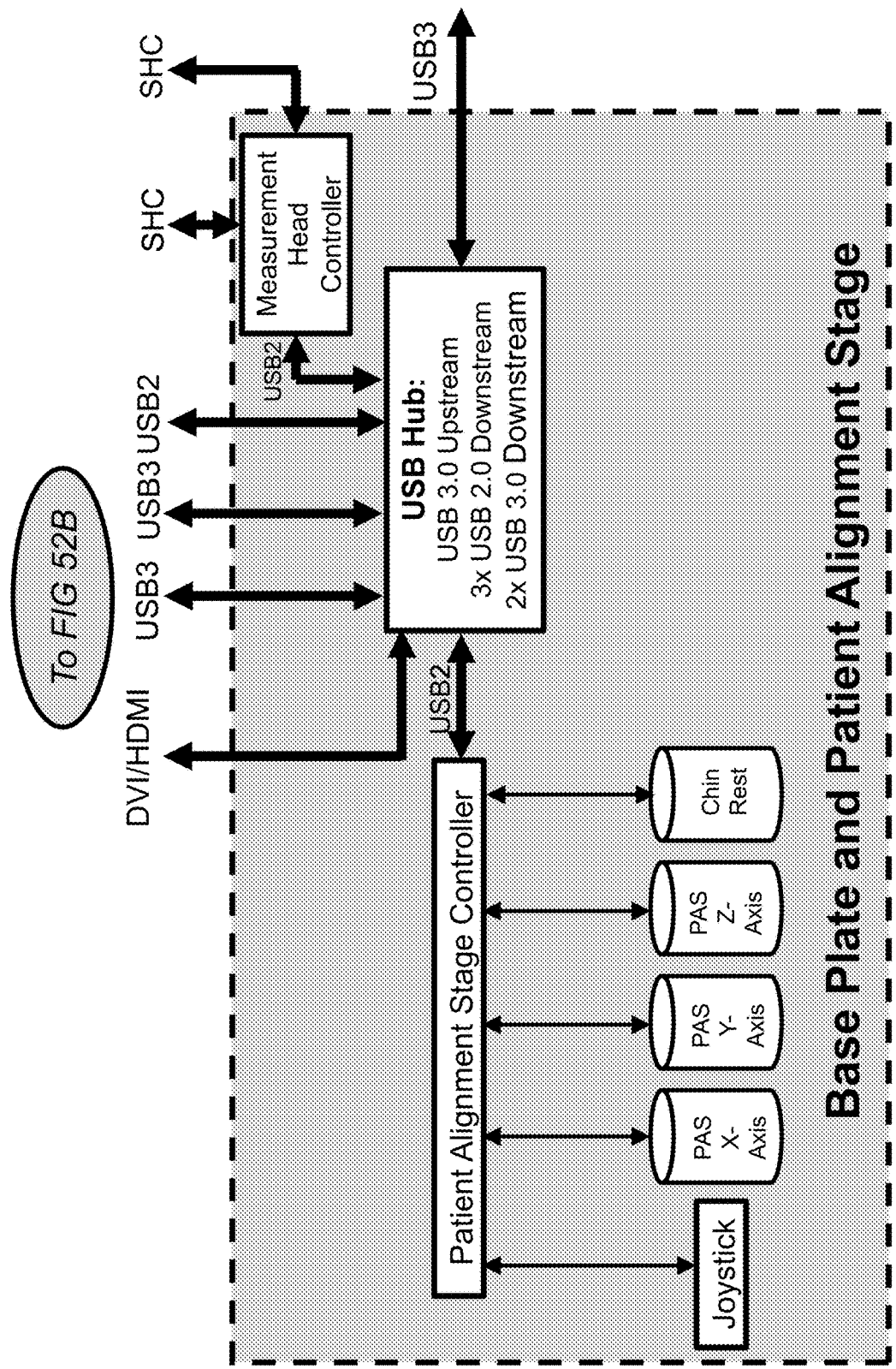
FIG. 52C shows a first schematic example of a control system block diagram for the Aberrometer Hardware Architecture, according to the present invention.

FIG. 52A, B, C shows a first schematic example of a control system block diagram for the Aberrometer Hardware Architecture, according to the present invention. This architecture controls the patient alignment stage, the cameras, light sources, Badal stage, Stoke's cell, and visual target fogging system. It connects to an external computer that provide for data storage and user interaction.

Alternative methods of determining the best Z-position could also be used. These include, but are not limited to, determining Z-position from far off-axis light sources, determining Z-position from the difference in focus or image shift of multiple light sources at different distances from the cornea (either on-axis or off-axis), high resolution time of flight sensors, and chromatic confocal sensors.

Ocular Surface Measurement:

One of the important workflows is the fitting of the contact lens itself. A base contact lens is specified with several key parameters. These include central curvatures (k1, k2, k2 axis), horizontal visible iris diameter (HVID), and refraction (Sphere, Cylinder, Axis). Thus, it would be useful if the instrument could determine these parameters in an objective manner, with a straightforward workflow. The wavefront aberrometer data can be used to calculate SCA, and the iris image can be analyzed to produce the HVID. However, measurement of corneal curvatures would benefit from having corneal topography or keratometry data. In fact, since subjects with corneal ectasia or keratoconus can have significantly distorted corneas, more detailed information could be used in designing the back surface of the contact lens. While k-values are sufficient as a starting point for the base curve, other parameters may be better for fitting these patients. Several different parameters can be calculated from the corneal topography. These include: asphericity (corneal Q-value), Pupil Averaged Corneal Power, Sim-k (simulated keratometer values), central-k (curvature at corneal vertex), max-k (maximum value of the curvature), max-k location (x,y position of the maximum curvature), IS difference (inferior-superior difference in curvature), mid-peripheral curvature, and simulated contact lens fit. Thus, it is highly advantageous to have accurate corneal topography measurements. Corneal topography can be measured in many different ways, including placido projection, Schiemflug imaging, OCT imaging, and 3D fluorescein imaging. Several potential embodiments for the present invention can be used.

Placido Topography:

A placido topographer projects a series of rings onto the cornea and then collects an image of the pattern of lights on a camera. By analyzing the pattern, the curvature and irregularity of the cornea can be determined. Placido topographers measure the radial gradient of the surface, since only the radial position of the ring relative to the corneal vertex can be determined. The orthogonal (azimuthal) gradient can be inferred from changes in the radial gradient in the azimuthal direction, but it is not measured directly. This implies an essential ambiguity in placido topographers, that azimuthal variations are not measured directly. This causes measurement errors for those surfaces that have rapid variations in the azimuthal direction, such as post-surgical Radial Keratotomy.

Spot Based Topography:

The spot-based approach solves the azimuthal sensitivity problem because each spot can be analyzed to determine both x and y position shift. This gives the surface gradients in both x and y directions. This information can then be integrated to provide the correct surface shape with no ambiguity.

Another issue with integrating a high dynamic range topographer with a wavefront aberrometer is the competing requirements for the size of the main objective lens. To have a wide field of view image and collect highly deviated rays, it is advantageous to have a large objective. However, this would lead to a lot of missing data right in the middle of the topographer image. One solution to this problem is to use a beamsplitter (BS3 in FIG. 1) to project a pattern onto the central cornea and that fills in the missing regions. This allows for a large lens (L1 in FIG. 1) to be used with no gaps in the data.

Corneal topographers suffer from an issue called the scale ambiguity. That is a flatter object that is further away looks the same as a steeper object that is much closer. So, topographers need a way to break this symmetry and/or measure the distance to the eye. In the prior art, this has been done by creating illumination structures that are at different distances from the eye or by analyzing the central, projected regions separately from the cone images. However, in the preferred embodiment that includes a motorized XYZ stage and an accurate means for estimating the Z position through triangulation from two cameras, this object can be achieved much more directly and accurately.

Figure 19:
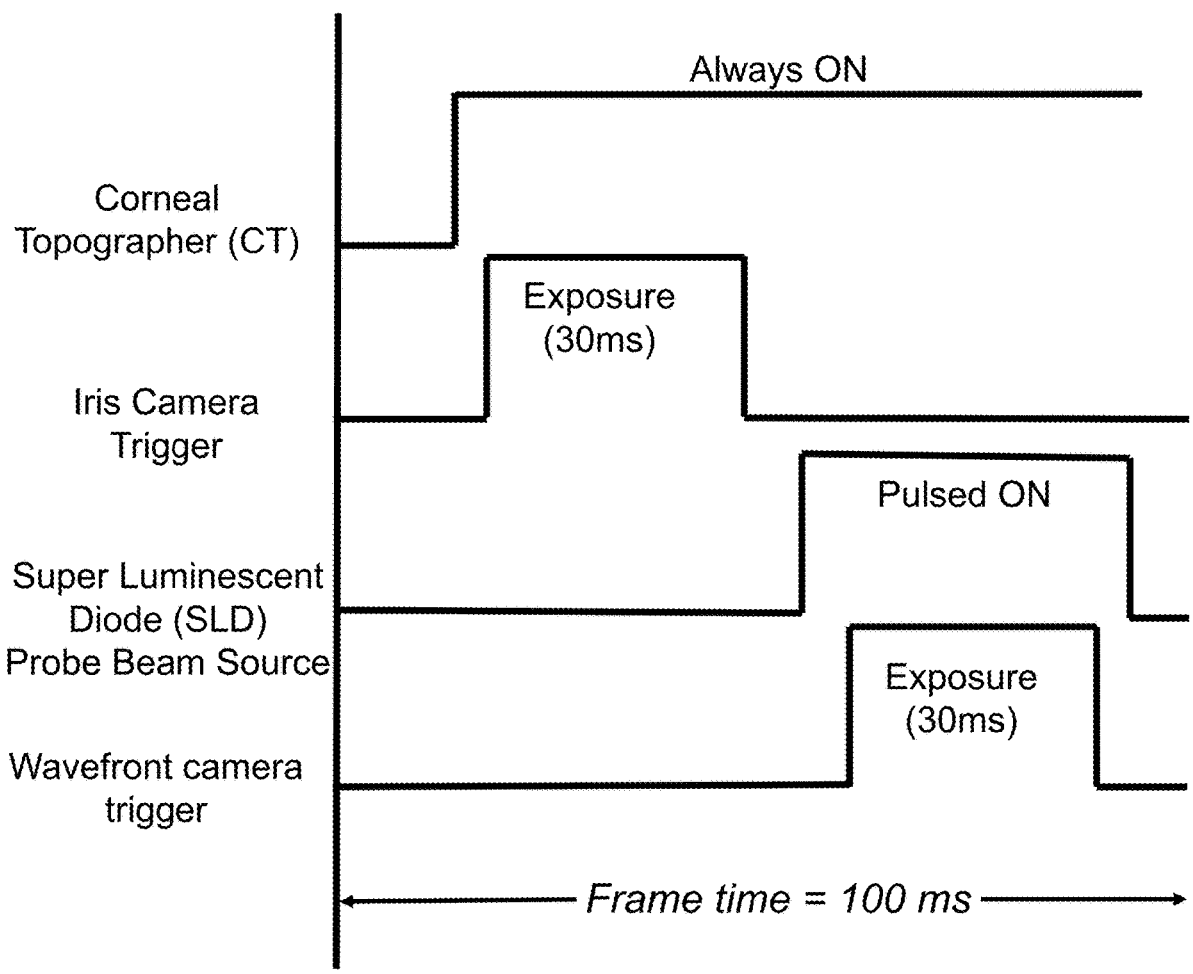
FIG. 19 shows a graph illustrating a first example of timing sequences of key components of a NextWave™ aberrometer for a single frame time=100 ms.

One key element for fitting contact lenses is an imaging system for aligning and focusing on the eye and for collecting images of the eye, both with and without contact lenses. It is important for this system to have a large field of view so that the edges of various contact lenses can be observed. Furthermore, illumination must be provided that highlights fiducials or other marks on the contact lenses used for determining centering and alignment. It is advantageous to provide electronics to control the imaging camera and illumination. This can readily be done by synchronizing LED illumination circuits with a global shutter camera using a micro-controller, as shown in FIG. 19. These electronics will also facilitate the use of multiplexing to make several different, interleaved measurements in the same sequence. The iris image, wavefront images, and even corneal topography images can be acquired by rapidly switching between illumination and various cameras. Iris images and corneal topography use the same imaging camera, but with different illumination states. To this end, it is advantageously arranged so that the illuminations states are stored in firmware where they can be rapidly changed from one state to another.

FIG. 1 shows a schematic optical layout of a first embodiment of an improved aberrometer instrument, according to the present invention. FIG. 1 depicts an arrangement for an improved aberrometer system that can be used advantageously to measure a keratoconic eye. This instrument, called NextWave™, comprises seven different optical paths:

1. an Iris Imaging path;
2. a Corneal Topographer (CT) path;
3. a Helmholtz source path;
4. a Probe Beam path;
5. a Wavefront Sensor path;
6. a Visual Target path; and
7. a Range Finder Camera path;

The Iris Imaging path goes through QWP, L1, BS1, BS2, BS3, TSA, L10, L11 and into the Iris Camera. Light for the Iris Camera path comes from the eye illumination board (EIB). The Corneal Topographer path starts with a perforated cone that has a pattern of many holes (e.g., 800 non-parallel, conically-oriented holes) in the Topographer Cone that emit light after being illuminated by light from a LED Flex Ring located behind the topographer cone. Then, this illumination light reflects off the cornea and passes through to the Iris Camera via QWP, L1, BS1, BS2, BS3, TSA, L10, and L11. The Helmholtz Source path starts with light from LED12 going through diffuser D12, then Lens12, and then through the Helmholtz Source HHS (a plate with parallel holes in it), reflects off BS3 through BS2, BS1, L1, QWP, reflects off the cornea, and then light reverses and goes back through QWP, L1, BS1, BS2, BS3, TSA, L10, L11 and on to the Iris Camera. The Probe Beam path starts at the super luminescent laser diode (SLD), goes through a fiber optic cable (coiled in a spool for mechanical convenience) through a Fiber Optic Collimator (L5), goes through PBS2, reflects off PBS1, goes through L2, reflects off BS2, goes through BS1, L1, QWP and then through the cornea, forming a spot of light on the retina. Some of that light scatters off the retina, leaves the eye, and then goes back into the instrument along the Wavefront Sensor path (as described next).

Continuing on with respect to FIG. 1, the Wavefront Sensor path goes through QWP, L1, BS1 reflects off BS2, through L2, PBS1, reflects off M2, through L3, RLA, L4, F1 (Filter 1) and onto the wavefront sensor WFS. Light going into the Wavefront Sensor path comes from the Probe Beam (described above). The Visual Target Path goes through QWP, L1, reflects off BS1, goes through L6, L7, reflects off M1, goes through Stokes Lens1, Stokes Lens2, L8, L9 then reaches the video target (VT). The Range Finder Camera path goes through L13, L14, L15 and L16 and then onto the Range Finder Camera. The lenses are contained in a small tube that fits through the Topographer cone. The LED FLEX RING's purpose is to illuminate backside of the topographer cone. A backside baffle (back shell) contains the light emitted by the LED FLEX RING. The topographer cone has a plurality of numerically-controlled (NC) machined holes (e.g., 800 holes) that all point, in a conical fashion, towards a central point (i.e., the eye at the object plane), which collimates light originating from backside LED strip lights (similar to a Helmholtz light source (HHS)) towards the object plane. The light sources can all be infrared sources, or a mixture of visible and infrared sources.

The eye is measured with an optical instrument that delivers a probe beam into the eye. The instrument performs pairs of interleaved iris visual imaging and wavefront sensor measurements, taken in rapid, alternating succession at a speed that is faster than the changes of the accommodation of the eye, for example within 100-200 milliseconds. The eye would generally not need to be cyclopleged (i.e., paralyzed or applanated) for the measurement, so the eye can be measured in conditions that are the natural conditions.

Accommodative responses are often thought of as being slow, but there are also accommodative tremors that are small and occur at rates that require fast cameras to see, for instance, at a rate of 60 hertz. Some reports have indicated unusual patterns of accommodative eye tremors in eyes suffering from myopia progression, particularly in response to changes in visual inputs such as following targets or switching gaze angles.

Figure 2:
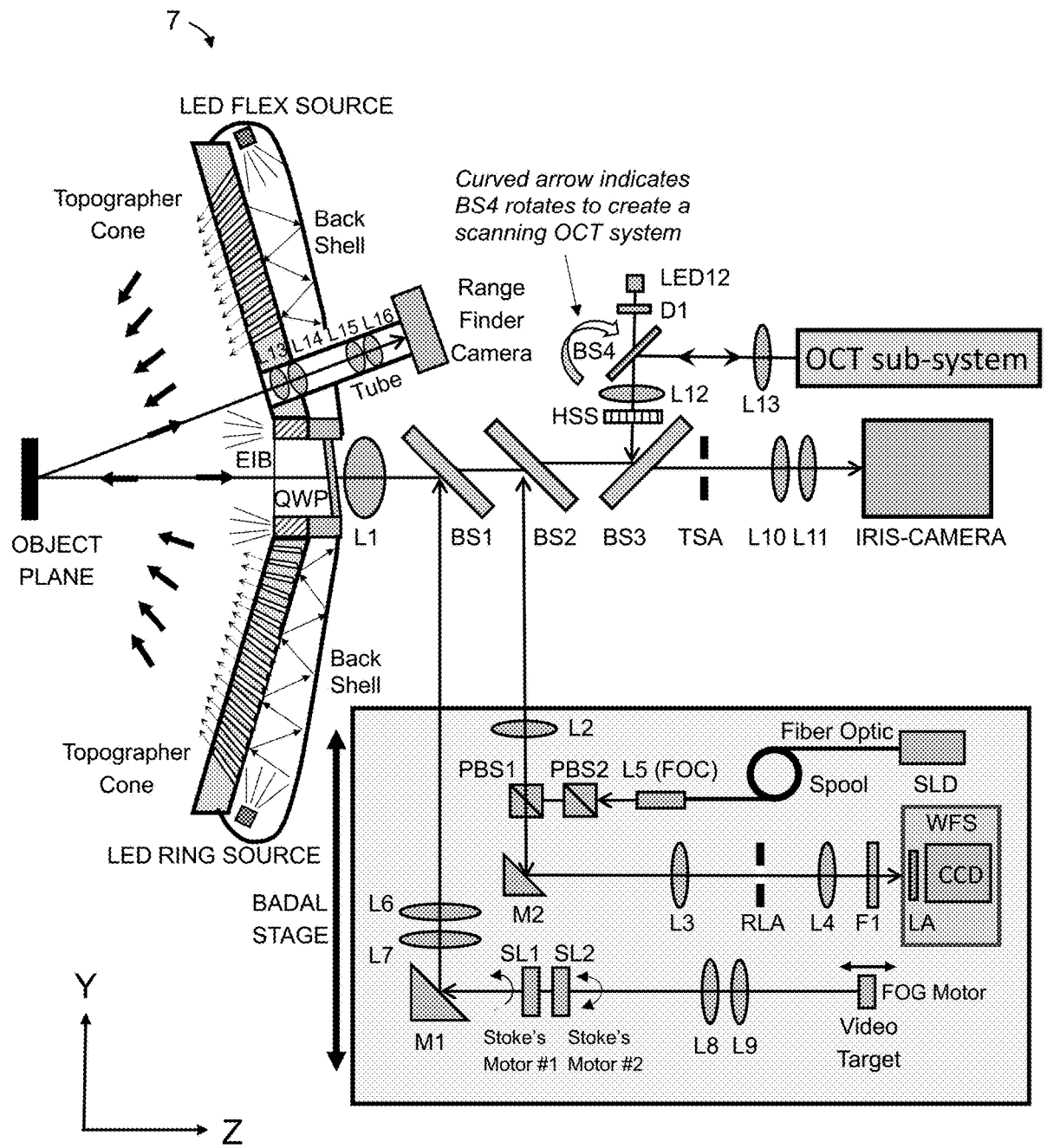
FIG. 2 shows a schematic optical layout of a second embodiment of an improved aberrometer, NextWave™, plus an OCT sub-system, which is optimized for making measurements of eyes fitted with a contact lens, according to the present invention.

FIG. 2 shows a schematic optical layout of a second embodiment of an improved aberrometer, NextWave™, plus a scanning Ocular Coherence Tomography (OCT) subsystem, which is optimized for making measurements of eyes fitted with a contact lens, according to the present invention. The OCT sub-system generates a beam of light that reflects off of a rotatable (scanning) fourth beamsplitter, BS4, which redirects the light down through a twelfth lens, L12, then through Helmholtz plate, HHS, and onto the third beamsplitter, BS3, which redirects the light through a second beamsplitter, BS2, then through the first beamsplitter, BS1, and through first lens, L1, and quarter wave plate, QWP, and then onto the eye. Reflections from the eye reverse direction and then pass through the QWP, L1, BS1, BS2, reflect off BS3, goes through the HHS, L1, reflect off BS4 and then go back into the optical fiber of the OCT sub-system. The OCT subsystem contains an interferometric detector that measures distance from the detector to surfaces in the eye that scatter light. Scanning beamsplitter, BS4, generates OCT probe beams that are incident on the eye at off-axis angles (which are continuously variable angles of incidence, depending on the rotation angle of the scanning beamsplitter BS4).

In the configuration shown in FIG. 2, the Helmholtz LED and the OCT system use different wavelengths, so it is possible to coat a glass plate such that the Helmholtz plate is transparent across its entire surface to the light from the OCT system, but is opaque to the light from the LED where the coating is present, so a pattern of back lit holes is presented to the optical system at the wavelength of the Helmholtz LED. Similar optical function can be achieved by other arrangement of beam splitters, lenses and aperture plates that are obvious to those skilled in optical engineering.

As discussed previously, it is advantageous for contact lens fitting to provide information about the shape of the cornea. Since many contact lenses extend beyond the cornea and rest partially on the sclera, it would be useful to also obtain measurements of the shape of the sclera as well. An OCT system can be configured to measure both the cornea and anterior segment, as well as part of the sclera. This information could be directly used in determining the base curve for the contact lens and the optimum shape for the back surface.

In addition, an OCT can provide a lot of other information that is useful for the whole process of measuring and treating an eye. The thickness of the cornea is an important indicator for the presence and progression of ectasia and keratoconus. A corneal thickness map (called a pachymetry map) can be used for screening and identification and classification of pathologies. The shape and curvature of the posterior cornea is also extremely useful information. This can be used to calculate the total corneal power (TCP), which is useful for prediction of required IOL power in cataract surgery. Furthermore, the anterior chamber depth can be directly measured with OCT. This is also useful for projecting the wavefront from pupil plane to corneal plane to optimize a correction, or for building a "whole-eye" model for advanced treatment calculators.

Figure 53:
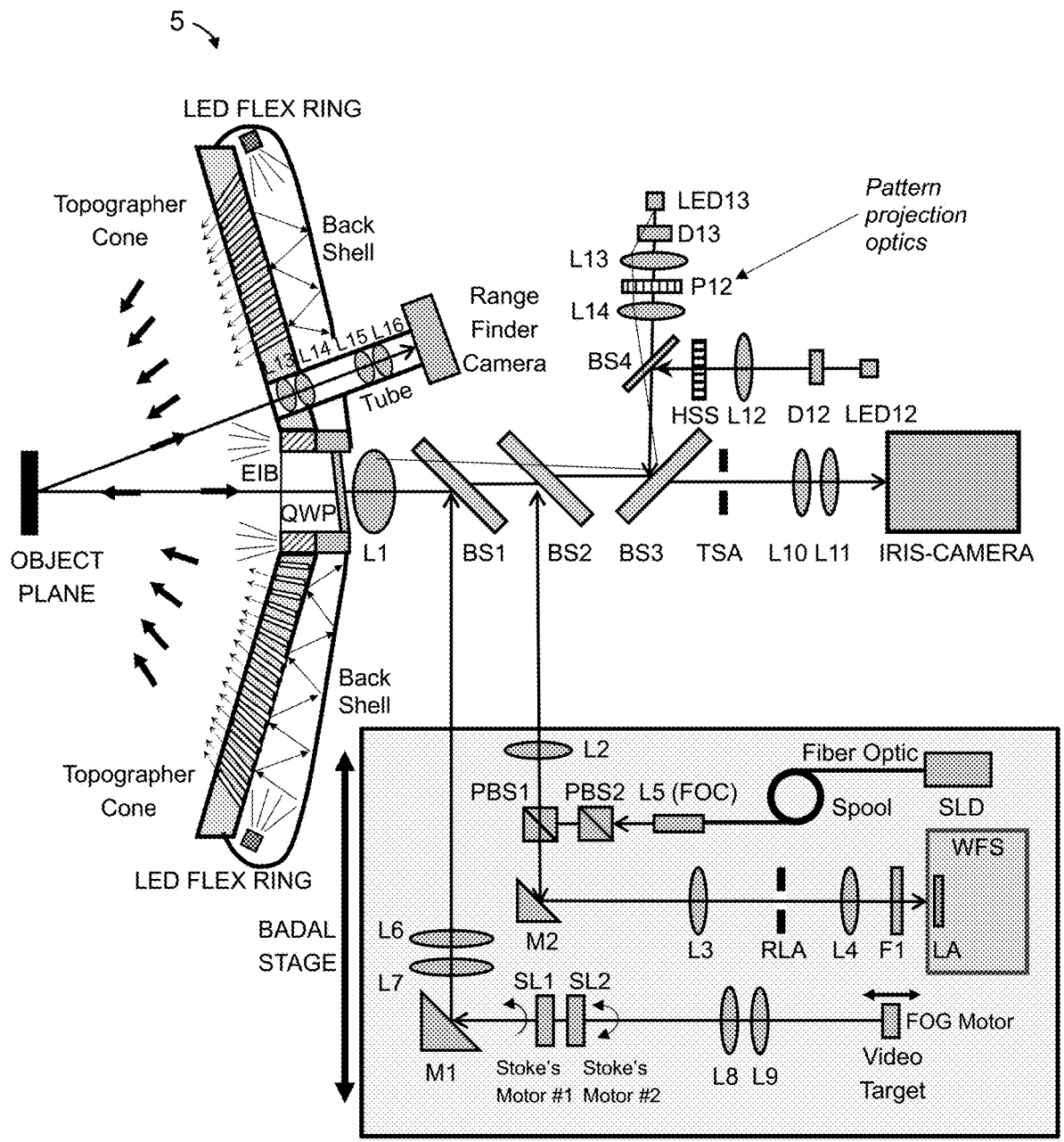
FIG. 53 shows a schematic optical layout of another embodiment of an improved aberrometer, according to the present invention.

FIG. 53 depicts another alternative system and method for measuring the shape of the cornea and sclera. In this case light from LED13 is collimated using lens L13 and passed through a filter P12. This filter would advantageously have a pattern of holes or other pattern that can be projected onto the cornea by lens L14 by passing through BS4. Lens L14 is arranged to share a common focal point with L1, so the pattern is collimated as it is projected onto the cornea. This pattern interacts with a fluorescein dye which has been placed on the cornea. The fluorescein dye absorbs the blue light and fluoresces to produce a greenish/yellow light. This greenish/yellow light can be imaged by the iris and rangefinder cameras. Since the two cameras view the cornea at different angles, each point in the pattern can be used as a source for triangulation, and hence a 3D representation of the surface can be reconstructed. The fluorescein dye interacts with the light pattern to make the surface visible to the cameras at each point. Additionally, it may be advantageous to add a second rangefinder camera on the opposite side to facilitate measurement of both sides of the eye.

FIG. 3 shows a perspective view of an example of an internal support structure and movable stages of a NextWave™ aberrometer 400, according to the present invention. Item 402 is a rigid, horizontal base plate. Item 404 is a stepper motor drive for the stage that moves the instrument transverse to patient's gaze. It moves the instrument for switching between left and right eyes. Item 406 is a slide rail that moves the instrument toward and away from patient. Item 408 is a stepper motor that drives the instrument vertically. Item 410 is a slide rail that move instrument transverse to patient gaze. Item 412 is a chin-rest-assembly support arm. Item 414 is a chin rest. Item 416 is a forehead support strap. Item 418 is an elliptical support frame. Item 420 is a rigid, vertical square tube. The primary optics plate (not shown) attaches to it. Item 422 is an access cover for a bushing that is inside tube. A round shaft (not shown) goes through that bushing. Item 424 is a horizontal bracket that holds up the vertical post 420. A threaded hole in it is what a lead screw from motor 408 connects to. Item 426 is a stepper drive motor for the stage to move the instrument closer to or away from eye. Stepper motor 426 is used to focus the image of the eye. Item 428 is a USB Hub that distributes signals between various cameras and controller cards, so only one USB cable goes in-between the instrument and the computer. Item 430 is an electronics card that drives the stepper motors 404, 408, and 426.

FIG. 4 shows a perspective elevation view of an example of internal components and movable stages of a NextWave™ aberrometer 400, according to the present invention. Instrument 400 comprises: a rigid base plate 402 with an attached vertical support post 420, to which a primary (upper) optics support plate 442 is attached, and to which a secondary (lower) optics support plate 446 is attached. Support arm 412 holds an elliptical frame 418 that has a patient chin rest (not shown). Eye imaging camera 452 is attached to the primary optics plate 442; and wavefront sensor 454 is attached to the secondary optics plate 446. A micro video display target, mounted on a movable electromechanical stage 500, is attached to the secondary optics plate 446. Dual, motor-driven Stoke's lenses assembly 600 can be seen mounted to secondary optics plate 446. Motor drives 426 and 404 are mounted to base plate 402, which provide precise control of the X-Z position of instrument 400 in the horizontal plane. USB interface 428 and electronics boards 430 are attached to base plate 402. Motor drive 450 drives the vertical motion of secondary optics plate 446 (which forms a Badal stage in the vertical direction along the Y-axis). Rangefinder camera 427 is attached to the vertical post 420. A number of components, which are too small to identify in this drawing, are also attached to vertical post 420 via the primary and secondary optics plates 442 and 446, respectively.

FIG. 5 shows a perspective elevation view of an example of upper internal components and movable stages of a NextWave™ aberrometer, according to the present invention. Primary optics plate 442 is bolted to vertical support post 420. Wavefront sensor is bolted to primary optics plate 442. Rangefinder camera 427 is attached to the vertical post 420. Backside shell 440 is mounted to primary optics plate 442.

Figure 6:
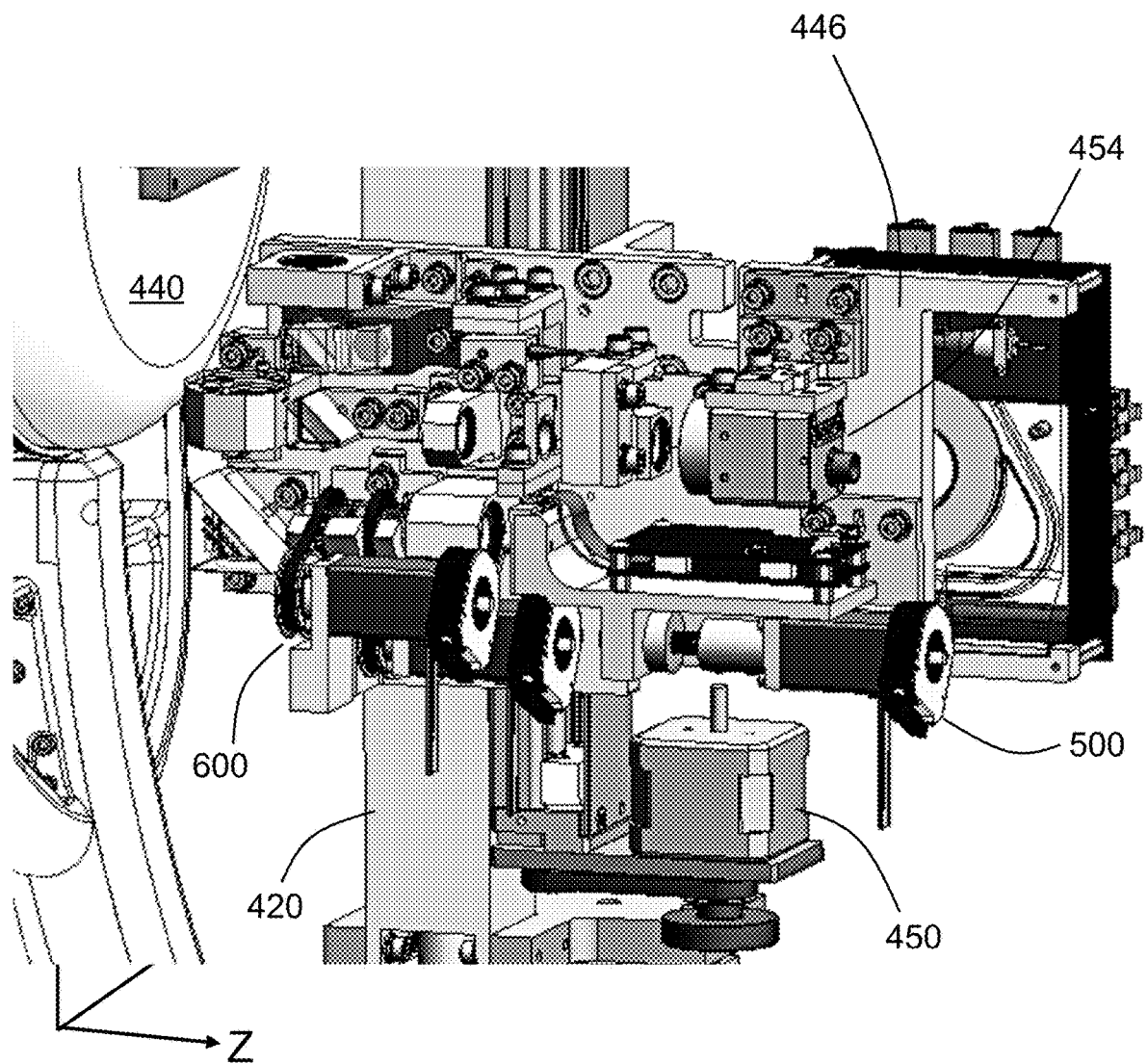
FIG. 6 shows a perspective elevation view of an example of middle internal components and movable stages of a NextWave™ aberrometer, according to the present invention.

FIG. 6 shows a perspective elevation view of an example of middle internal components and movable stages of a NextWave™ aberrometer, according to the present invention. Wavefront sensor 454, micro-video-display assembly 500, and Stoke's cell assembly 600 are all attached to secondary optics plate 446, which is driven up/down by belt-drive motor 450, on vertical support post 420. Back shell 440 can be seen.

Figure 7:
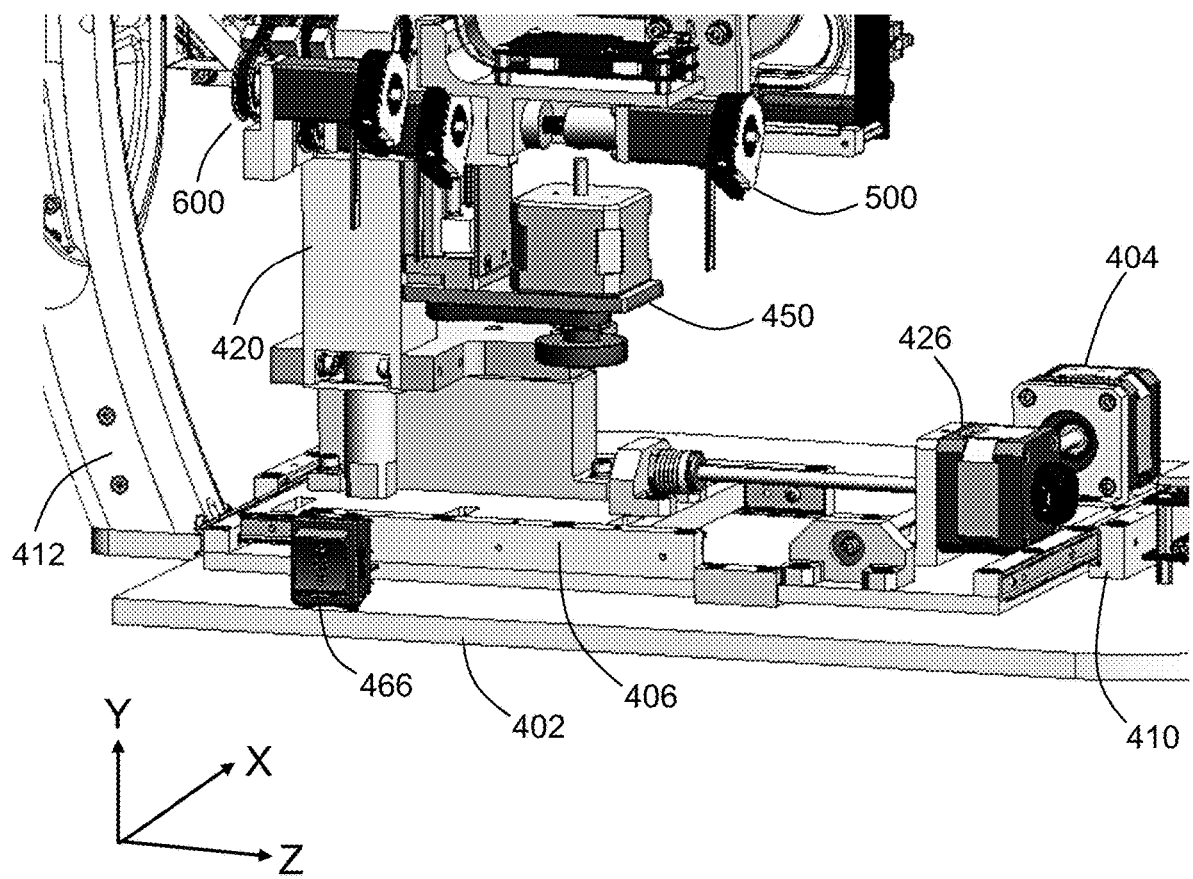
FIG. 7 shows a perspective elevation view of an example of lower internal components and movable stages of a NextWave™ aberrometer, according to the present invention.

FIG. 7 shows a perspective elevation view of an example of lower internal components and movable stages of a NextWave™ aberrometer, according to the present invention. Micro-video-display assembly 500, and Stoke's lens assembly 600 are all attached to secondary optics plate 446, which is driven up/down by belt-drive motor 450, on vertical support post 420. Motor 426 drives the entire optics assembly 400 forward/back along the Z-axis direction along slide rail 406. Motor 404 drives the entire optics assembly 400 left/right along the X-axis direction along slide rail 410. Motorized chin rest switch 466 can be seen.

Figure 8:
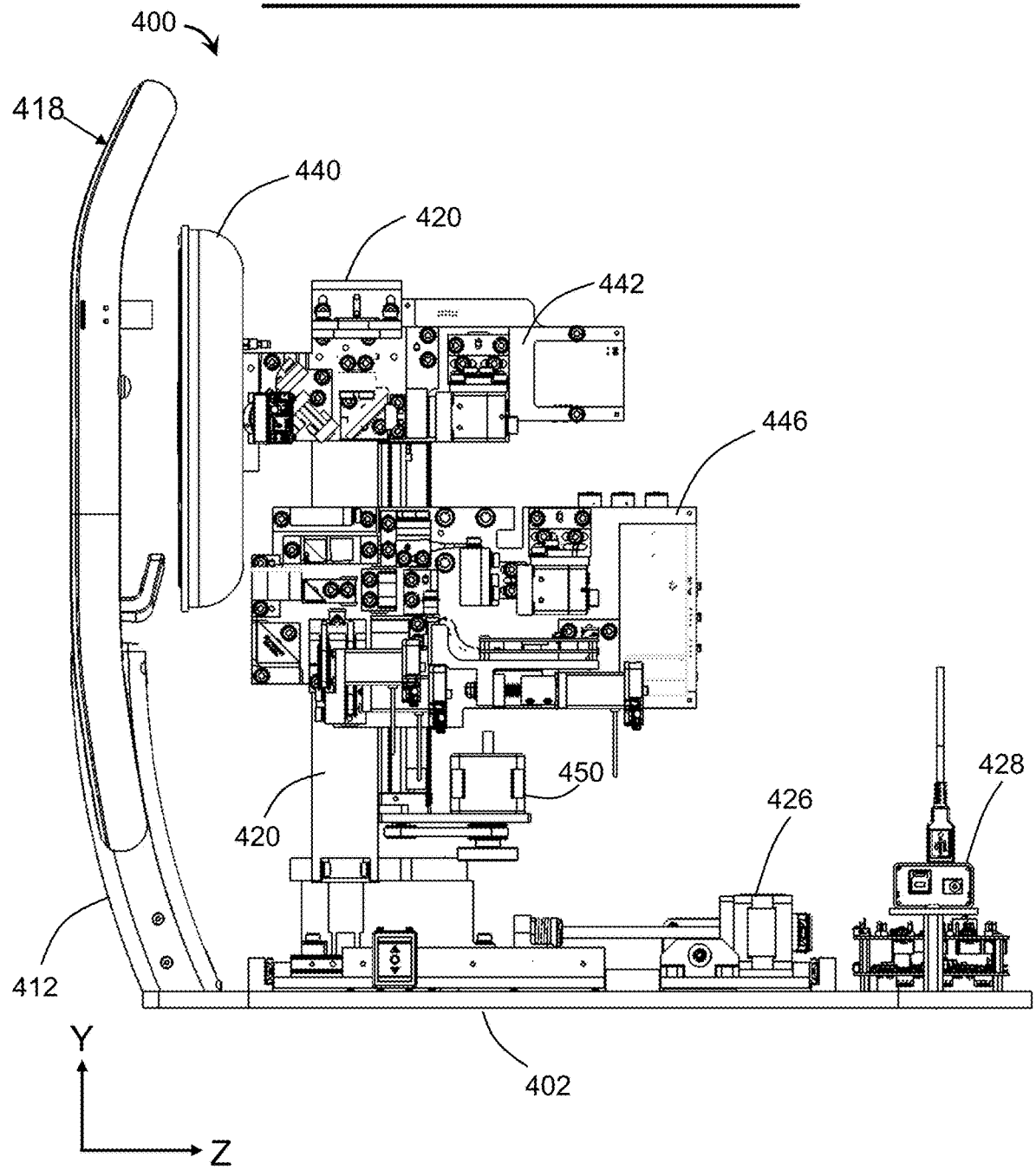
FIG. 8 shows a side elevation view of an example of internal components and movable stages of a NextWave™ aberrometer, according to the present invention.

FIG. 8 shows a side elevation view of an example of internal components and movable stages of a NextWave™ aberrometer, according to the present invention. Primary optics plate 422 is attached to vertical post 420, which is perpendicular to base plate 402. Motor 450 drives the secondary optics plate 446 Up/Down as a Badal Stage. USB hub 428 is mounted to base plate 402. Frame 418 and support arm 412 are attached to base plate 402. Back shell 440 is attached to vertical post 420.

Figure 9:
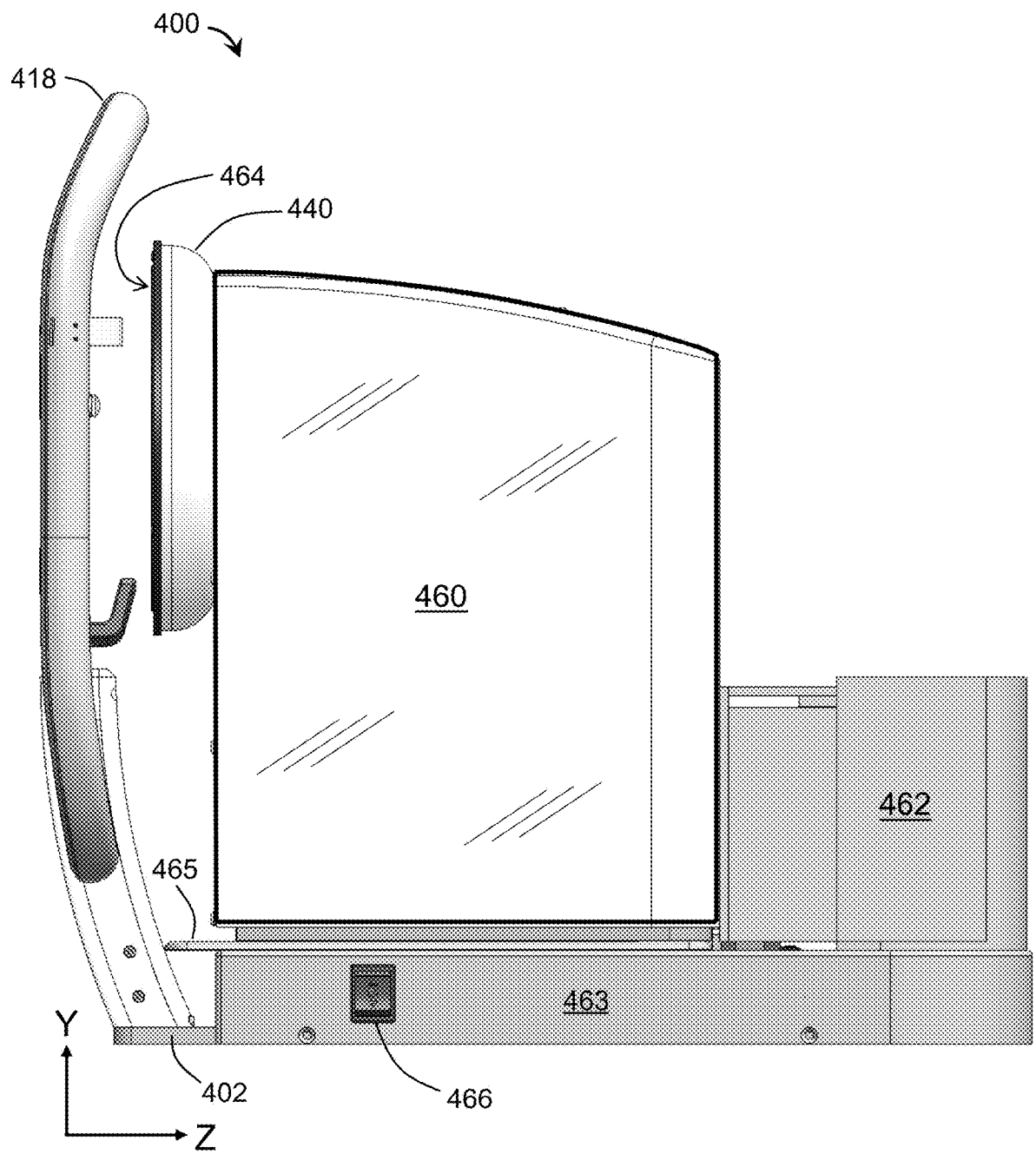
FIG. 9 shows a side elevation view of an example of a NextWave™ aberrometer, with the covers on, according to the present invention.

FIG. 9 shows a side elevation view of an example of a NextWave™ aberrometer, with the covers on, according to the present invention. Main cover 460 covers the optical components (not shown), while rear cover 462 covers the USB hub 4128 (not shown) and electronics boards 430 (not shown). Motorized chin rest switch 466 can be seen. Bottom cover 463 and horizontal cover plate 465 can be seen.

Figure 10:
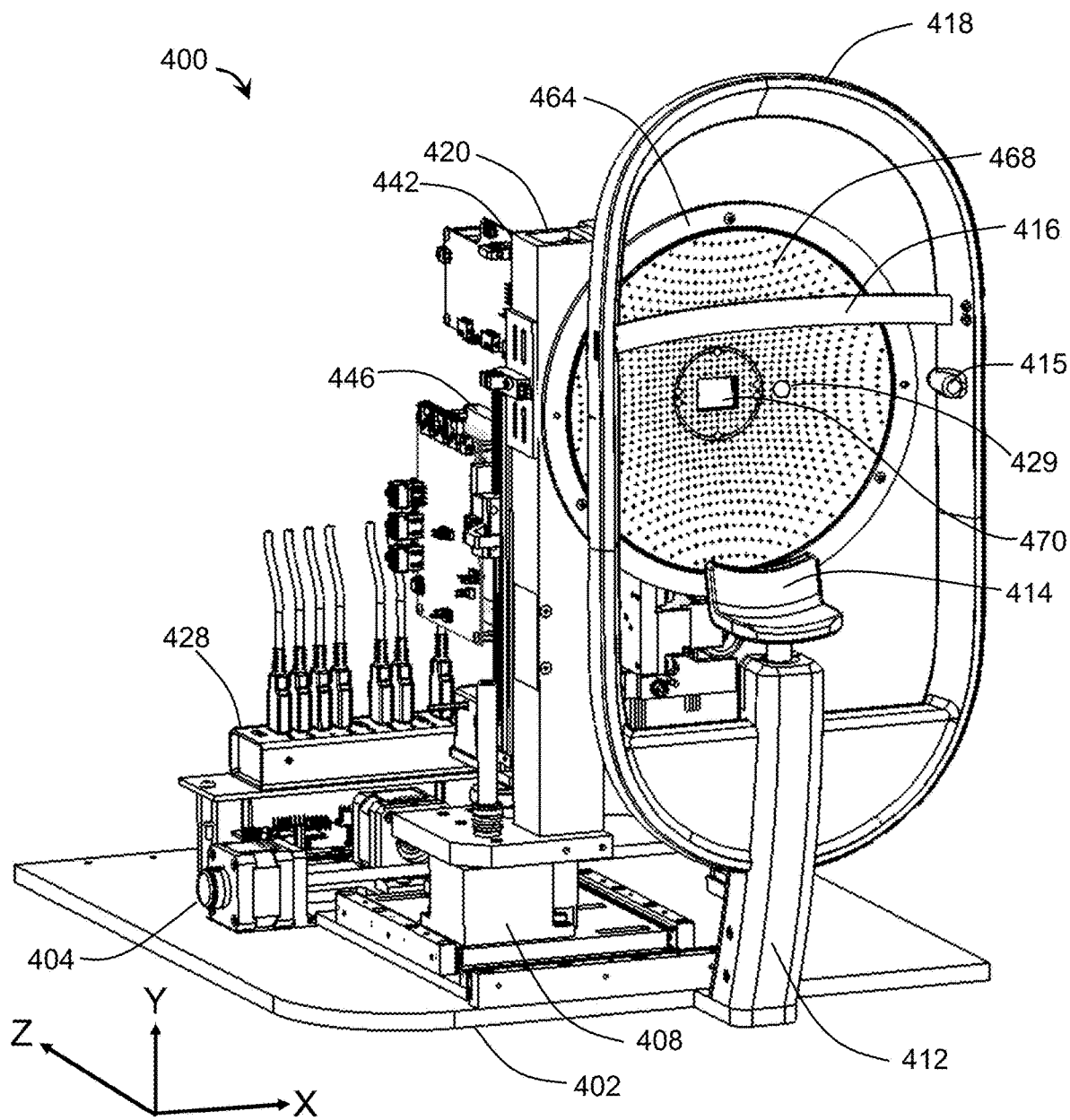
FIG. 10 shows a perspective front elevation view of an example of a NextWave™ aberrometer, with the covers off, according to the present invention.

FIG. 10 shows a perspective front elevation view of an example of a NextWave™ aberrometer, with the covers off, according to the present invention. Support post 412 and vertical post 420 are attached to base plate 402. Motor 404 drives the entire optics assembly 400 left/right along the X-axis direction along slide rail 410. Motor 408 drives the entire optics assembly 400 Up/Down. These motors are used to adjust (using a joystick (not shown) or automatic system) the XYZ position of aperture 470 relative to the patient's head resting on chin rest 414, in order to accurately align the eye's gaze into aperture 470. Frame 418 holds forehead rest strap 416 and artificial mechanical model eye 415. Primary optics plate 442 and secondary optics plate 446 are attached to vertical support post 420. USB hub 428 can be seen. Conically-shaped topographer cone 464 contains a plurality (e.g., 800 holes) of holes 468 that are oriented conically to all point towards a single location (i.e., the eye's location) (See FIG. 1).

Figure 11:
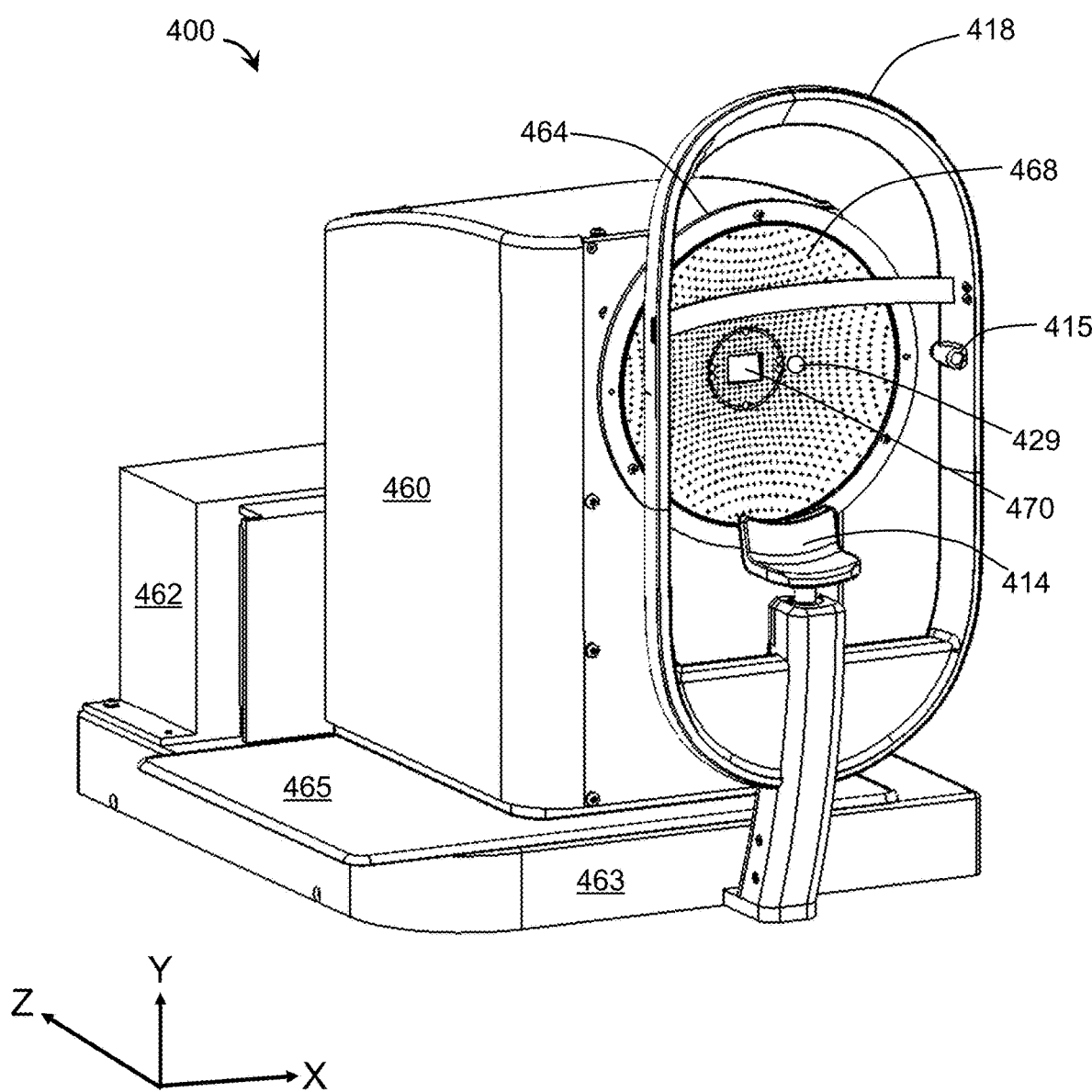
FIG. 11 shows a perspective front elevation view of an example of a NextWave™ aberrometer, with the covers on, according to the present invention.

FIG. 11 shows a perspective front elevation view of an example of a NextWave™ aberrometer, with the covers 460 and 462 on, according to the present invention. Chin rest 414, elliptical frame 418, and model eye 415 can be seen, along with Conically-shaped topographer cone 464 containing the plurality of holes 468. Bottom cover 463 and horizontal cover plate 465 can be seen.

Figure 12:
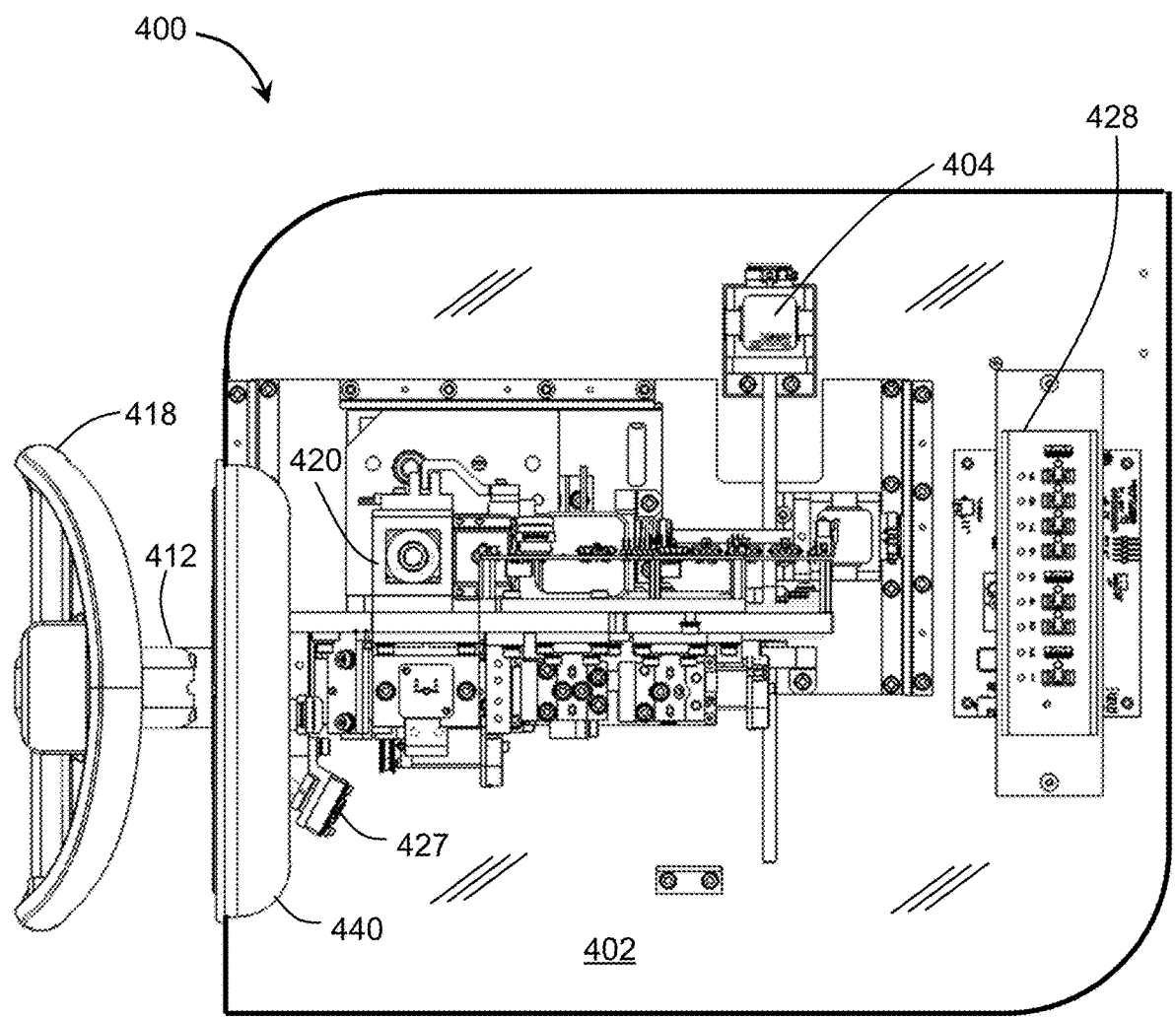
FIG. 12 shows a plan view of an example of internal components and movable stages of a NextWave™ aberrometer, with the covers off, according to the present invention.

FIG. 12 shows a plan view of an example of internal components and movable stages of a NextWave™ aberrometer, with the covers off, according to the present invention. Vertical support post 420 is attached to base plate 402. Range finder camera 427 can be seen, which passes through back shell 440 and topographer cone (not shown). Motor 404 drives optics assembly 400 left/right along the X-axis direction.

Figure 13:
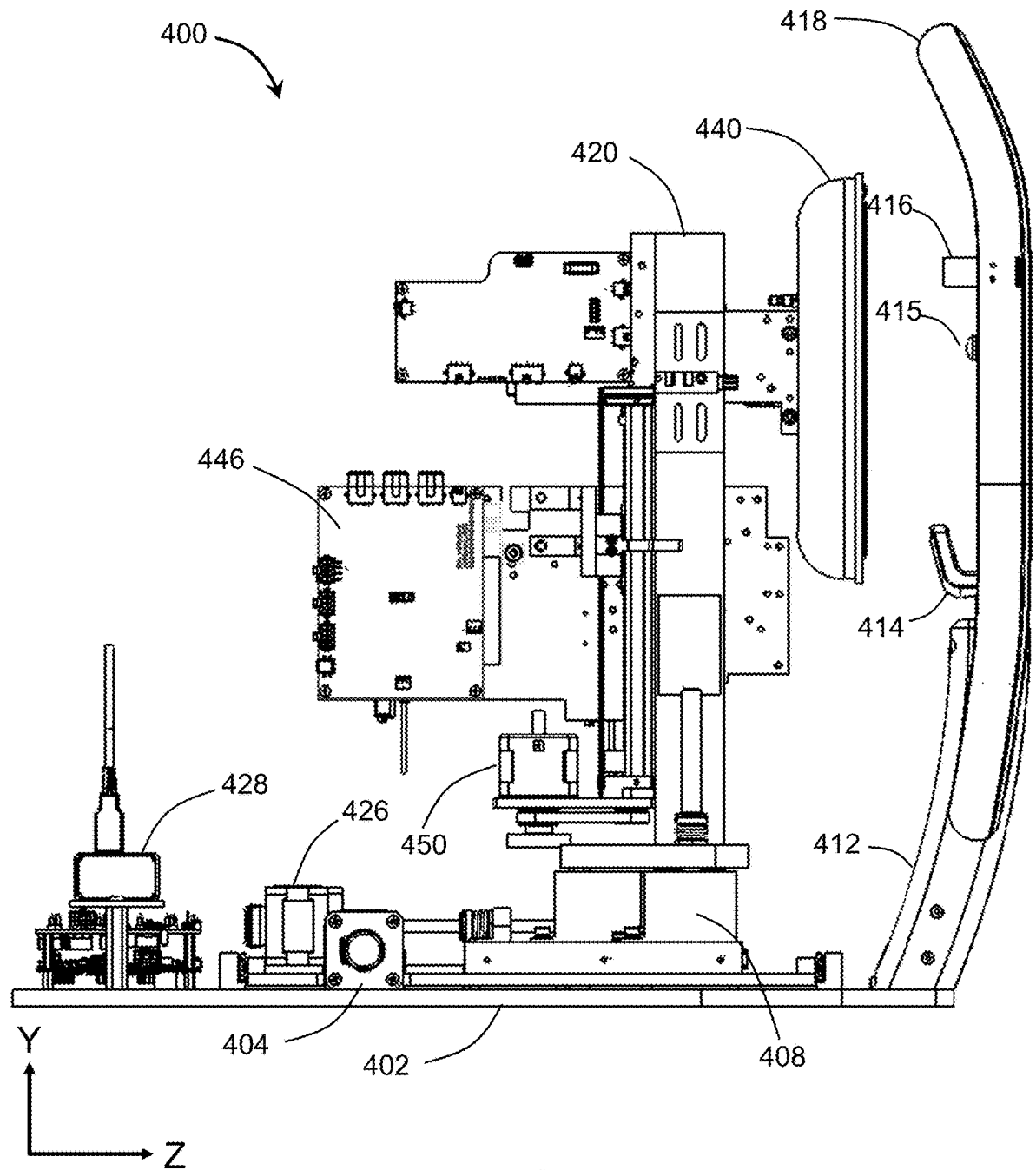
FIG. 13 shows a side elevation view of an example of internal components and movable stages of a NextWave™ aberrometer, with the covers off, according to the present invention.

FIG. 13 shows a side elevation view of an example of internal components and movable stages of a NextWave™ aberrometer, with the covers off, according to the present invention. Motor 404 drives the entire optics assembly 400 left/right along the X-axis direction; and motor 426 drives the entire optics assembly 400 forward/back along the Z-axis direction. Motor 408 drives the entire optics assembly 400 Up/Down. These motors are used to adjust (using a joystick (not shown) or automatic system) the XYZ position of aperture 470 relative to the patient's head resting on chin rest 414, in order to accurately align the eye's gaze into aperture 470 (not shown). Frame 418 holds forehead rest strap 416 and artificial mechanical model eye 415. Primary optics plate 442 and secondary optics plate 446 are attached to vertical support post 420. USB hub 428 can be seen, along with back shell 440.

Figure 14A:
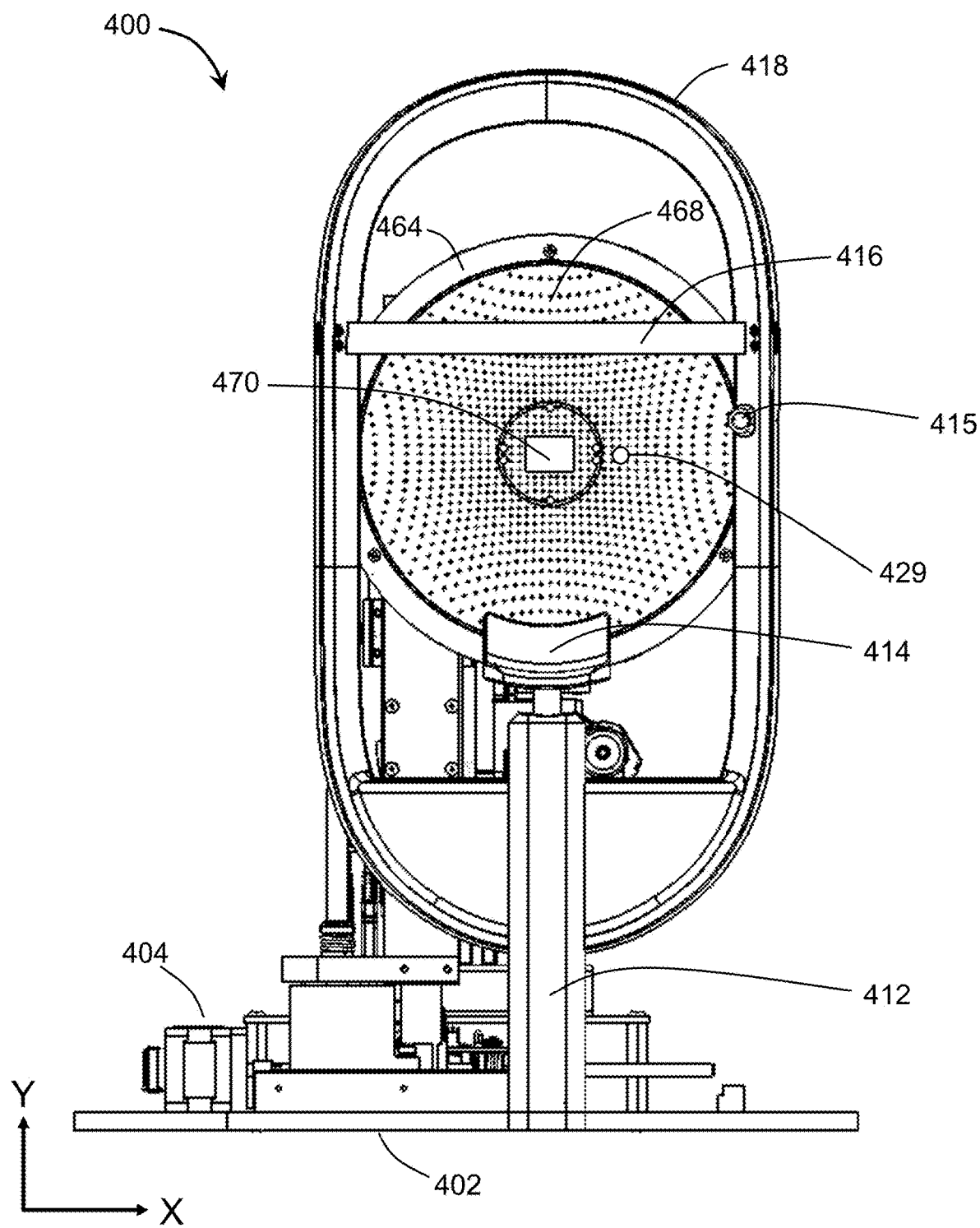
FIG. 14A shows a front elevation view of an example of internal components and movable stages of a NextWave™ aberrometer, with the covers off, according to the present invention.

FIG. 14A shows a front elevation view of an example of internal components and movable stages of a NextWave™ aberrometer, with the covers off, according to the present invention. Motor 404 drives the entire optics assembly 400 left/right along the X-axis direction, relative to base plate 402. Frame 418 holds forehead rest strap 416 and artificial mechanical model eye 415. Chin rest 414, forehead strap 416, elliptical frame 418, support arm 412, and model eye 415 can be seen, along with conically-shaped topographer cone 464 containing the plurality of holes 468. Central aperture in topographer cone 464 can be seen, along with an opening 429 for accessing range finder camera 427.

Figure 14B:
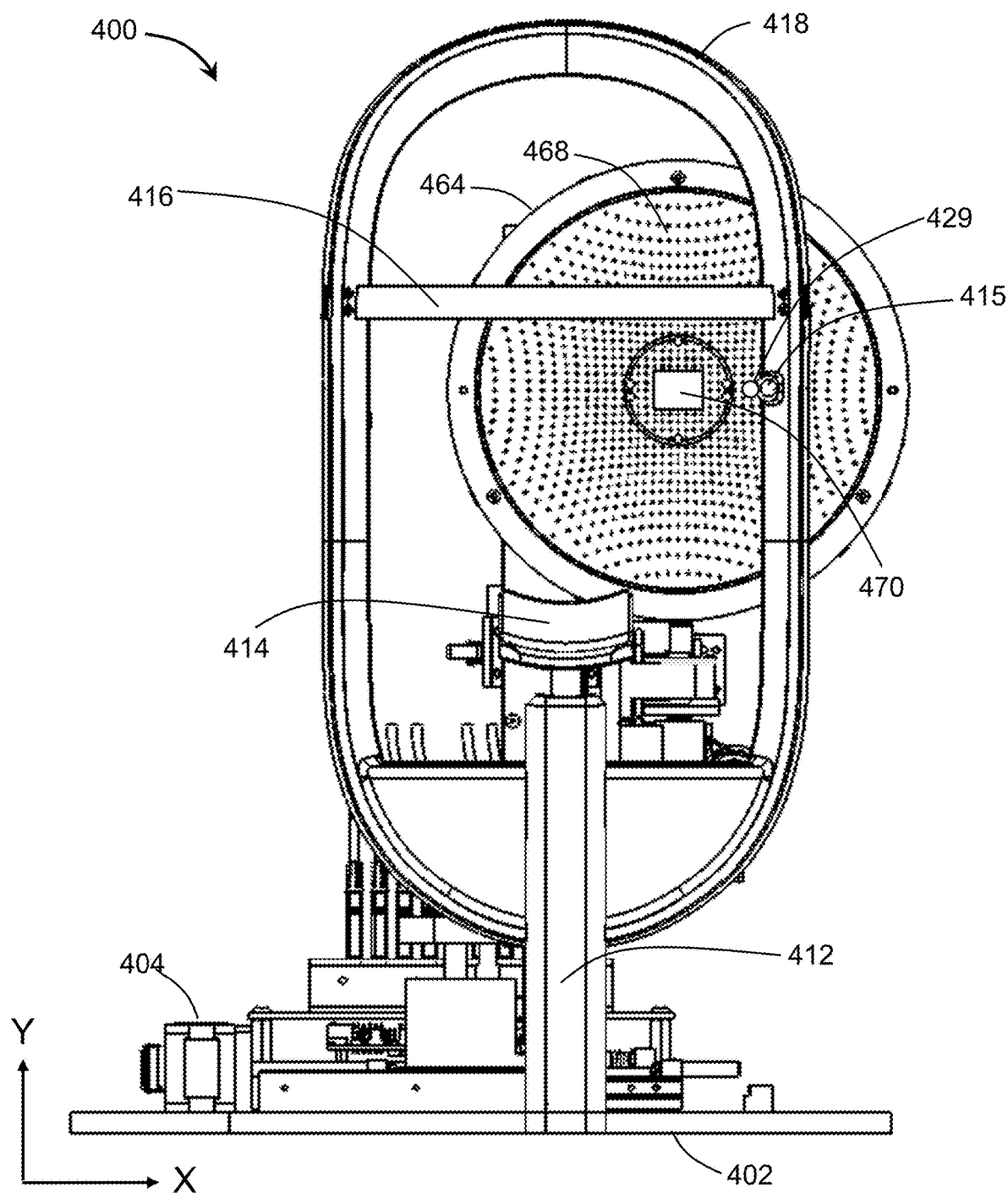
FIG. 14B shows a front elevation view of an example of internal components and movable stages of a NextWave™ aberrometer, with the covers off, according to the present invention.

FIG. 14B shows a front elevation view of an example of internal components and movable stages of a NextWave™ aberrometer, with the covers off, according to the present invention. In this view, topographer cone 464 and aperture 470 are aligned with the right eye of a patient (not shown). Motor 404 drives the entire optics assembly 400 left/right along the X-axis direction, relative to base plate 402. Frame 418 holds forehead rest strap 416 and artificial mechanical model eye 415. Chin rest 414, forehead strap 416, elliptical frame 418, support arm 412, and model eye 415 can be seen, along with conically-shaped topographer cone 464 containing the plurality of holes 468. Central aperture in topographer cone 464 can be seen, along with an opening 429 for accessing range finder camera 427.

Figure 15:
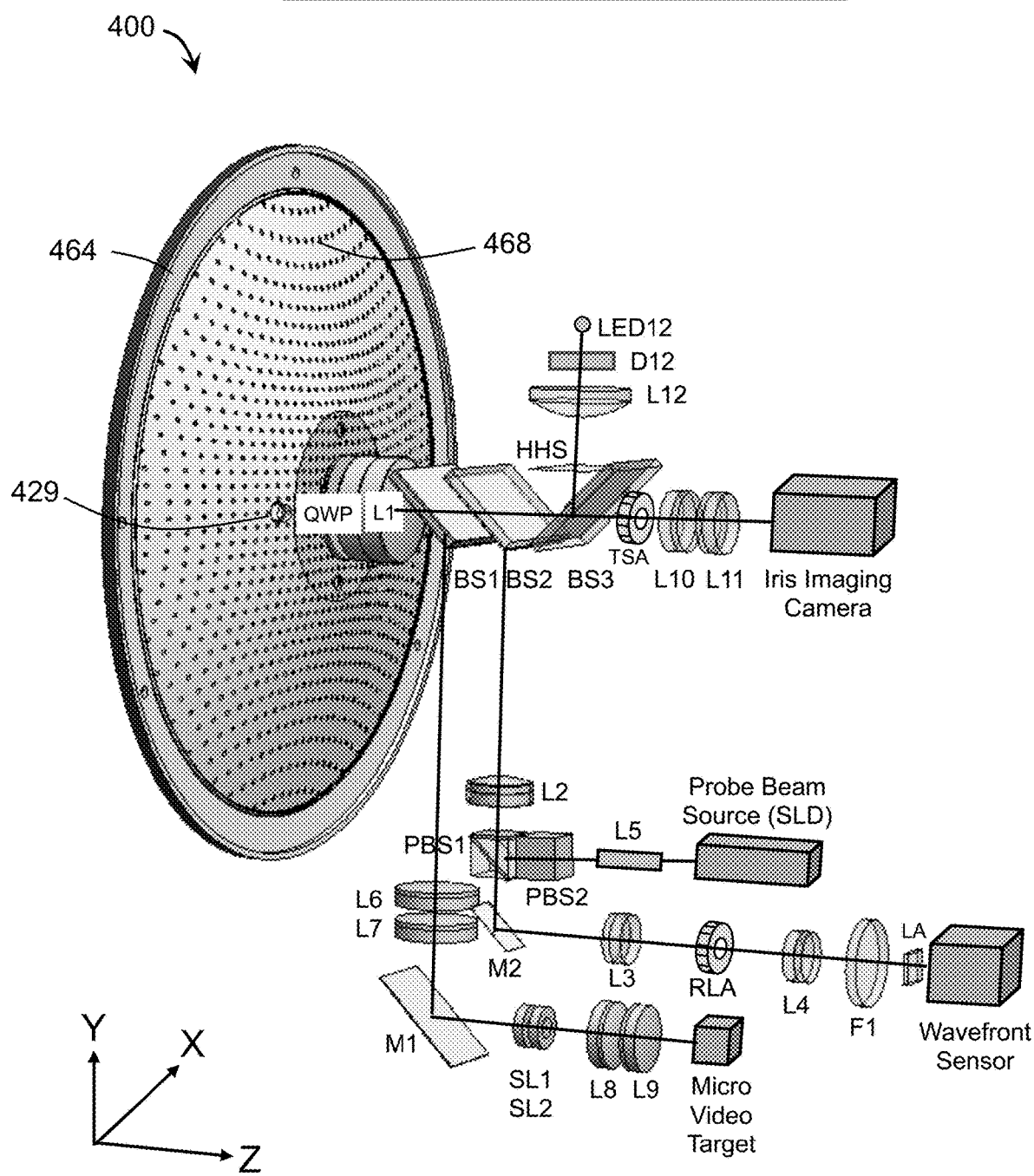
FIG. 15 shows an exploded perspective view of an example of just the internal optical components of a NextWave™ aberrometer, with the covers off, according to the present invention.

FIG. 15 shows an exploded perspective view of an example of just the internal optical components (i.e., without support structures) of a NextWave™ aberrometer, with the covers off, according to the present invention. The Iris Camera Path comprises light going through QWP (shown in front of L1), L1, BS1, BS2, BS3, TSA, L10, L11 and into the Iris Camera. Light for the Iris Camera Path comes from the eye illumination board (EIB) (not shown). The Topographer Path goes from a pattern of many lighted holes (e.g., 800 non-parallel, conically-oriented holes) in the Topographer Cone, with light reflecting off the cornea and passing through to the Iris Camera Path. The Helmholtz path starts with light from LED12 going through diffuser D12, then Lens12, and then through the Helmholtz Source HHS (a plate with parallel holes in it), reflects off BS3, then through BS2, BS1, L1, QWP, reflects off the cornea, and then light reverses and goes back through QWP, L1, BS1, BS2, BS3, TSA, L10, L11 and on to the Iris Camera.

In FIG. 15, the Probe Beam path starts at the probe beam source (which can be a super luminescent laser diode (SLD)), then goes through a fiber optic cable (which can be coiled in a spool for mechanical convenience) through a Fiber Optic Collimator (L5), goes through polarizing beamsplitter PBS2, reflects off polarizing beamsplitter PBS1, goes through L2, reflects off BS2, goes through BS1, L1, QWP and then through the cornea, forming a spot of light on the retina. Some of that light scatters off the retina, leaves the eye, and then goes back into the instrument along the Wavefront Sensor path (as described next). The Wavefront Sensor path goes through QWP, L1, BS1 reflects off BS2, through L2, PBS1, reflects off M2, through L3, RLA, L4, F1 (Filter 1) and onto the lenslet array (LA) of wavefront sensor WFS. The purpose of Filter 1 (F1) is to block out room lights so that the instrument can be used in a fully lit room and avoid potential crosstalk with the imaging or corneal topographer (CT) channels. Optionally, the filter F1 may pass only 840 nm. That would allow us to turn on the 760 nm and 930 nm LEDs at the same time that the wavefront sensor is collecting images. Note that light going comprising the Wavefront Sensor path comes from the Probe Beam (described above).

In FIG. 15, the Visual Target Path goes from the eye, through QWP, L1, reflects off BS1, goes through L6, L7, reflects off M1, goes through Stoke's Lens1, Stokes Lens2, L8, L9 and then reaches the micro video target (MVT). The topographer cone 464 has a plurality of numerically-controlled machined holes 468 (e.g., 800 holes) that all point, in a conical fashion, towards a central point (i.e., the eye at the object plane), which collimates light originating from backside LED strip lights (similar to a Helmholtz light source (HHS)) towards the object plane. The aperture 429 for a Range Finder Camera (not shown) can be seen. Note: the light sources can all be infrared sources, or a mixture of visible and infrared sources.

Figure 16:
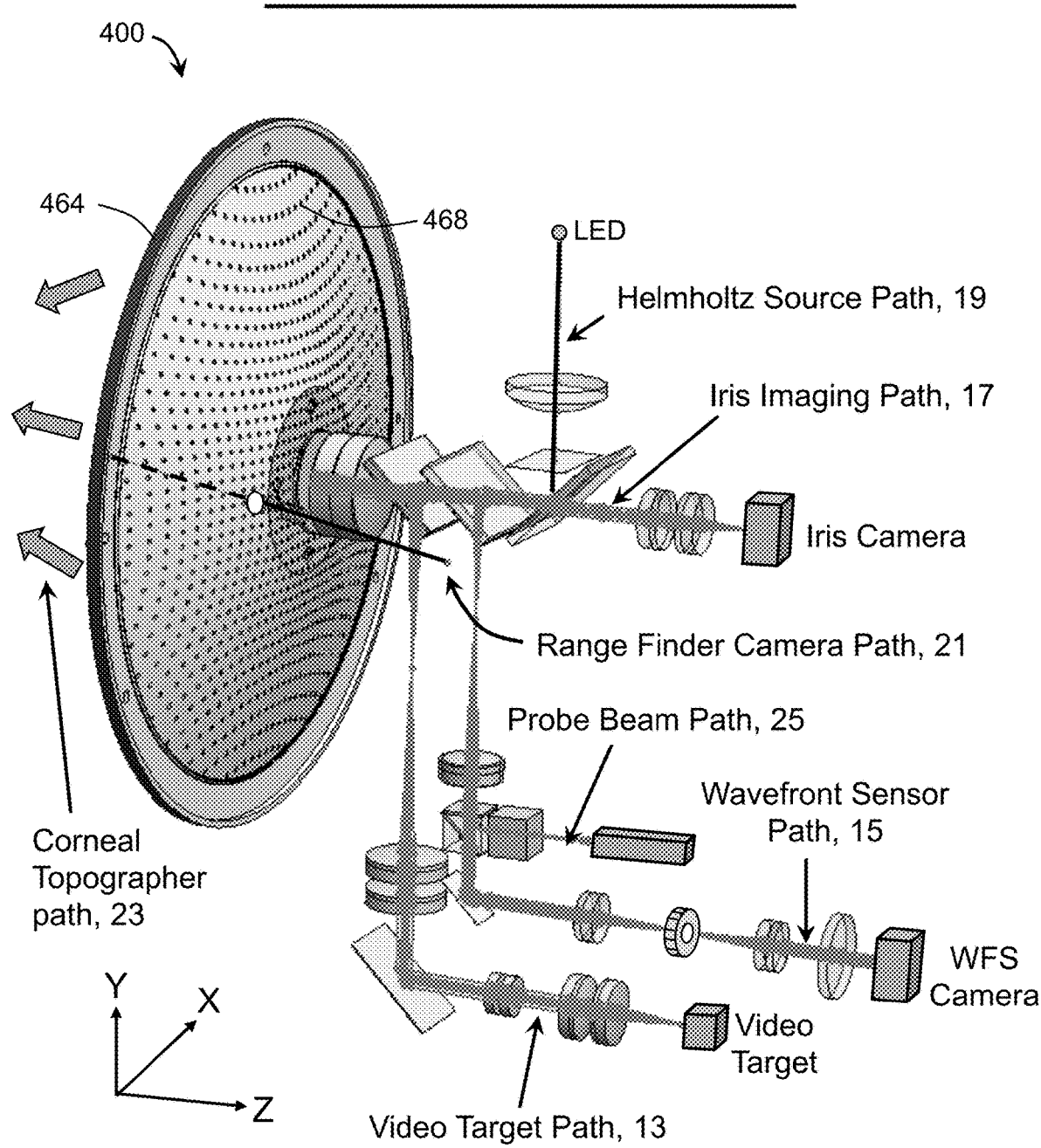
FIG. 16 shows an exploded perspective view of an example of just the internal optical components of a NextWave™ aberrometer, with the covers off, according to the present invention.

FIG. 16 shows an exploded perspective view of an example of just the internal optical components of a NextWave™ aberrometer (i.e., without support structures), with the covers off, according to the present invention. Helmholtz Source Path 19; Iris Imaging Path 17; Wavefront Sensor Path 15; and Video Target Path 13 is shown, along with topographer cone 464 and hole 468 through cone 464.

Figure 17:
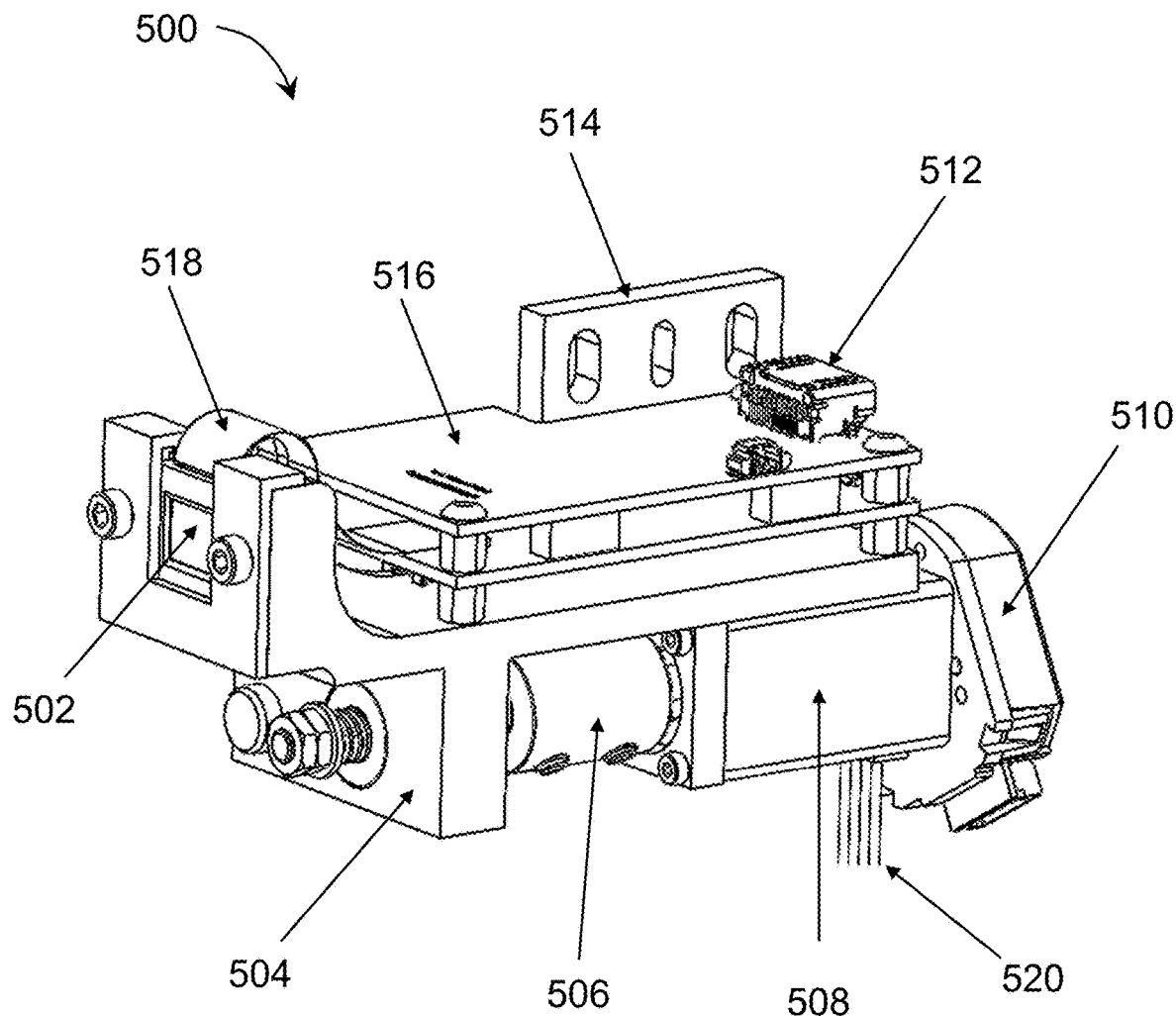
FIG. 17 shows a perspective view of a motorized micro video display, according to the present invention.

FIG. 17 shows a perspective view of a motorized micro video display assembly 500, for moving the video target back and forth along the main optical path, according to the present invention. Item 502 is the micro-video-display fixation target. Item 504 is a bracket that moves the video display in and out along a direction that is perpendicular to the plane of the video display. Item 506 is a coupler that connects a stepper motor shaft to a drive lead screw. Item 508 is a stepper motor. Item 510 is an angle encoder unit for counting rotations of the stepper motor 508. Item 512 is an electrical connector. Item 514 is a bracket for attaching the drive assembly to a secondary optics plate 446. Item 516 is an electrical control card for driving the micro-video-display 500. Item 518 is a flexible cable connecting the electrical control card to the micro-display 502. Item 520 comprise wires connecting to the stepper motor 508.

FIG. 18 shows a perspective view of an example of a Stoke's cell 600, which comprises a pair of movable, cylindrical lens 620 and 622 that can rotate independently of the other lens, according to the present invention. One cylindrical lens has negative cylinder power, while the other lens has positive cylinder power. Item 602 is a belt drive from stepper motor 606 to the barrel that holds the front Stoke's lens 620. Item 604 is a bracket for holding the front stepper motor 612. Item 606 is a front stepper motor for rotating the front lens 620. Items 608 and 610 are wires for energizing the stepper motors. Item 612 is a rear stepper motor for rotating the rear lens 622. Item 614 is a bracket for holding the rear stepper motor 612. Item 616 is a bracket that attaches to secondary optics plate (not shown) and has a curved groove (not shown) in it that holds barrel #1 and barrel #2. The barrels each have a ring of teeth in them for the belts to engage and drive. Item 618 is a belt from the rear stepper motor 612 to a barrel that holds the rear lens 622.

FIG. 19 shows a graph illustrating a first example of timing sequences of key components of a NextWave™ aberrometer fora single frame time=100 ms. The corneal topographer (CT) component is always ON (or, it could be pulsed). Next, the iris visual camera triggers ON for an exposure period of, for example, 30 ms. Then, after the iris camera turns OFF, the Super Luminescent Diode (SLD) turns ON for approximately 40 ms. During the time the SLD is ON, the wavefront camera triggers ON for an exposure period of, for example, 30 ms. This entire process is repeated with a repeat cycle frequency of about 10-60 Hz.

Wavefront Guided (WFG) Contact Lens Customization Process:

To design and fabricate a customized contact lens to correct for visual disturbances caused by higher order aberrations, there are a number of steps:
1. Measure the subject's bare eye to determine aberrations, amount of HOA present, and determining if the subject is eligible for correction using CCL;
2. Determining a refraction and fit parameters (base curve, diameter, sphere, cylinder, axis) from step 1, or use the subjects habitual lens parameters and fabricating a "trial lens" with appropriate fiducial marks;
3. Measure the patient dynamically with the trial lens. Determine lens stability, fit and comfort of the trial lens. Iterate until a good fit has been obtained;
4. Using the measured aberrations from step 3, integrate the wavefront surface into the contact lens front surface shape. Fabricate CCL using diamond turning on a lathe or other method; and
5. Measure the patient with WFG contact lenses from step 4. Determine residual level of wavefront errors and stability.

Zernike Polynomials:

Zernike polynomials are commonly used to describe the wavefront error caused by an eye's imperfect optics. The coefficients of the Zernike polynomials are proportional to the magnitude of the aberrations, and are expressed in microns. The $2^{nd}$ order terms represent the Low Order Aberrations (LOA), which are also characterized as sphere and cylinder or defocus and astigmatism. Low Order Aberrations can be corrected with conventional spectacles and contact lenses. The coefficients for those terms that are $3^{rd}$ order and greater and consider Higher Order Aberrations (HOA). Higher Order Aberrations cannot be corrected with conventional optics but require a more complex shape. The following plots describes a set of three measurements made on a patient with a modest amount of myopia. The dynamic measurements were made with an aberrometer on (1) a bare eye, (2) an eye fitted with a trial contact lens, and (3) a wavefront guided (WFG) customized contact lens, according to the present invention.

Wavefront Guided (WFG) Contact Lens Design:

A contact lens can be described by two opposing surfaces: a Back curve, $B(x_i, y_i)$, and a Front curve $F(x_i, y_i)$. The correction of the contact lens is determined by the curvature of the difference=$F(x_i, y_i) - B(x_i, y_i)$. The surfaces are defined at a series of points $(x_i, y_i)$. Any astigmatism may be included on the back surface. This helps somewhat with the fit of the contact lens, so this should not also be included on the front.

The instrument's aberrometer measures the Refraction, Base Curve, Iris Diameter (white to white), Centers, Offsets and wavefront as a function of time. The pupil is defined over a circle $(x_p, y_p)$ and radius $R_p$, which is offset from the contact lens center by $(x_p, y_p)$.

The measured wavefront values are described by a set of Zernike polynomials (See ANSI standard Z80.28-2004) with associated Zernike coefficients, $C_n^m$ (measured), and intended design $C_n^d$ (design). Each of these is defined over a certain fixed pupil diameter, $R_z^m$ or $R_z^d$. During the measurement sequence, the pupil size varies with each blink. Thus, the data collected during a measurement is a table of values as a function of time:

$$[t, x_p(t), y_p(t), R_p(t), CL_x(t), CL_y(t), CL_{rot}(t), C_n^m(t)].$$

The intended design is derived from these measurements. On the contact lens the XY offset from center, $CL_x(t) - X_p$, $CL_y(t) - Y_p$, is determined by analyzing the difference between pupil and CL centers. The optimum "position" (after removing blinks) is the place where the contact lens is stable for the longest time. This may be a manual or judgement input initially, with an automatic approach that can be developed later. In any case, there is a final intended offset and rotation of the correction pattern, $[(x_d, y_d), a_d]$, measured relative to the CL center and fiducials as:

$$[(x_d, y_d), a_d] \sim [(<x_p - CL_x>, <y_p - CL_y>), <CL_{rot}>];$$

with averaging operator $<>$ being chosen to minimize the total time deviation from the average (mean) value. The set of measurements used for this is designated $Pt_i$.

Note that during the measurement with the contact lens and fiducial marks in place, the over-refraction is obtained (where the measurement is the residual error of the eye fitted with the contact lens). That is, for each point the Zernike polynomials can be used to determine the residual $S_{eq}$, S, C and A (where $S_{eq}$ stands for Sphere Equivalent, S stands for Sphere, C for Cylinder, and A for Axis). Note that $S_{eq}$=S+C/2. This could (optionally) be added to the base curve $B(x_i,y_i)$ and front curve $F(x_i,y_i)$ to adjust the basic design over the whole contact lens, or it could be just included in the wavefront patch. Note that the axis A can be adjusted to compensate for how the lens fits on the eye.

At this point, the contact lens design surfaces can be generated with appropriate points files $F_b(x_i,y_i)$, $B_b(x_i,y_i)$ that include any adjustments to the refraction. This allows us to use a standard set of trial lenses that don't have the final refraction included. Alternatively, we can use this for a small adjustment based on the over-refraction.

Next, a surface $W_c(x,y)$ is defined that represents the intended wavefront correction. First, a transition zone is a radial function defined by:

$$T(r) = \begin{cases} 1, & r < r_0 \\ 1 - \cos\pi\left(\dfrac{r-r_0}{r_1-r_0}\right), & r_0 > r \geq r_1 \\ 0, & r \geq r_1 \end{cases} \quad \text{Eq. (1)}$$

The wavefront correction function is then defined as:

$$W_c(x,y) = T(r)[\Sigma_n C_n^d Z_n(x-x_d, y-y_d)] + (1-T(r))F_b(x-x_d, y-y_d). \quad \text{Eq. (2)}$$

The design correction can be calculated using a series of five filters, according to the following steps:
1. Scale all Zernike coefficients to some standard size (e.g., minimum in the dynamic measurement sequence used for the averaging operation (set $Pt_i$));
2. Determine the significance of each term. Do not include any correction for terms where $|C_n^m| < \sigma(C_n^m)$. That is, if the error in the term is greater than the term itself, we should not try to correct for it;
3. Average the Zernike coefficients over set $Pt_i$;
4. Rescale the Zernike coefficients to the largest pupil measured in $Pt_i$; and
5. Determine the appropriate limits, $r_0$ and $r_1$ for the transition zone (T(r)).

At this point, we have an intended wavefront design that includes: the offsets $(x_d, y_d)$, rotation $(a_d)$, and an analytic description of the intended wavefront-guided surface design shape $W_c(x,y)$. To integrate this shape with the CL design points file (PTS), this analytic surface is evaluated at each point, i, in the front curve PTS file, according to:

$$F_f(x,y) = B_{(x,y)} + Wc((x_i-x_d)\cos(-a_d), (y_i-y_d)\sin(-a_d)). \quad \text{Eq. (3)}$$

The fiducial locations can be adjusted to make them horizontal. Each radial slice of the contact lens has a precise shape, and the pattern can be integrated by integrating the desired WF correction into the base lens.

FIGS. 20-39B depict measured Zernike polynomial coefficients from subject SP003, a 22 y.o. female with normal levels of HOAs. These aberrations were measured in various eye conditions (bare, trial contact lens, and WFG lens) over a 30 second long sequence using the invention disclosed herein. Data from blinks or missing fiducials has been removed. Note in these figures that the aberrations are fairly constant over time. For the WFG lens case, this is indicative that the contact lens is stable on the eye and not exhibiting any substantial rotation.

Figure 20:
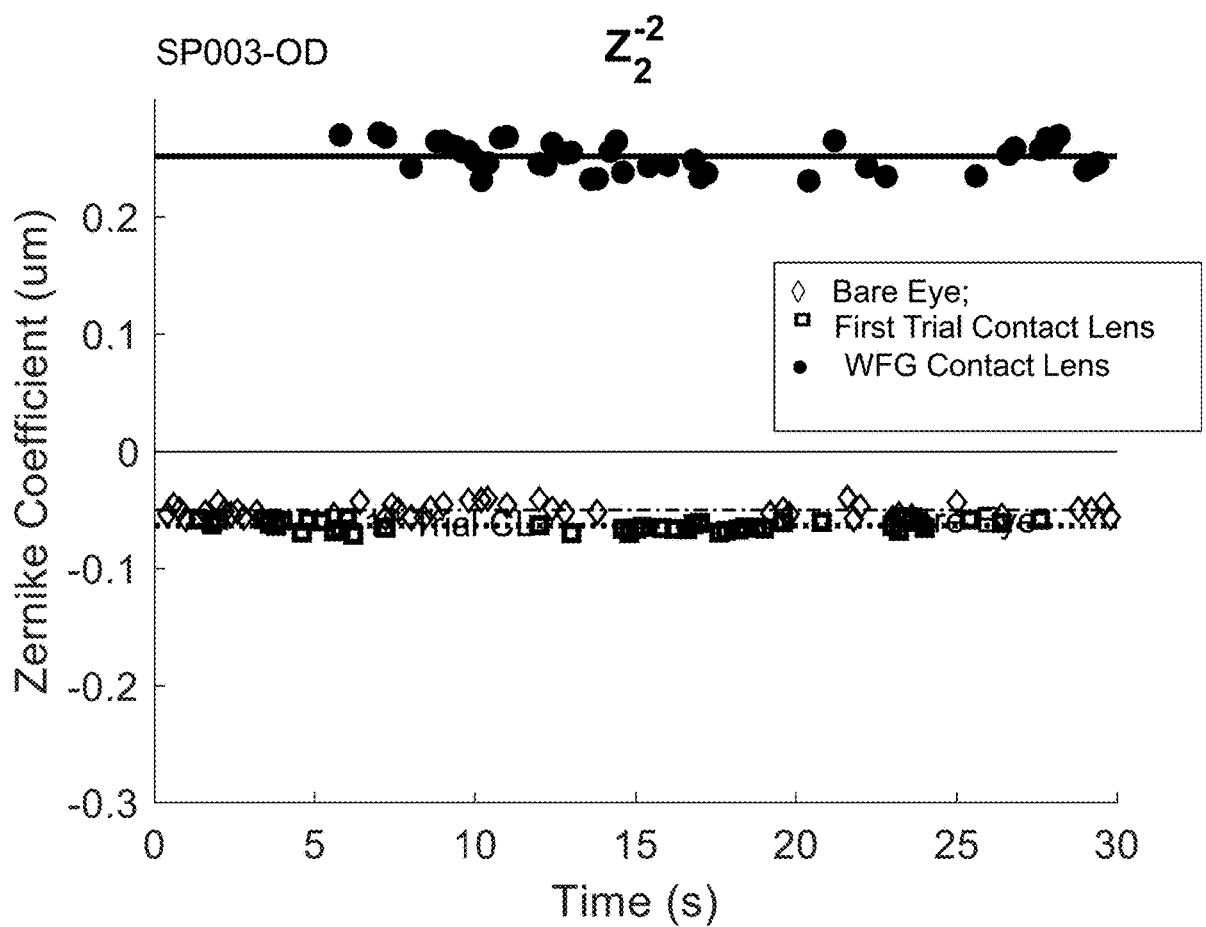
FIG. 20 shows a dynamic graph of a measured $Z_2^{-2}$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 20 show a dynamic graph of a measured $Z_2^{-2}$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The bare eye and eye fitted with a trial lens have the lowest (best) time-averaged Zernike coefficients.

Figure 21:
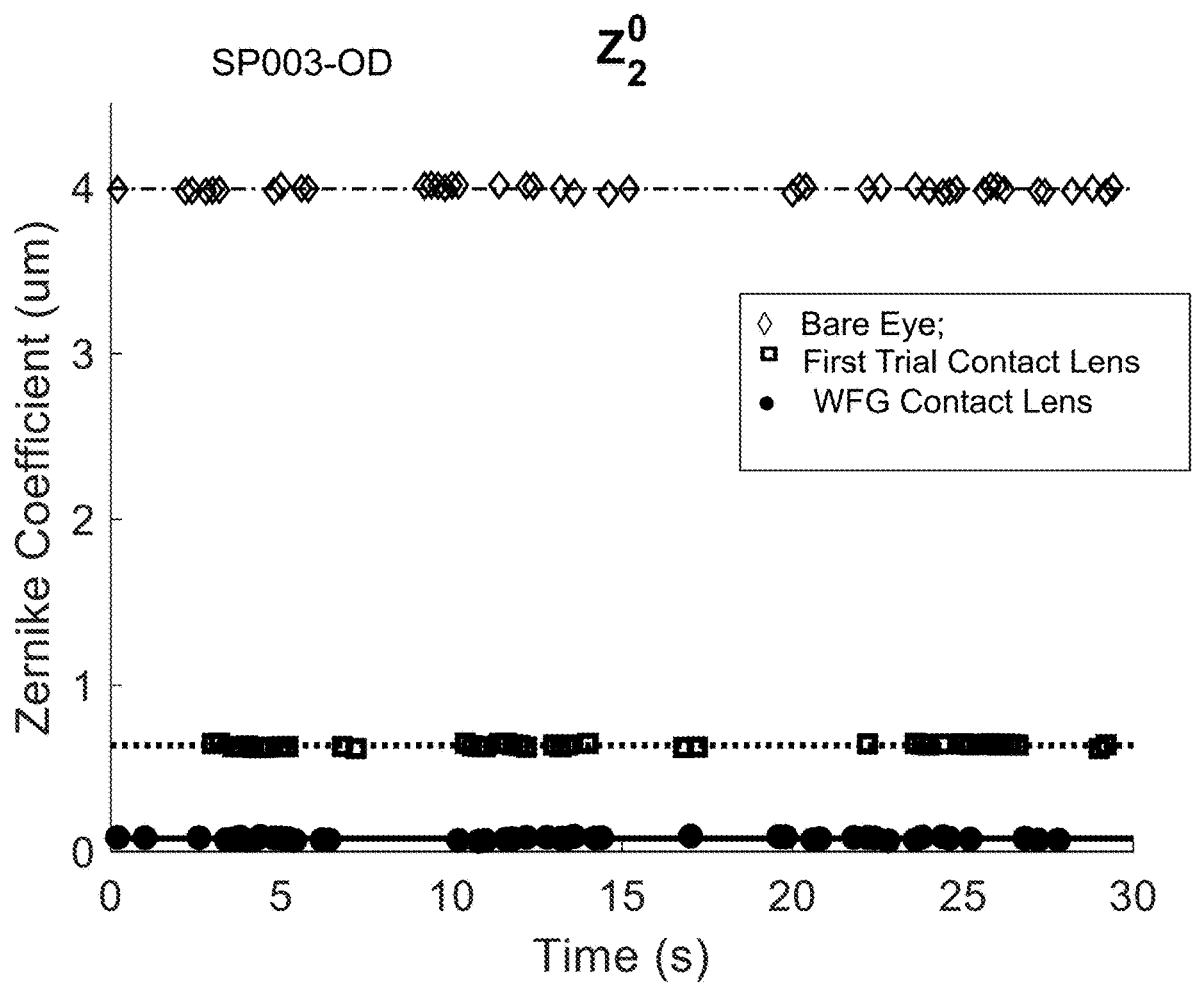
FIG. 21 shows a dynamic graph of a measured $Z_2^0$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 21 shows a dynamic graph of a measured $Z_2^0$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized contact lens has the lowest (best) time-averaged Zernike coefficient.

Figure 22:
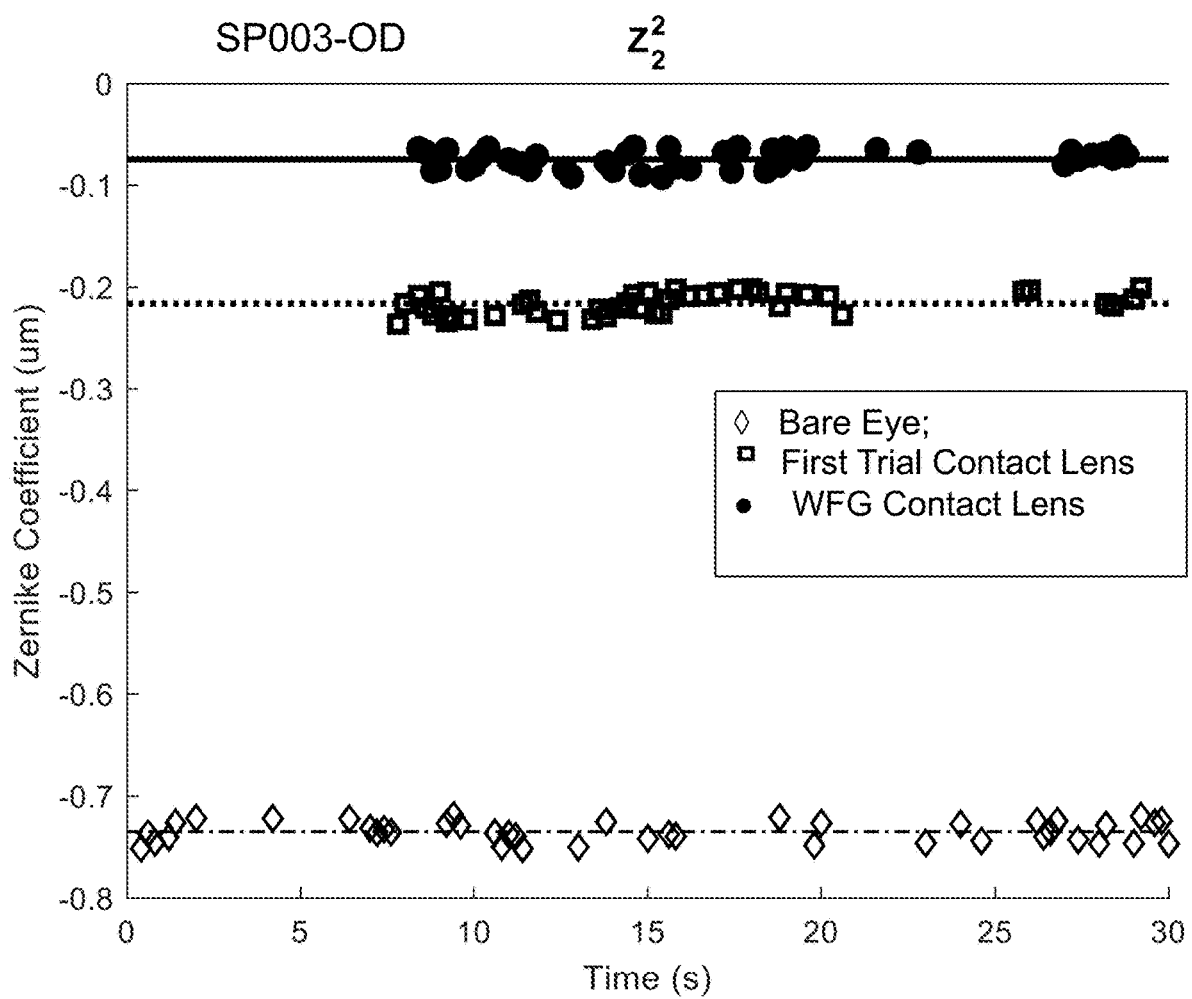
FIG. 22 shows a dynamic graph of a measured $Z_2^2$ Zernike polynomial coefficient for Patient #SP003-OD versus time, for: (1) a bare eye, (2) an eye fitted with a first trial contact lens, and (3) an eye fitted with a wavefront guided (WFG3 customized contact lens, as measured by the present invention.

FIG. 22 shows a dynamic graph of a measured $Z_2^2$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized CL has the lowest (best) time-averaged Zernike coefficients.

Figure 23:
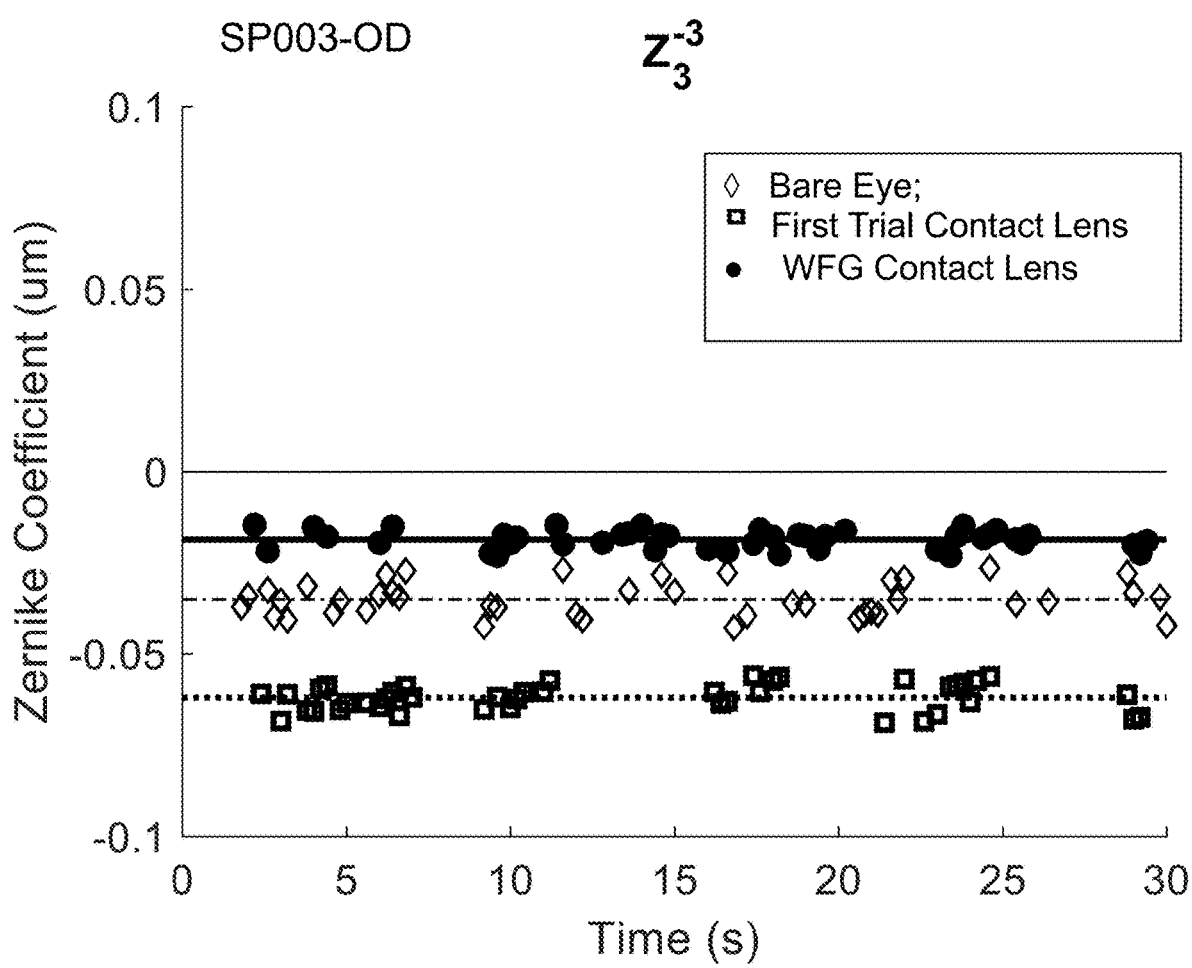
FIG. 23 shows a dynamic graph of a measured $Z_3^{-3}$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 23 shows a dynamic graph of a measured $Z_3^{-3}$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized CL has the lowest (best) time-averaged Zernike coefficients.

Figure 24:
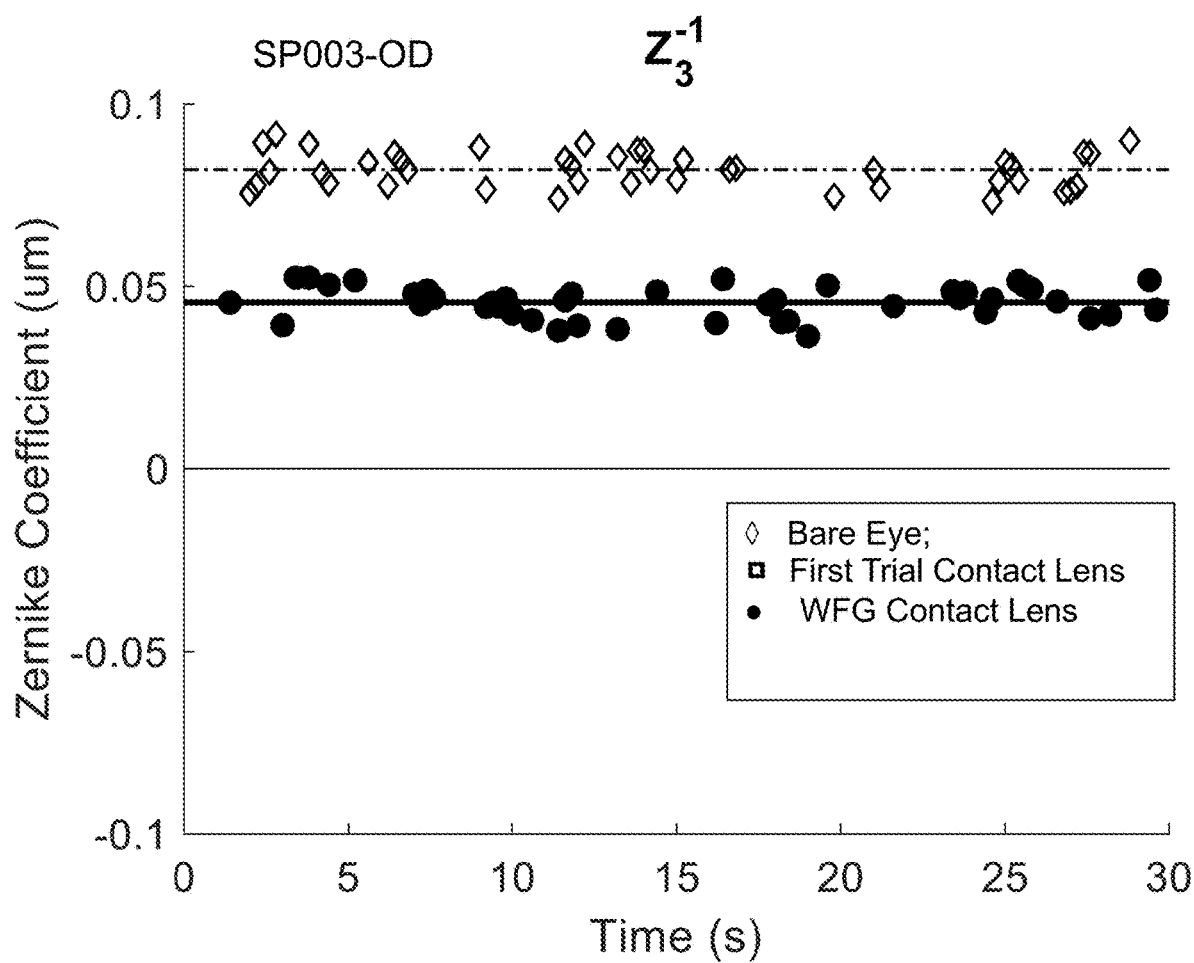
FIG. 24 shows a dynamic graph of a measured $Z_3^{-1}$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 24 shows a dynamic graph of a measured $Z_3^{-1}$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized CL has the lowest (best) time-averaged Zernike coefficients.

Figure 25:
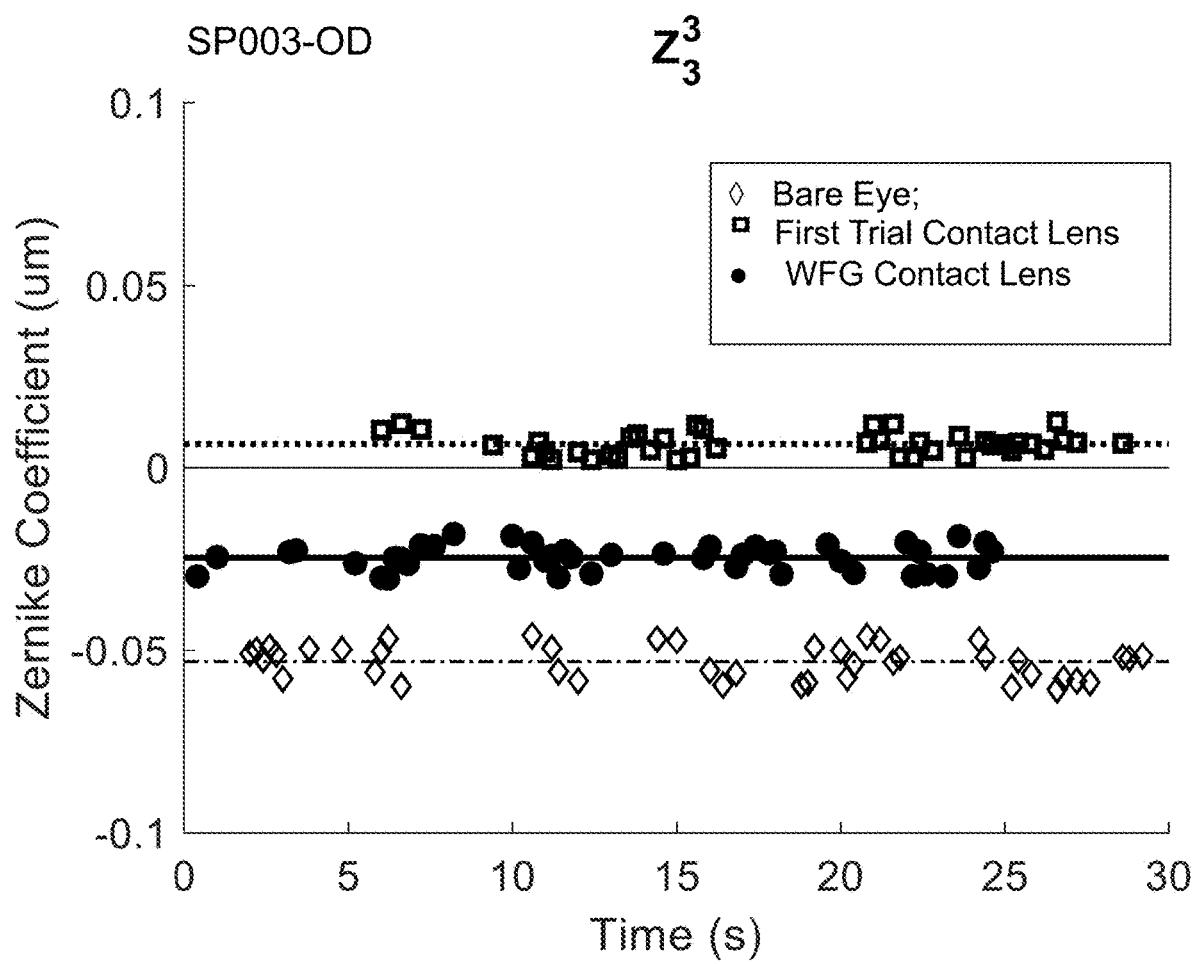
FIG. 25 shows a dynamic graph of a measured $Z_3^3$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 25 shows a dynamic graph of a measured $Z_3^3$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The first trial CL has the lowest (best) time-averaged Zernike coefficients.

Figure 26:
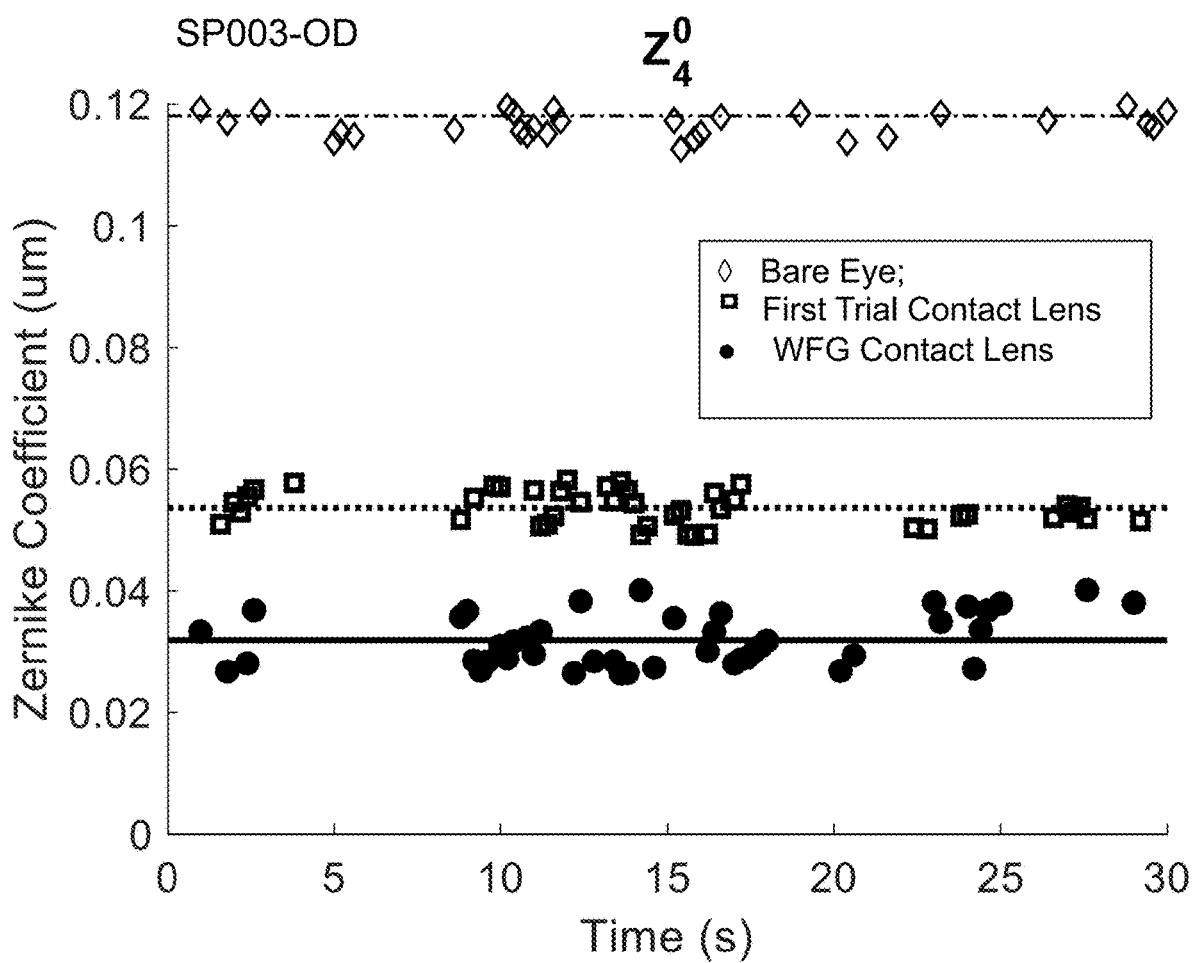
FIG. 26 shows a dynamic graph of a measured $Z_4^0$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 26 shows a dynamic graph of a measured $Z_4^0$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized CL has the lowest (best) time-averaged Zernike coefficients.

Figure 27:
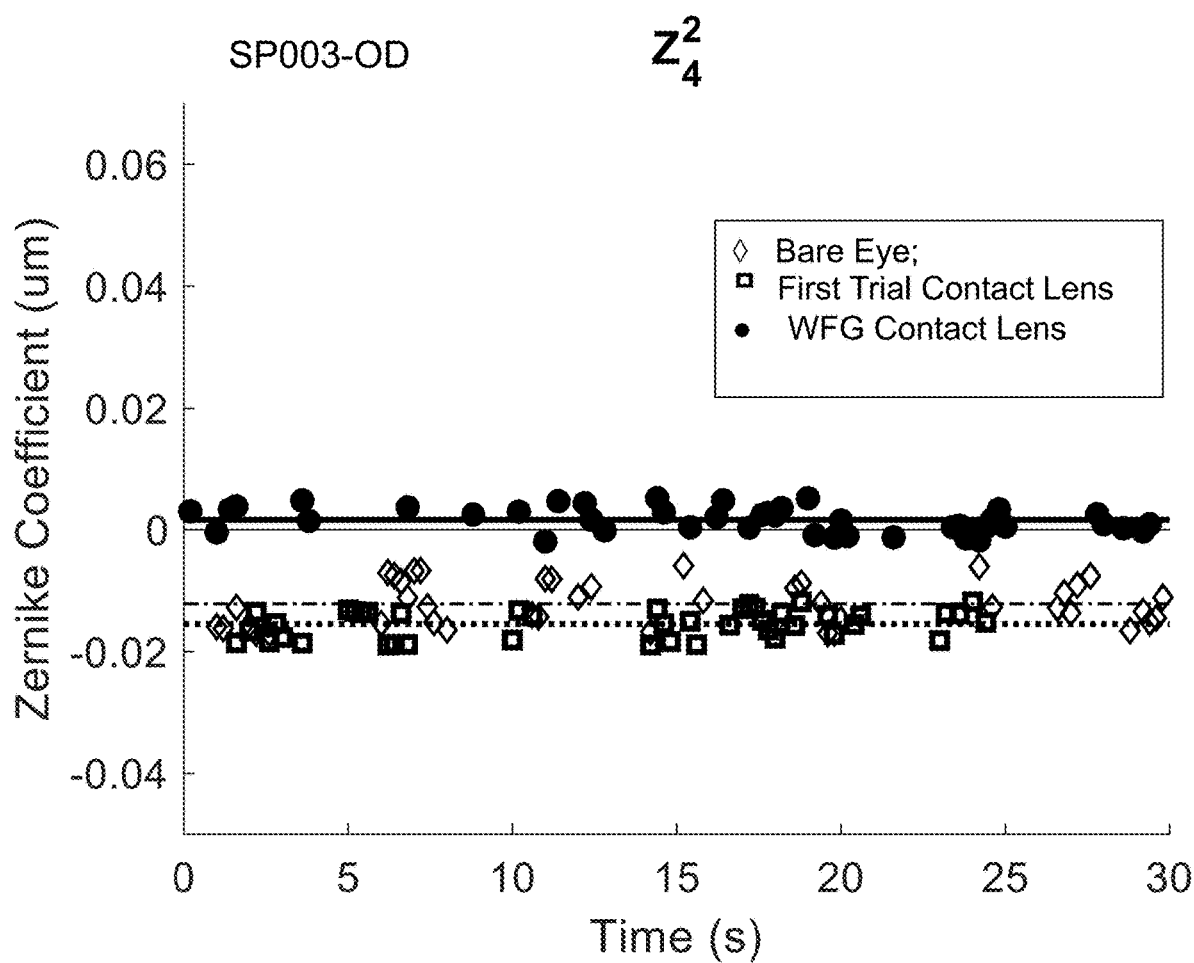
FIG. 27 shows a dynamic graph of a measured $Z_4^2$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 27 shows a dynamic graph of a measured $Z_4^2$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized CL has the lowest (best) time-averaged Zernike coefficients.

Figure 28:
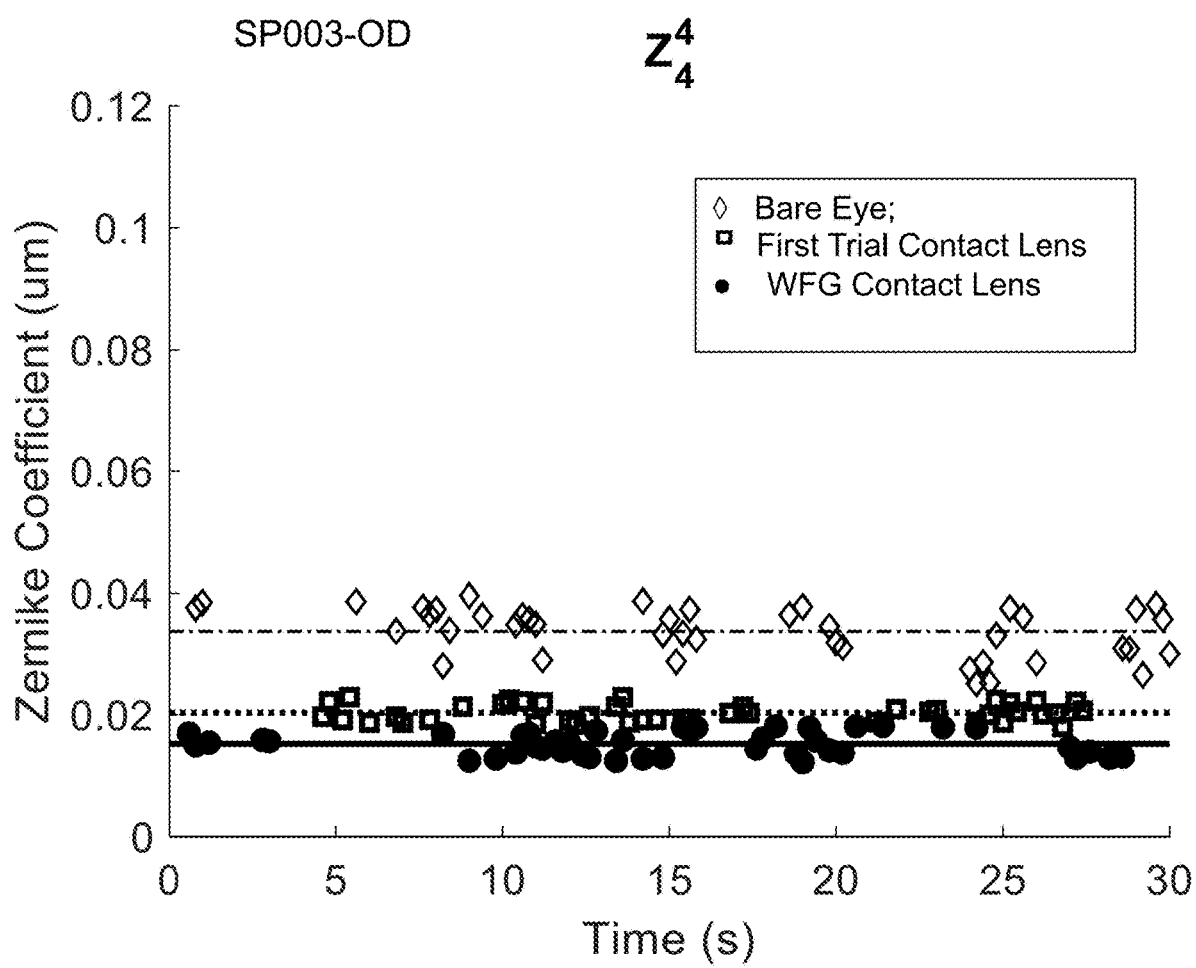
FIG. 28 shows a dynamic graph of a measured $Z_4^4$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 28 shows a dynamic graph of a measured $Z_4^4$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized CL has the lowest (best) time-averaged Zernike coefficients. The WFG customized CL has the lowest (best) time-averaged Zernike coefficients.

Figure 29:
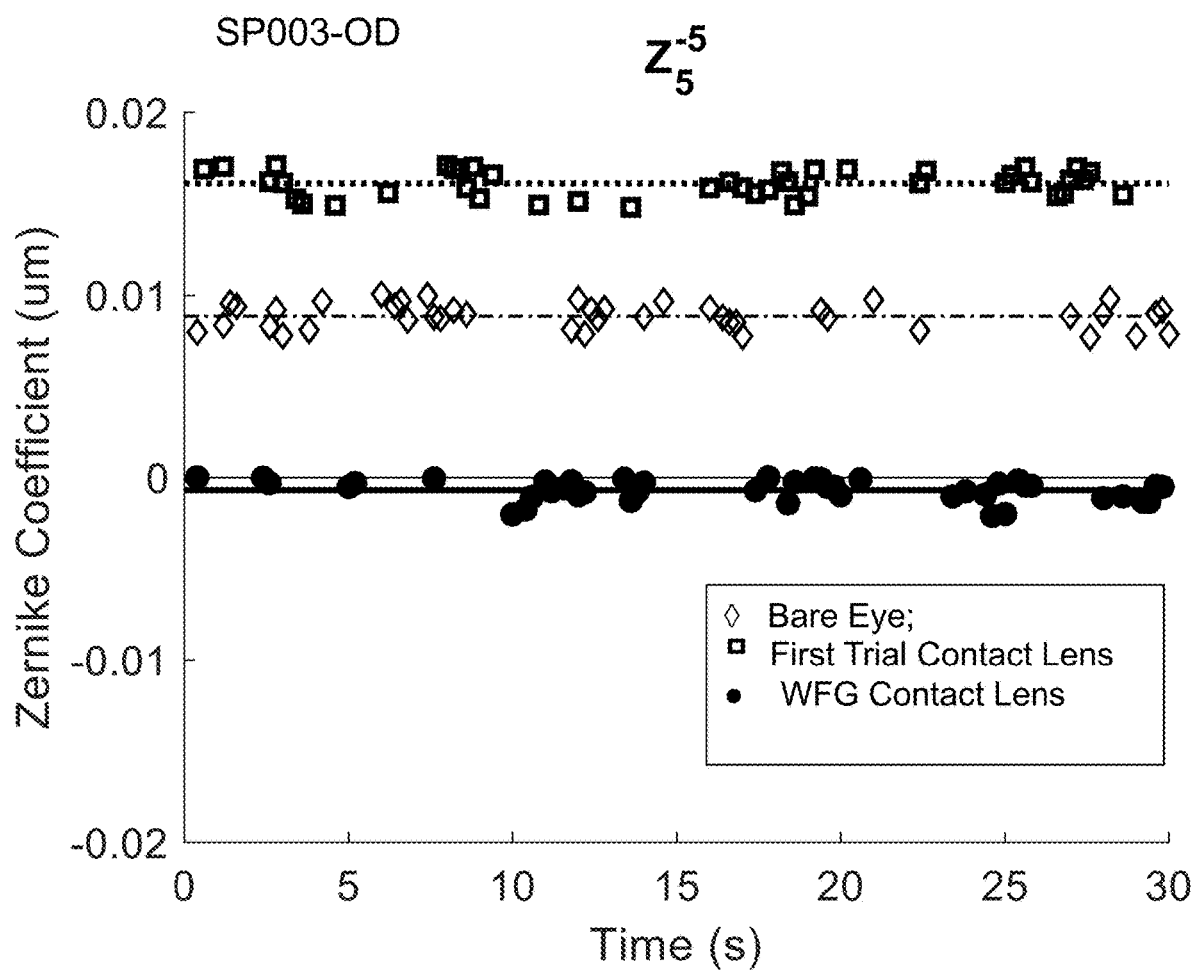
FIG. 29 shows a dynamic graph of a measured $Z_5^{-5}$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 29 shows a dynamic graph of a measured $Z_5^{-5}$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized CL has the lowest (best) time-averaged Zernike coefficients.

Figure 30:
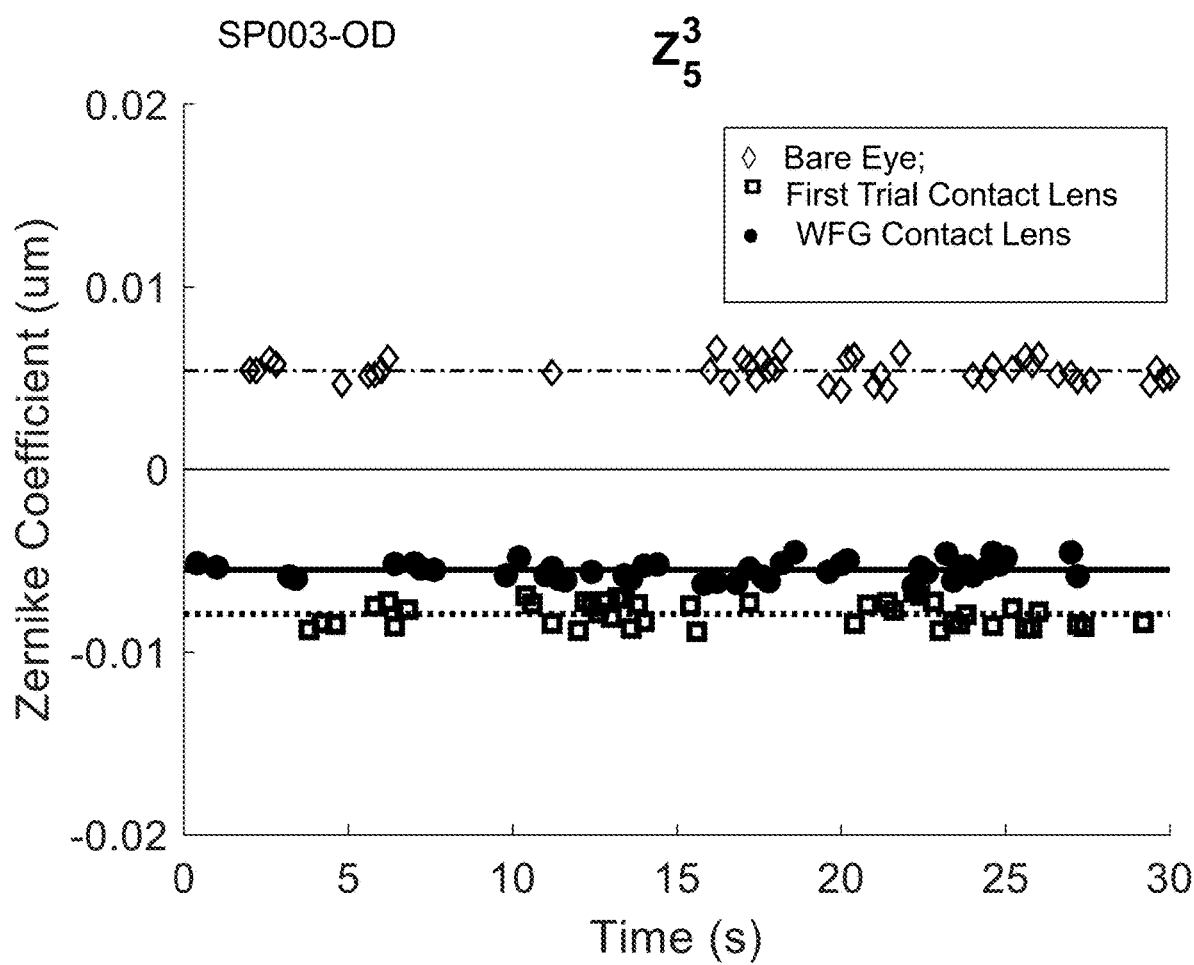
FIG. 30 shows a dynamic graph of a measured $Z_5^3$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 30 shows a dynamic graph of a measured $Z_5^3$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The bare eye and the WFG customized CL have the lowest (best) time-averaged Zernike coefficients.

Figure 31:
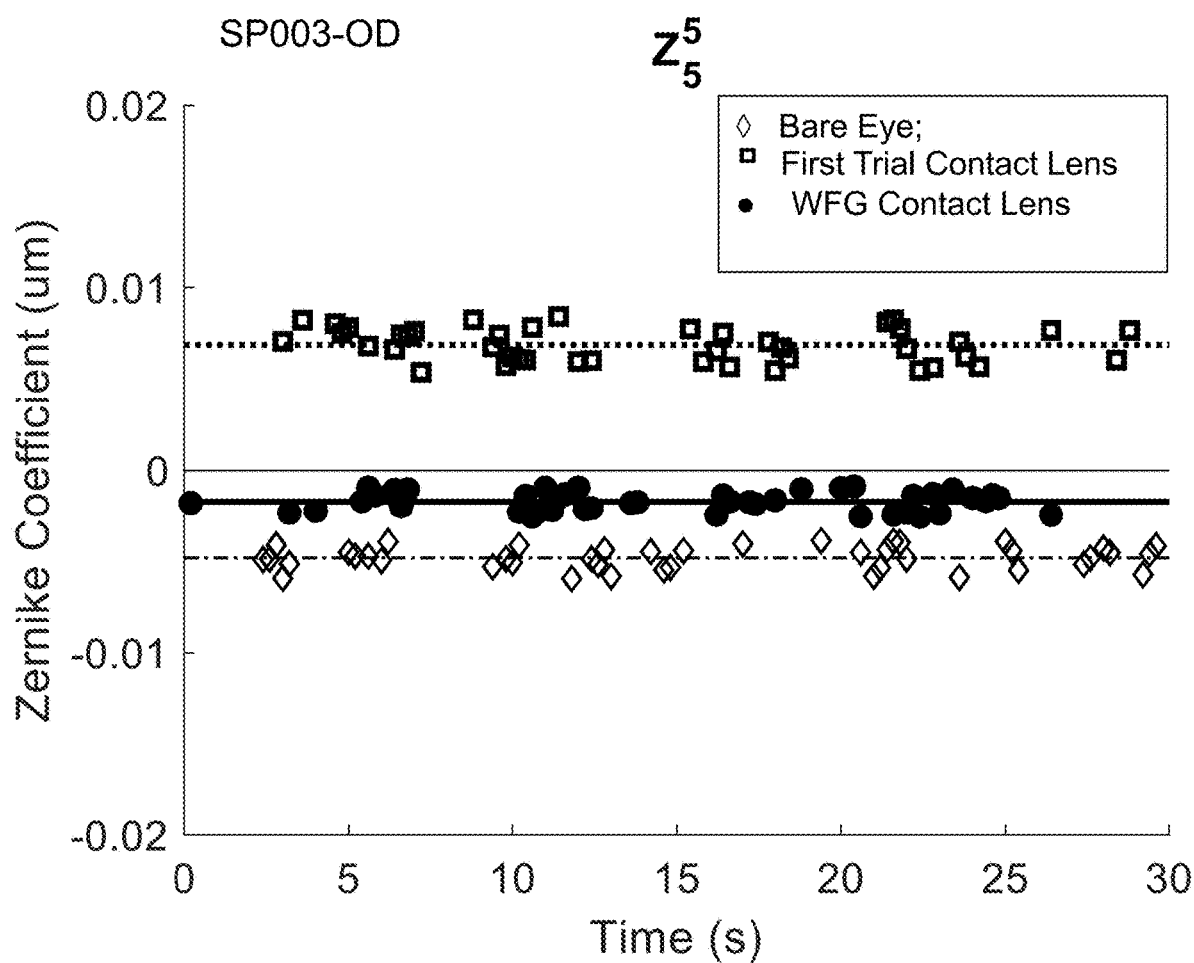
FIG. 31 shows a dynamic graph of a measured $Z_5^5$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention.

FIG. 31 shows a dynamic graph of a measured $Z_5^-$ Zernike polynomial coefficient for Patient #SP003-OD versus time, for: (1) a bare eye, (2) an eye fitted with a first trial contact lens, and (3) an eye fitted with a wavefront guided (WFG) customized contact lens, as measured by the present invention. The WFG customized CL has the lowest (best) time-averaged Zernike coefficients.

Figure 32:
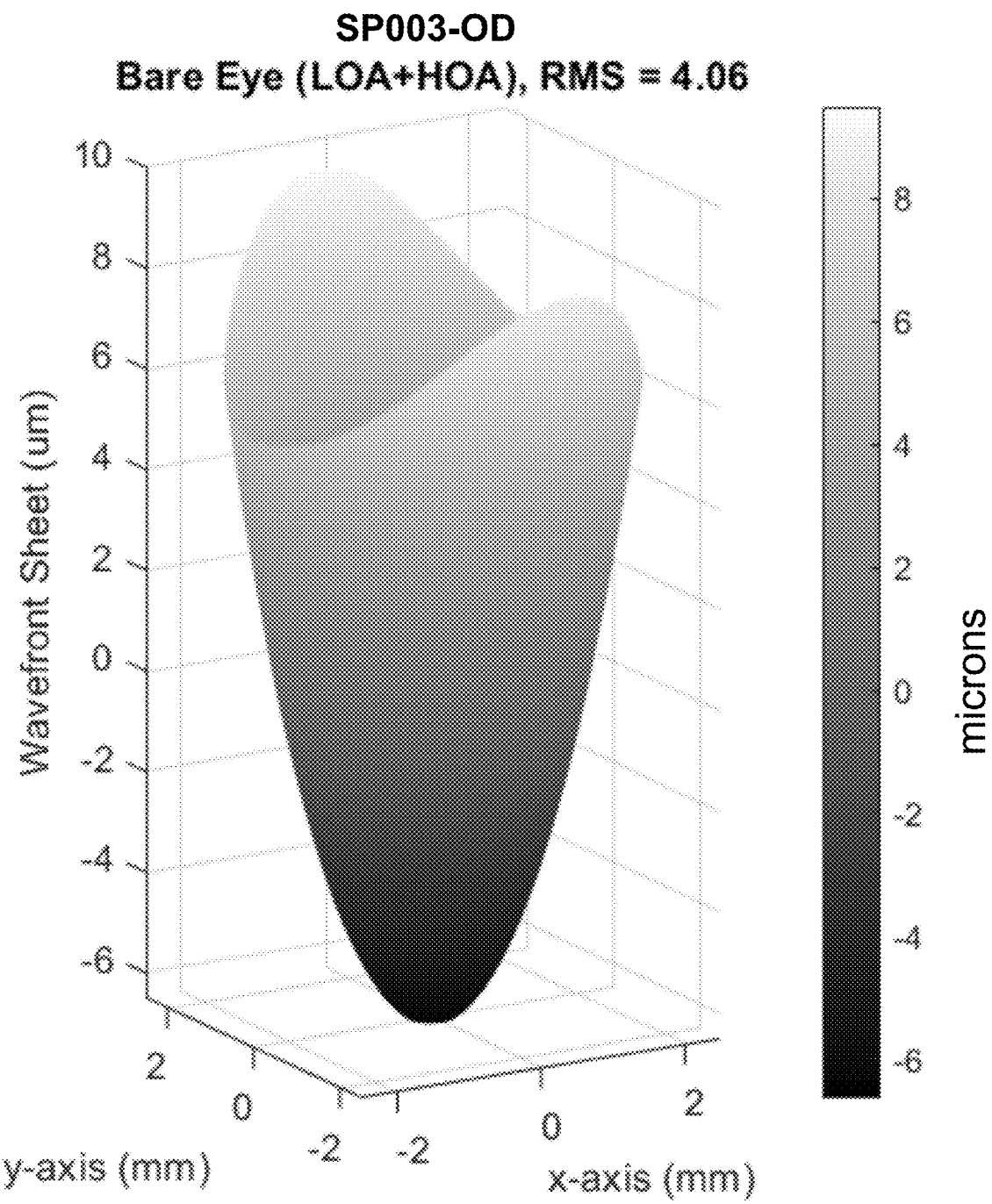
FIG. 32 shows a 3-D graph of a measured Wavefront Sheet (microns) (LOA+HOA) for Patient #SP003-OD, for a bare eye, as measured by the present invention. The total RMS=4.06. The overall level of aberrations is high for the bare eye, which is typical for an eye with myopia.

FIG. 32 shows a 3-D graph of a measured Wavefront Sheet (microns) (LOA+HOA) for Patient #SP003-OD, for a bare eye, as measured by the present invention. The total RMS=4.06. The overall level of aberrations is high for the bare eye. This is a typical amount of aberrations for an eye with myopia.

Figure 33:
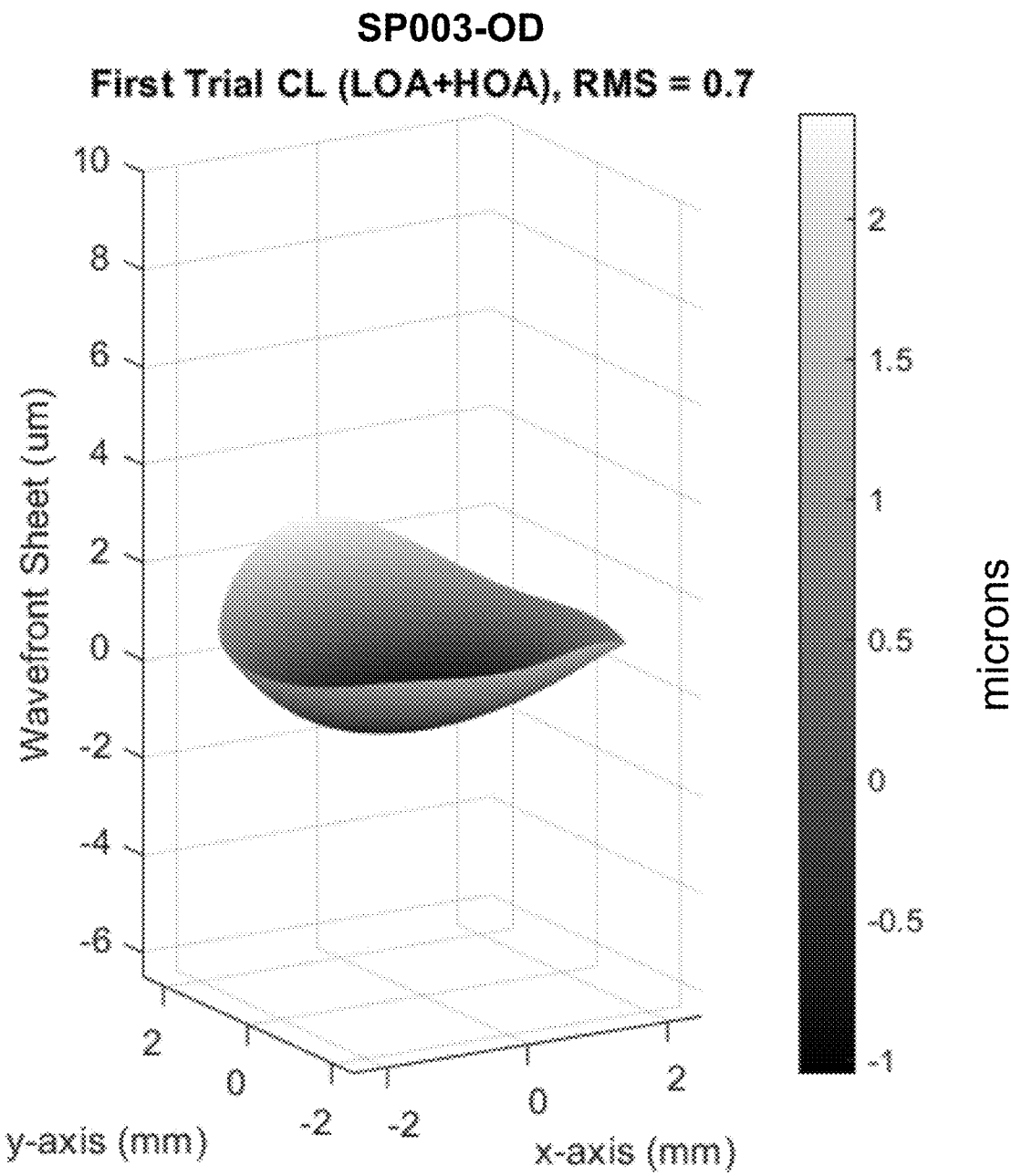
FIG. 33 shows a 3-D graph of a measured Wavefront Sheet (microns) (LOA+HOA) for Patient #SP003-OD, for an eye fitted with a first trial contact lens, as measured by the present invention. The total RMS=0.7. The overall level of aberrations is significantly reduced by fitting the eye with a first trial contact lens. The contact lens corrects for most of the refractive error, so the LOAs are reduced. However, the HOAs are not affected.

FIG. 33 shows a 3-D graph of a measured Wavefront Sheet (microns) (LOA+HOA) for Patient #SP003-OD, for an eye fitted with a first trial contact lens, as measured by the present invention. The total RMS=0.7. The overall level of aberrations is significantly reduced by fitting the eye with a first trial contact lens. The contact lens corrects for most of the refractive error, so the LOAs are reduced. However, the HOAs are not affected.

Figure 34:
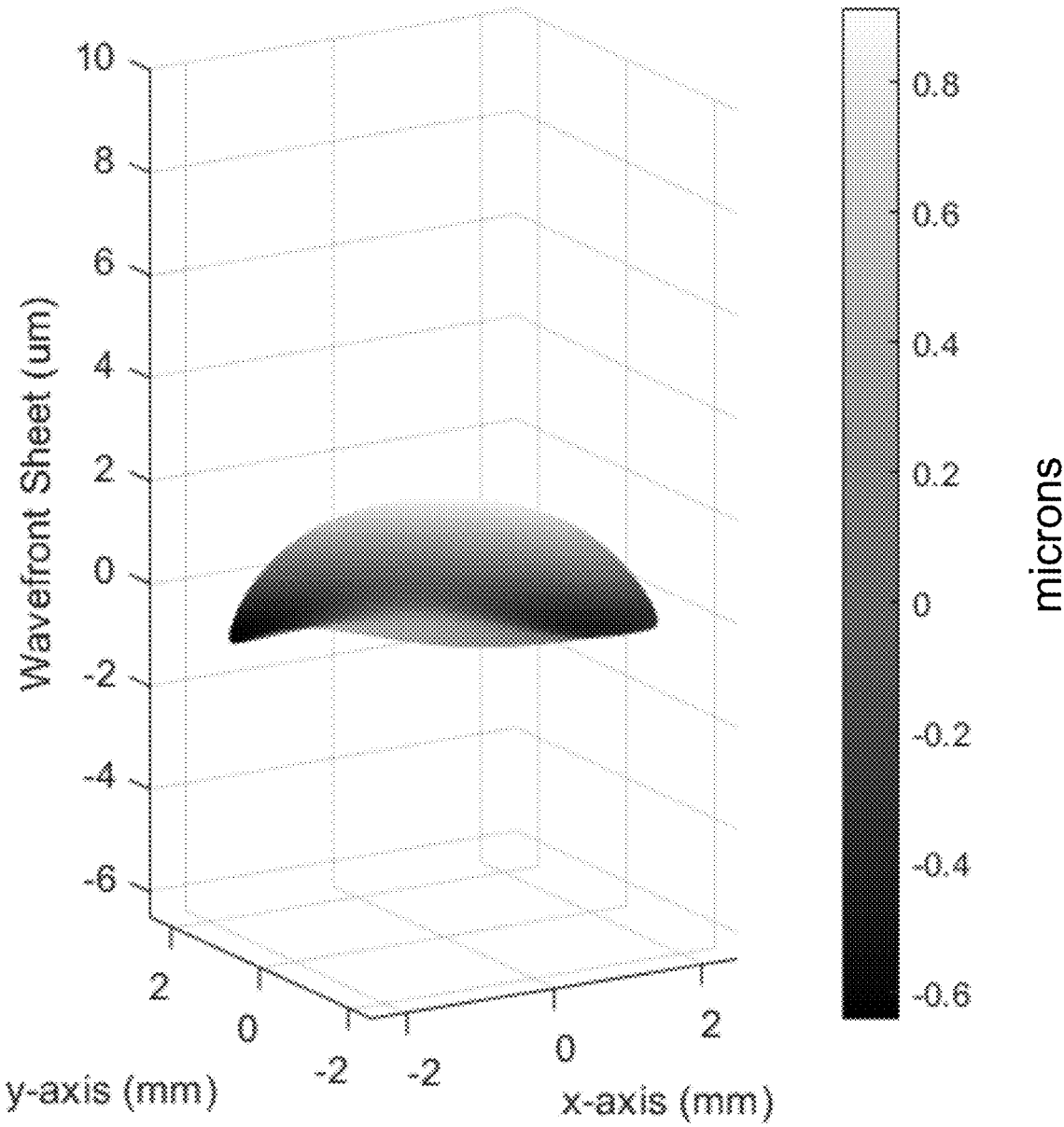
FIG. 34 shows a 3-D graph of a measured Wavefront Sheet (microns) (LOA+HOA) for Patient #SP003-OD, for an eye fitted with a Wavefront Guided (WFG) customized contact lens, as measured by the present invention.

FIG. 34 shows a 3-D graph of a measured Wavefront Sheet (microns) (LOA+HOA) for Patient #SP003-OD, for an eye fitted with a Wavefront Guided (WFG) customized contact lens, as measured by the present invention. The total RMS=0.3, which is the best (smallest) of the set of three measurements shown in FIGS. 32, 33, and 34.

Figure 35:
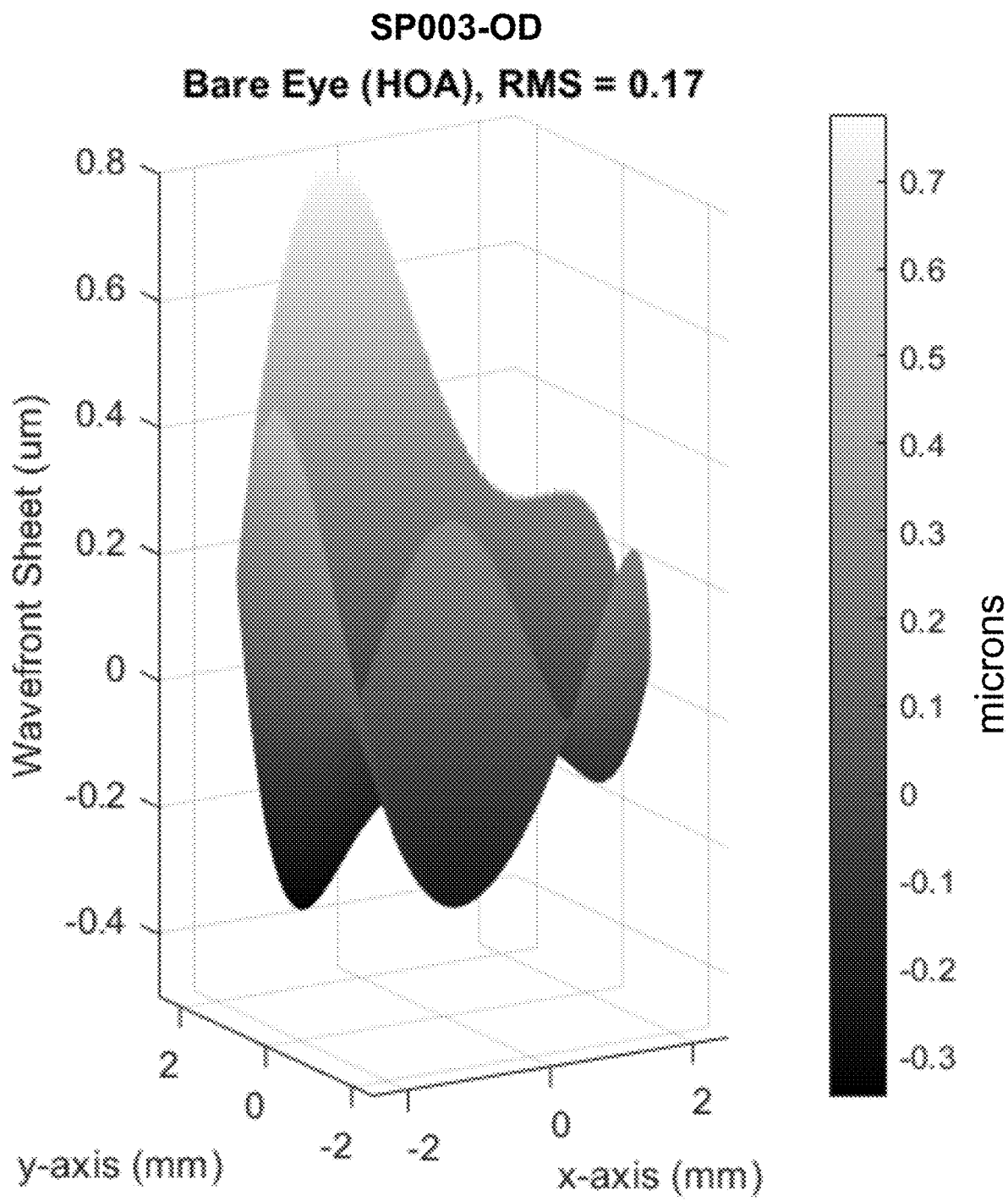
FIG. 35 shows a 3-D graph of a measured Wavefront Sheet (microns) (HOA only) for Patient #SP003-OD, for a bare eye, as measured by the present invention.

FIG. 35 shows a 3-D graph of a measured Wavefront Sheet (microns) (HOA only) for Patient #SP003-OD, for a bare eye, as measured by the present invention. The total RMS=0.19.

Figure 36:
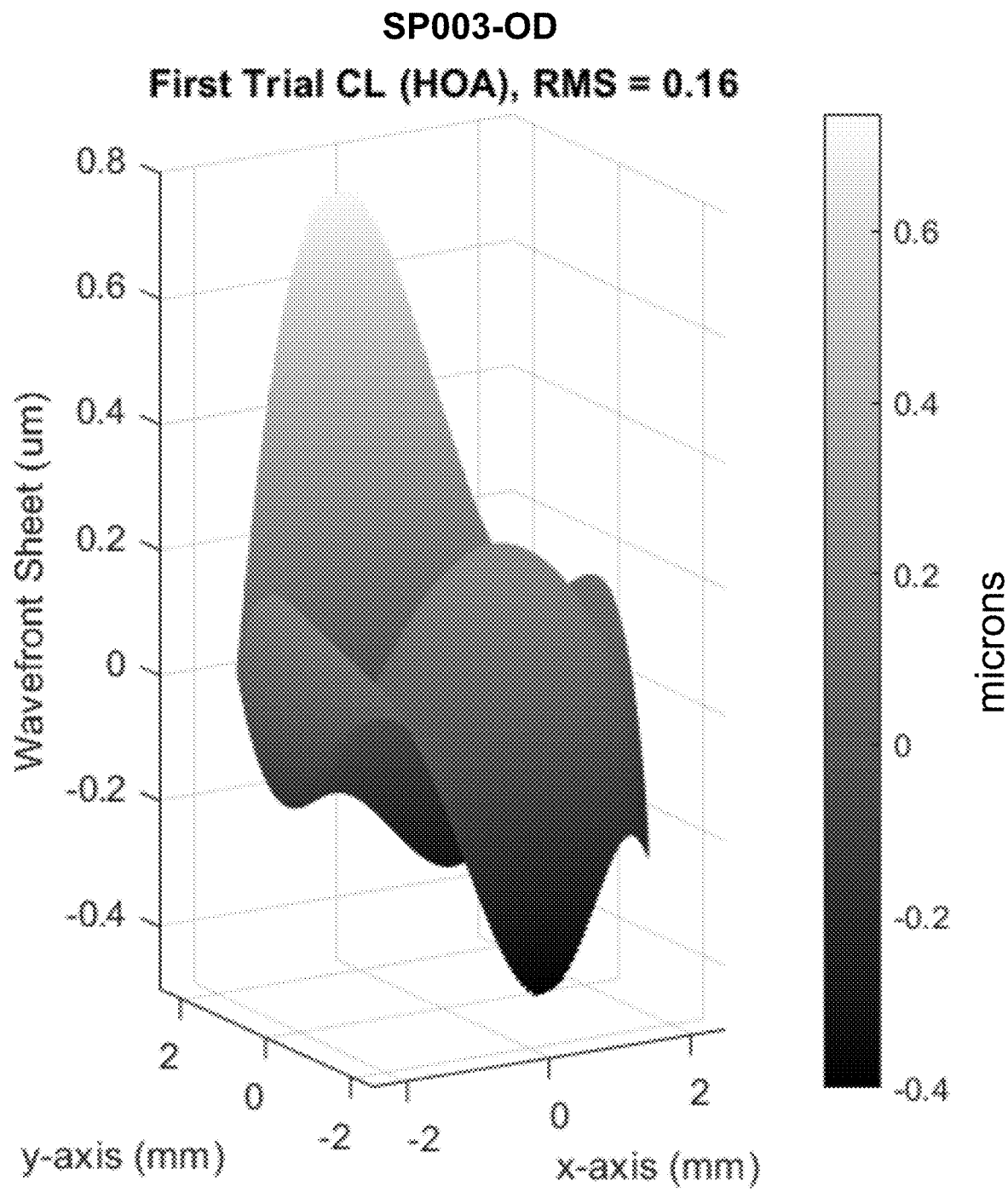
FIG. 36 shows a 3-D graph of a measured Wavefront Sheet (microns) (HOA only) for Patient #SP003-OD, for an eye fitted with a first trial contact lens, as measured by the present invention.

FIG. 36 shows a 3-D graph of a measured Wavefront Sheet (microns) (HOA only) for Patient #SP003-OD, for an eye fitted with a first trial contact lens, as measured by the present invention. The total RMS=0.16.

Figure 37:
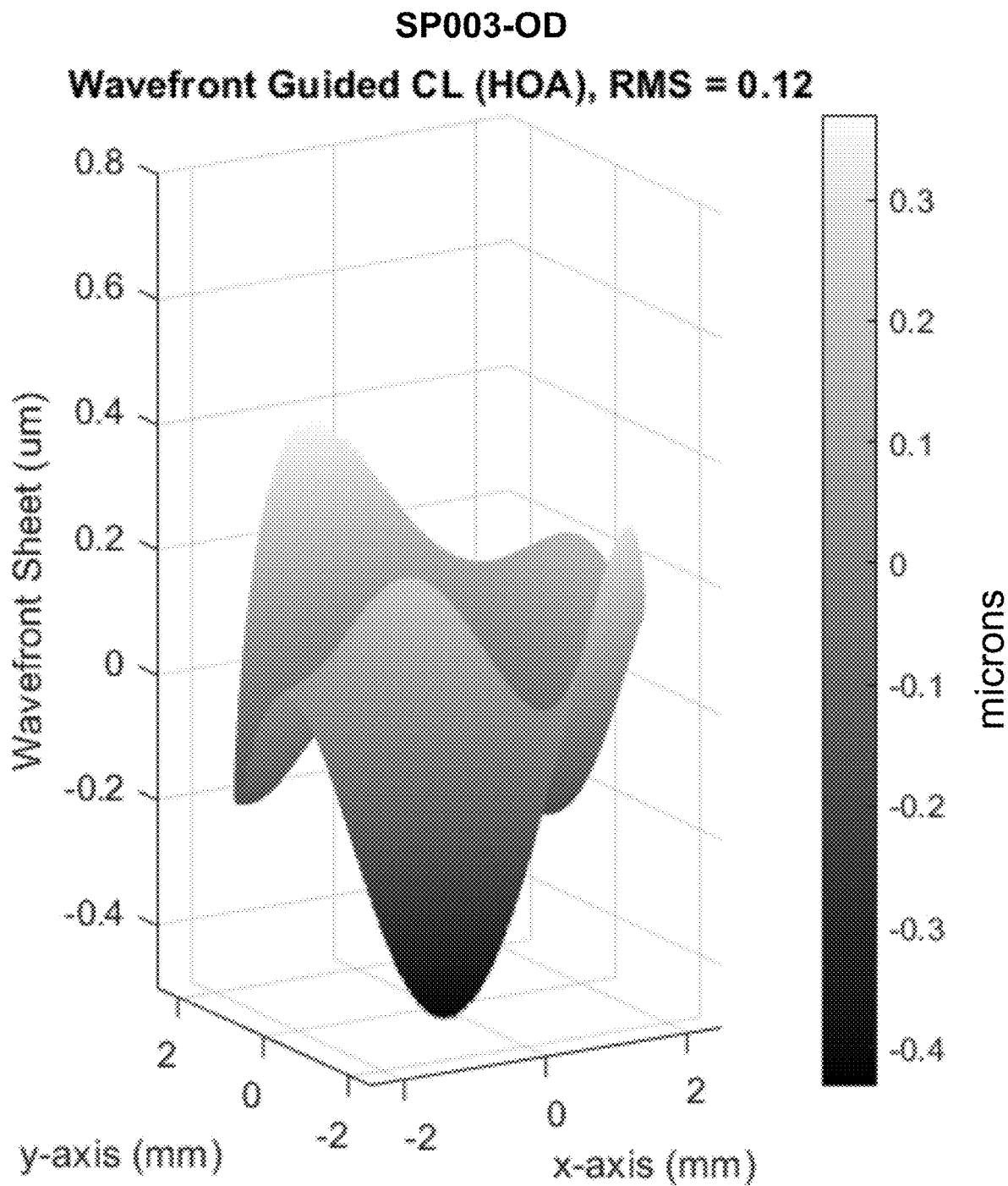
FIG. 37 shows a 3-D graph of a measured Wavefront Sheet (microns) (HOA only) for Patient #SP003-OD, for an eye fitted with a Wavefront Guided (WFG) customized contact lens, as measured by the present invention.

FIG. 37 shows a 3-D graph of a measured Wavefront Sheet (microns—HOA only) for Patient #SP003-OD, for an eye fitted with a Wavefront Guided (WFG) customized contact lens, as measured by the present invention. The total RMS=0.12, which is the smallest of the set of three measurements shown in FIGS. 35, 36, and 37.

Figure 38:
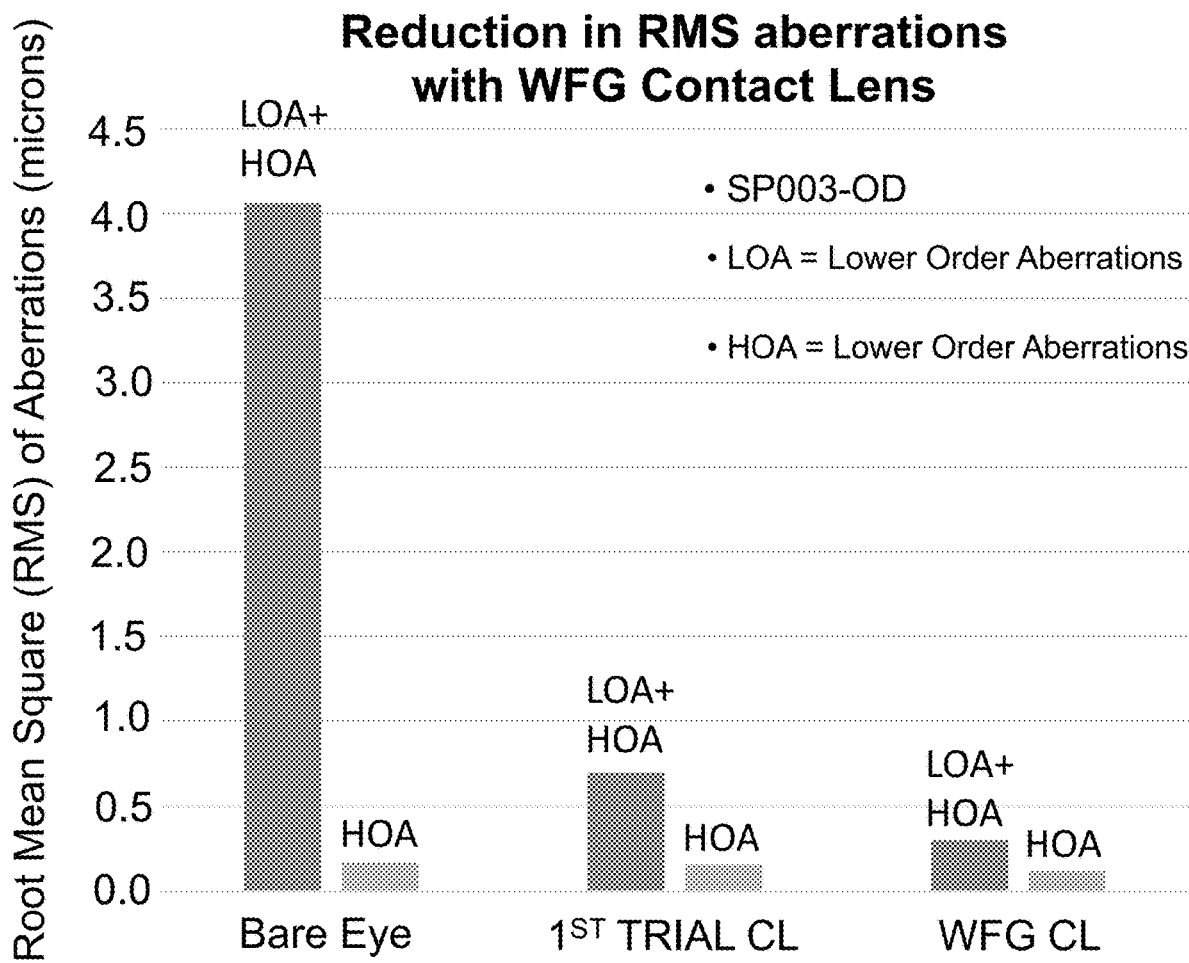
FIG. 38 shows a summary bar chart comparing RMS aberration values for (a) bare eye, (b) eye with $1^{st}$ trial contact lens, and (c) wavefront-guided customized contact lens, for both LOA+HOA aberrations and HOA aberration, according to the present invention.

FIG. 38 shows a summary bar chart comparing RMS aberration values for (a) bare eye, (b) eye with 1$^{st}$ trial contact lens, and (c) wavefront-guided customized contact lens, for both LOA+HOA aberrations and HOA aberrations, according to the present invention. There is a clear trend in improved vision (i.e., reduced RMS aberrations), with the use of a wavefront-guided customized lens (as compared to a bare eye or an eye fitted with a conventional contact lens, which have higher levels of aberrations).

Figure 39A:
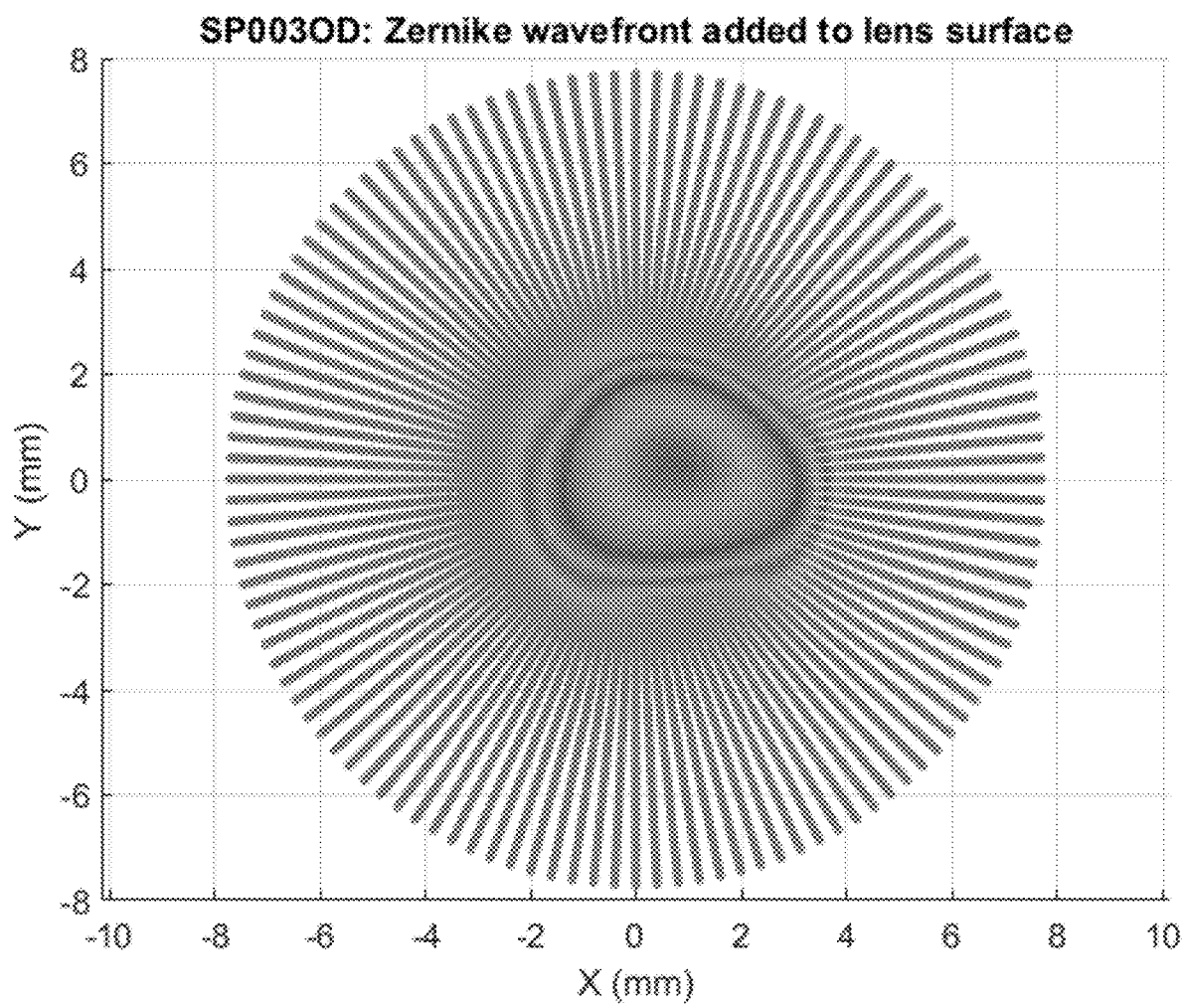
FIG. 39A shows a 2-D contour plot of a measured Zernike Wavefront (microns) for Patient #SP003-OD, for an eye fitted with a Wavefront Guided (WFG) customized contact lens (with 5 mm added to the lens surface), as measured by the present invention.

FIG. 39A shows a 2-D contour plot of a measured Zernike Wavefront (microns) for Patient #SP003-OD, for an eye fitted with a Wavefront Guided (WFG) customized contact lens (extended to the edge of the contact lens), as measured by the present invention. This is a topography map of the intended contact lens surface (front surface, also called front curve). The contact lens is 16 mm outer diameter; hence the radial lines are extended out to an 8 mm radius. Most of this surface is the original surface that includes the shape of the lens. But the wavefront patch over the optical zone has been added to improve the correction. The optical zone coincides with the location of the pupil.

Figure 39B:
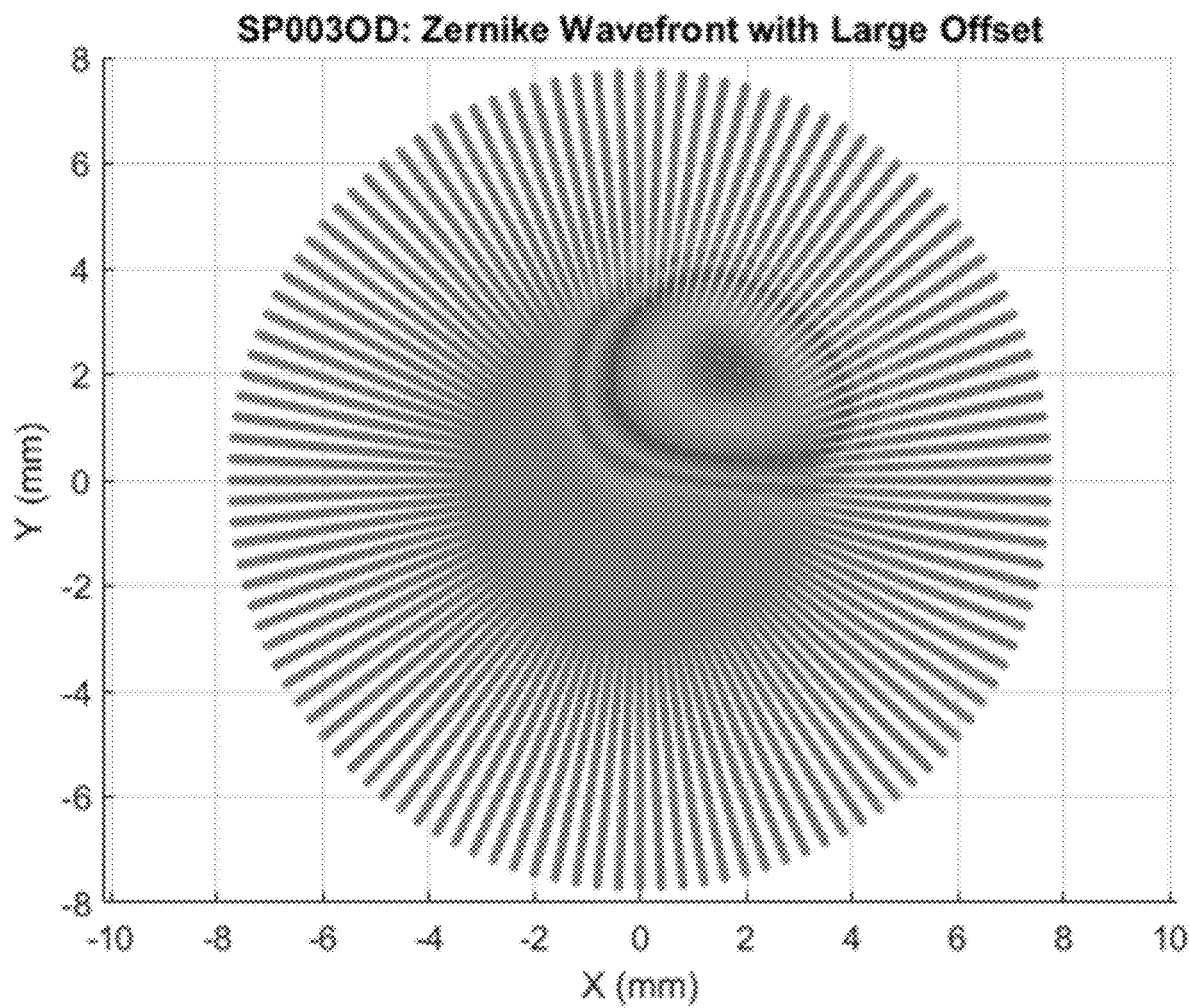
FIG. 39B shows a 2-D contour plot of a measured Zernike Wavefront (microns) for Patient #SP003-OD, for an eye fitted with a Wavefront Guided (WFG) customized contact lens (with 5 mm added radially to the lens surface), with an Offset patch, as measured by the present invention.

FIG. 39B shows a 2-D contour plot of a measured Zernike Wavefront (microns) for Patient #SP003-OD, for an eye fitted with a Wavefront Guided (WFG) customized contact lens (extended to the edge of the contact lens), with an Offset patch, as measured by the present invention.

Figure 40:
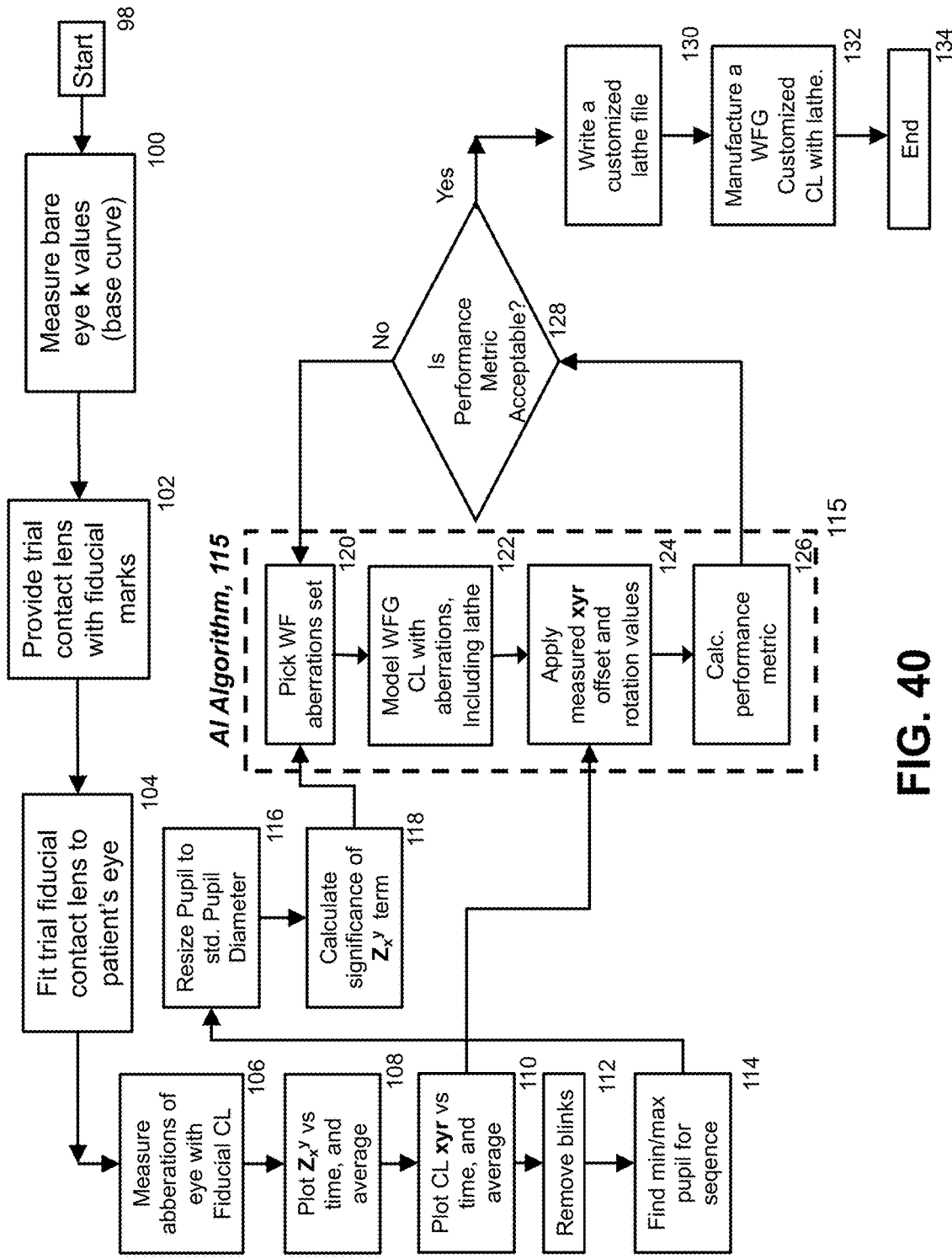
FIG. 40 shows a first example of a process flow chart for customizing a contact lens using wavefront sensor measurements, according to the present invention.

WFG Contact Lens Customization Process:

FIG. 40 shows a first embodiment of a WFG Contact Lens Customization Process flow chart, according to the present invention. The steps in this flow chart include:

Step 100—Measure k values of bare eye (k1, k2, and k2 axis: which defines the curvature of the cornea when measured on a 3 mm diameter circle) (i.e., the base curve);

Step 102—Provide trial contact lens with fiducial marks;

Step 104—Fit fiducial contact lens to patient;

Step 106—Dynamically measure WF aberrations of eye with fiducial CL;

Step 108—Calculate Zernike coefficients, $Z_x^y$, and plot them vs time, and determine time-averaged values;

Step 110—Plot CL decentrations and rotation values, xyr, vs time and determine time-averaged values;

Step 112—Remove blinks from the dynamic sequence;

Step 114—Find min/max pupil for a dynamic sequence;

Step 116—Resize to standard pupil diameter;

Step 118—Calculate significance of each $Z_x^y$ term, and delete insignificant term(s);

Step 120—Pick WF aberrations set;

Step 122—Model WFG CL with aberrations, including a lathe;

Step 124—Apply measured xyr offset, using data from step 110;

Step 126—Calculate one or more performance metric(s);

Step 128—Decide if the calculated metric is acceptable. If "No", then go back to step 120 and repeat process. If "Yes", then go to step 130;

Step 130—Write lathe file; and

Step 132—Manufacture customized contact lens with a lathe.

In step 126, the calculated performance metric(s) can include: an RMS wavefront error, a visual Strehl ratio, a predicted VA (visual acuity), or a Volume of the MTF (Modulation Transfer Function), or a weighted sum of these values. Note that step 155 in FIG. 40 refers to an Artificial Intelligence (AI) algorithm, as indicated by the dashed line box in FIG. 40. The AI algorithm 155 comprises the following steps, which can be repeated as often as needed until the design correction converges:

Step 120—Pick WF aberrations set;

Step 122—Model WFG CL with WF aberrations, including a lathe;

Step 124—Apply measured xyr offset, using data from step 110; and

Step 126—Calculate performance metric(s).

Alternatively, the algorithm in step 155 can comprise performing a least squares analysis.

In step 132, "Manufacture customized contact lens with a lathe", if the WFG contact lens is axisymmetric, then a standard machine lathe can be used. However, if the WFG correction requires an off-center Offset patch (due to CL misalignments and rotations) then the WFG customized lens will be non-axisymmetric. In this latter case, a digitallycontrolled lathe with fast Z-axis stage can be used to make the part. The advent of fast-Z-axis diamond turned lathes has enabled the construction of parts that are non-axisymmetric. As the lathe turns through the a given revolution, the tool is placed on a fast stage that can move in and out synchronized with the rotation of the part. With single point diamond turning very accurate optical surfaces can be fabricated. The lathe speed is adjusted to match the requirements for the z-motion. This is a key enabling technology for cutting lenses that include astigmatism, as the tool is required to move in and out twice per revolution. For higher order Zernike terms, the number of motions per revolution increases, but so does the magnitude of the move (generally). There are a number of companies that make such lathe tools for this kind of application and they are in common use in the ophthalmic industry. These include DAC and Sterling-Presitec, Inc.

Alternatively, for non-axisymmetric lenses, the manufacturing step (132) can comprise using a Refractive Index Writing (RIW) technique, which provides for local modification of the index of refraction. Clerio Vision [U.S. Pat. No. 10,893,936] has shown that it is possible to modify the index of refraction of various optical materials by focusing a femtosecond laser into the material. The intensity is controlled below the threshold for ablation or damage. This results in a localized spot with a locally-different index of refraction in the material. This works not only in various plastic or synthetic materials (PMMA, Acrylic, Silica Hydrogel, etc), but also in biological materials (human cornea, lens, etc).

Alternatively, for non-axisymmetric lenses, the manufacturing step (132) can comprise 3-D selective curing of liquid materials. Some contact lenses are made through UV curing of liquid materials, usually contained in a transparent mold. Since the curing of these materials is dependent on the amount of curing, the light can be controlled to control the thickness or shape of the contact lens. Using digital projection, light patterns can be precisely controlled, which allows for fabrication of custom shapes.

Alternatively, for non-axisymmetric lenses, the manufacturing step (132) can comprise additive methods (e.g., 3-D printing), which have increasingly shown promise for fabricating arbitrary surfaces. While the accuracy has typically limited this kind of application in optics, as the technology advances it is likely that this will shortly become feasible.

Alternatively, for non-axisymmetric lenses, the manufacturing step (132) can comprise adaptive molding [U.S. Pat. No. 6,830,712]. Another method for manufacturing contact lenses is through molding. Usually, molding is used to mass-produce similar shape objects. However, it is possible to make a mold where one or more surfaces are adjusted with piezo-electric or other actuators to create a desired surface profile.

Alternatively, for non-axisymmetric lenses, the manufacturing step (132) can comprise performing laser ablation (e.g., LASIK) and removing material from a base contact lens. This laser ablation technique is well-suited to manufacturing non-axisymmetric contact lenses.

Alternatively, for non-axisymmetric lenses, the manufacturing step (132) can comprise the use of a light adjustable material. By including polymers in the contact lens material that swell when exposed to light, it is possible to control the shape of the contact lens, and hence its aberration content, by selective exposure to light (usually UV). Once the desired profile is obtained, the overall material can be "locked" by uniformly exposing the entire lens.

Figure 41:
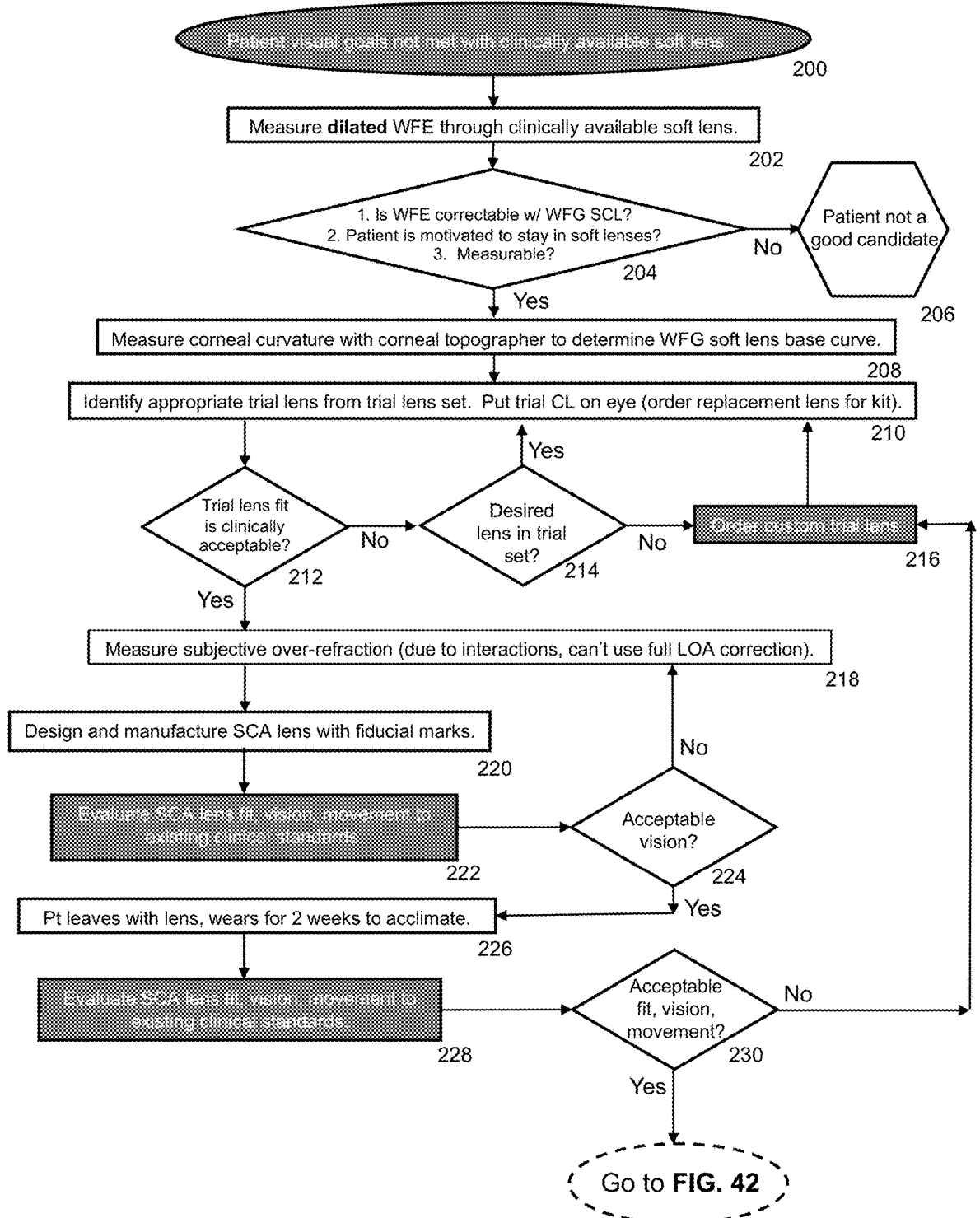
FIG. 41 shows a second example of a process flow chart for customizing a contact lens using wavefront sensor measurements, according to the present invention. The gray boxes indicate a patient encounter.
Figure 42:
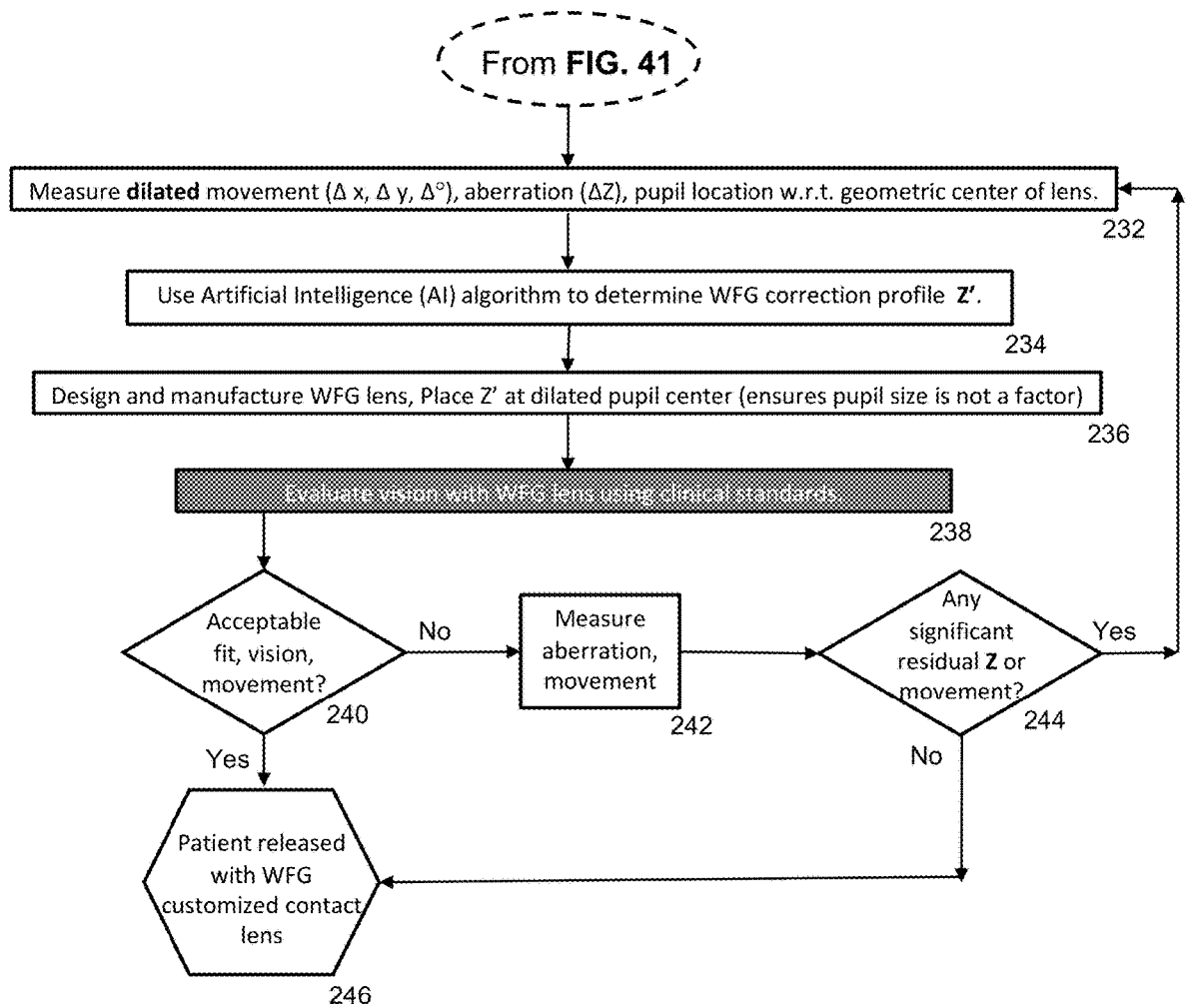
FIG. 42 shows the continuation of the process flow chart initially presented in FIG. 41, according to the present invention.

FIGS. 41 and 42 show a second embodiment of a process flow chart for Customizing a WFG Contact Lens, according to the present invention. The gray boxes (Bold text below) indicate a patient encounter has occurred or is needed. The following process steps, in sequential order, comprise:

Step 200—Patient visual goals not met with clinically available soft lens;

Step 202—Measure dilated WFE through clinically available soft lens;

Step 204—(1) Is WFE correctable w/ WFG SCL (Soft Contact Lens)?; (2) Patient is motivated to stay in soft lenses? (3) Measurable? If YES go to step 208. If NO go to step 206.

Step 206—Patient not a good candidate (STOP);

Step 208—Measure corneal curvature with corneal topographer to determine WFG soft lens base curve;

Step 210—Identify appropriate trial lens from trial lens set. Put trial CL on eye (order replacement lens for kit);

Step 212—Trial lens fit is clinically acceptable? If YES go to step 218. If NO, then go to step 214;

Step 214—Desired lens in trial set? If YES, go back to step 210. If NO, go to step 216.

Step 216—Order custom trial lens; then go to step 210;

Step 218—Measure subjective over-refraction (due to interactions, can't use full LOA correction);

Step 220—Design and manufacture SCA lens;

Step 222—Evaluate SCA lens fit, vision, movement to existing clinical standards;

Step 224—Is there acceptable vision? If YES go to step 226. If NO then go back to step 218;

Step 226—Patient leaves with lens, wears for 2 weeks to acclimate;

Step 228—Evaluate SCA lens fit, vision, movement to existing clinical standards;

Step 230—Is the fit acceptable, vision, movement OK? If YES go to 232. If NO go to 216;

Step 232—Measure dilated movement ($\Delta$ x, $\Delta$ y, $\Delta$ °), aberration (AZ), pupil location w.r.t. geometric center of lens;

Step 234—Artificial Intelligence (AI) or other algorithm determines WFG correction profile Z';

Step 236—Design and manufacture WFG lens, Place Z' at dilated pupil center (this ensures pupil size is not a factor);

Step 238—Evaluate quality of vision with WFG lens using clinical standards;

Step 240—Is the fit acceptable, vision, movement OK? If YES go to 246. If NO go to 242;

Step 242—Measure aberration, movement;

Step 244—Any significant residual Z or movement? If YES go to step 232. If NO go to step 246;

Step 246—Patient released with WFG customized contact lens.

FIG. 42 shows the continuation of the WFG customization process flow chart from FIG. 41, according to the present invention.

In all of the embodiments of the present invention, the optical devices can rapidly multiplex (i.e., cycle) between wavefront sensing and visual iris imaging. This allows the clinician to create a dynamic sequence of measurements with both wavefront sensing (WFS) and iris imaging being interleaved, allowing the clinician to find the position of the contact lens on the eye relative to the pupil, and to measure the wavefront through the contact lens simultaneously (or near simultaneously). An example of a timing sequence is shown in FIG. 19.

Figure 43A:
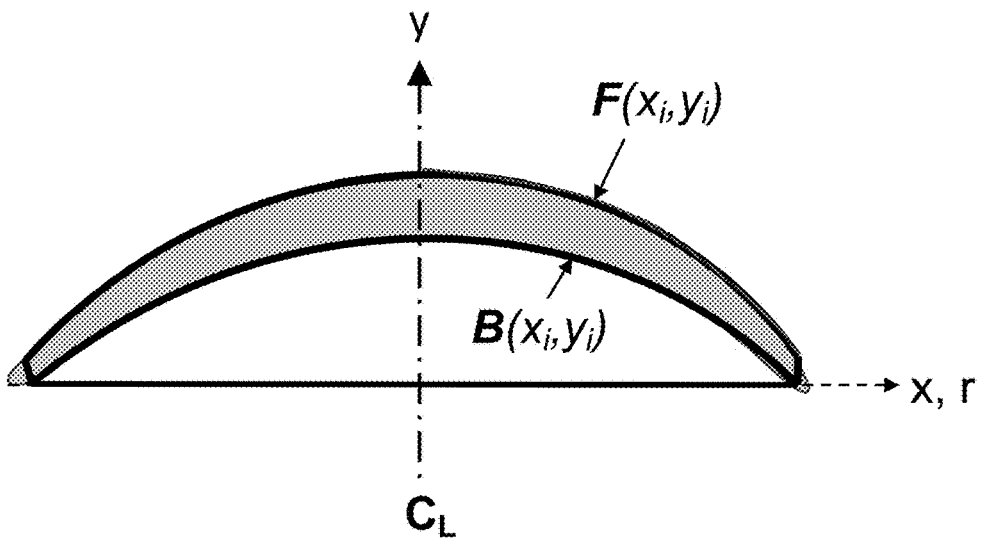
FIG. 43A shows a cross-section view of a conventional contact lens radial surface profile, with the front and back surfaces defined as $F(x_i,y_i)$ and $B(x_i,y_i)$, respectively, according to the present invention.

FIG. 43A shows a cross-section view of an example of a conventional contact lens radial surface profile, with the front and back surfaces defined as $F(x_i,y_i)$ and $B(x_i,y_i)$, respectively, according to the present invention.

Figure 43B:
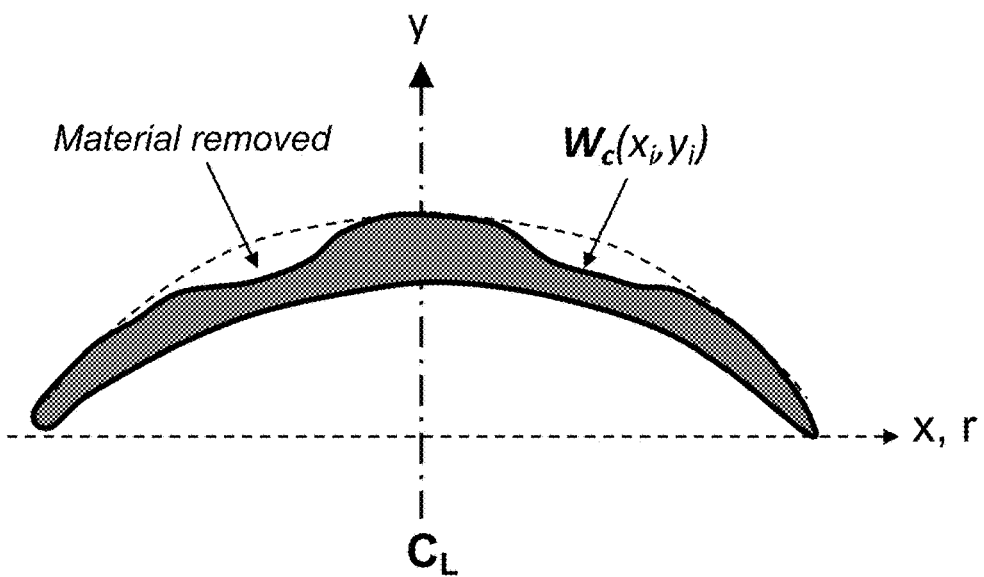
FIG. 43B shows a cross-section view of a WFG corrected contact lens radial surface profile, with the front surface defined as $W_c(x_i,y_i)$, according to the present invention.

FIG. 43B shows a cross-section view of an example of a WFG corrected contact lens radial surface profile, with the front surface (dashed line) defined as $W_c(x_i,y_i)$, according to the present invention.

Figure 44:
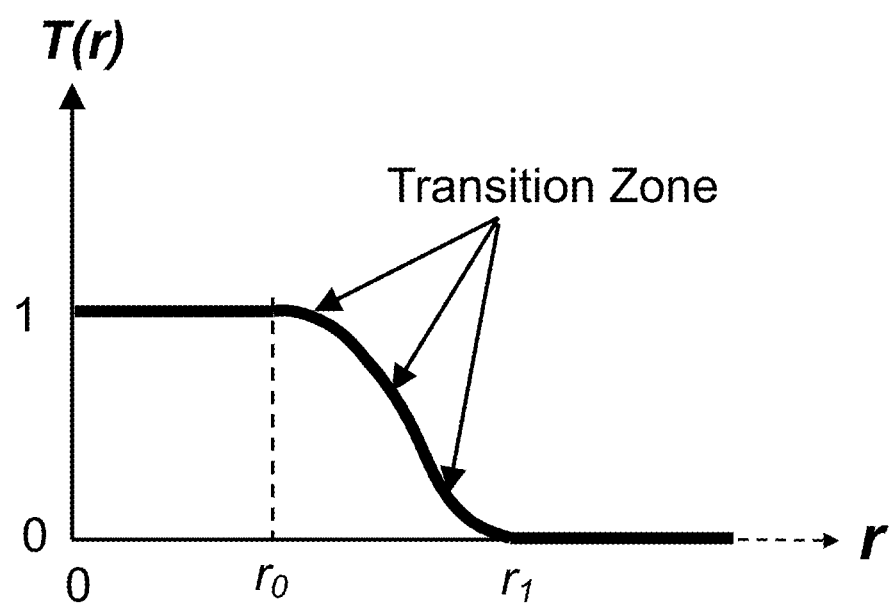
FIG. 44 shows an example of a radial profile of a Transition Zone function, $T(r)$.

FIG. 44A shows an example of a radial profile of a Transition Zone, T(r).

Figure 45A:
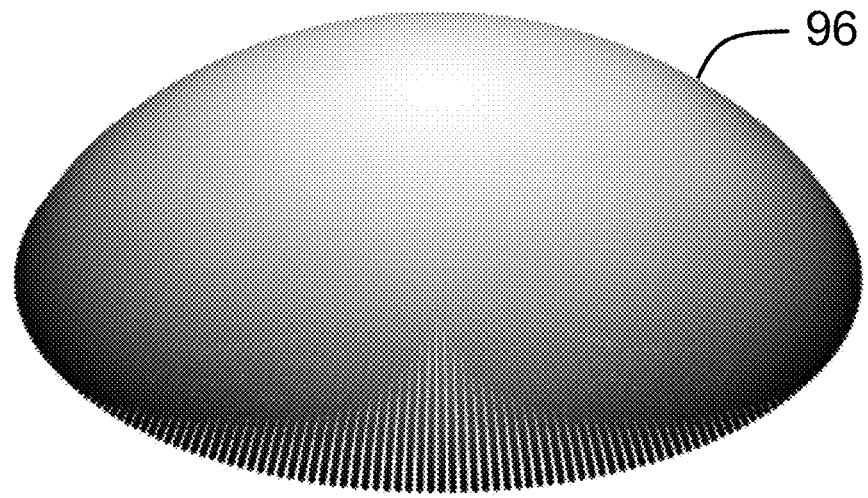
FIG. 45A shows a 3-D solid shaded image of an example of a conventional contact lens 96.

FIG. 45A shows a 3-D solid shaded image of an example of a conventional contact lens 96.

Figure 45B:
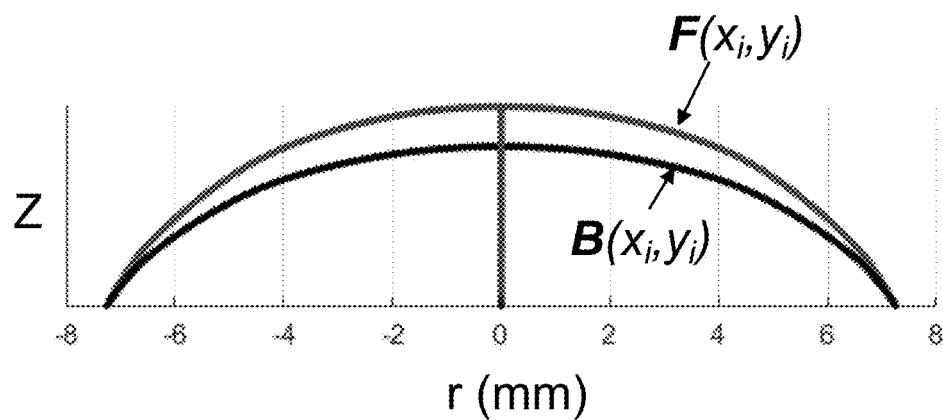
FIG. 45B shows a cross-sectional view of an example of a 2-D radial profile of the front side surface $F(x,y)$ and back side surface $B(x,y)$ of the conventional contact lens of FIG. 45A.

FIG. 45B shows a cross-sectional view of an example of a 2-D radial profile of the front side surface F(x,y) and back side surface B(x,y) of the conventional contact lens of FIG. 45A.

Figure 46A:
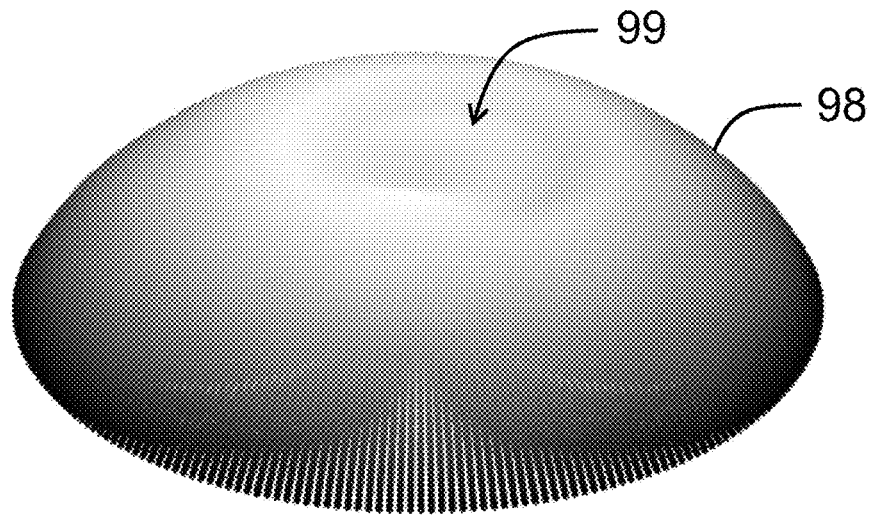
FIG. 46A shows a 3-D solid shaded image of an example of a WaveFront Guided (WFG) customized contact lens 98 with an Offset 99 on the front surface, which corrects for higher order aberrations.

FIG. 46A shows a 3-D solid shaded image of an example of a WaveFront Guided (WFG) customized contact lens 98 with an Offset 99 on the front surface, which corrects for higher order aberrations.

Figure 46B:
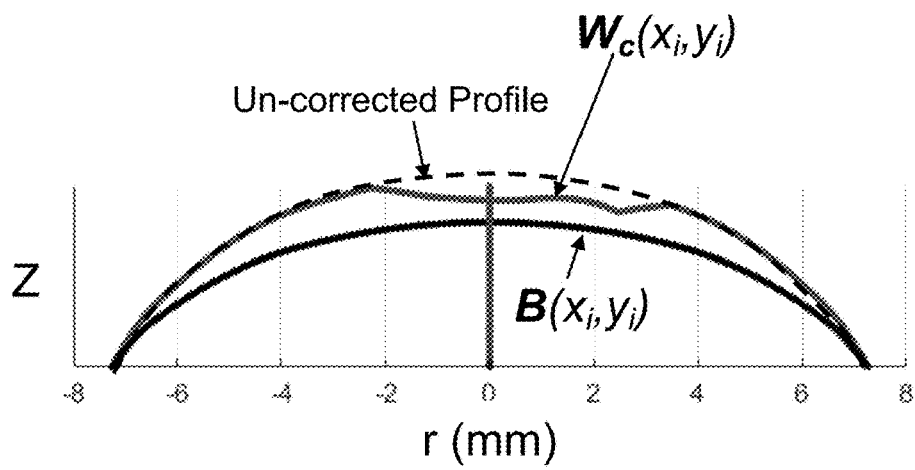
FIG. 46B shows a cross-sectional view of an example of a 2-D radial profile of the wavefront-corrected front side surface $W_c(x,y)$ and back side surface $B(x,y)$ of the WFG customized contact lens of FIG. 46A.

FIG. 46B shows a cross-sectional view of an example of a 2-D radial profile of the wavefront-corrected front side surface $W_c(x,y)$ and back side surface B(x,y) of the WFG customized contact lens of FIG. 47A. A transition zone is identified between r=2 mm and r=3 mm, as well as the Offset patch in the front surface profile. The transition zone is used to smooth the transition from the optical zone to the outer zone of the contact lens.

Figure 47:
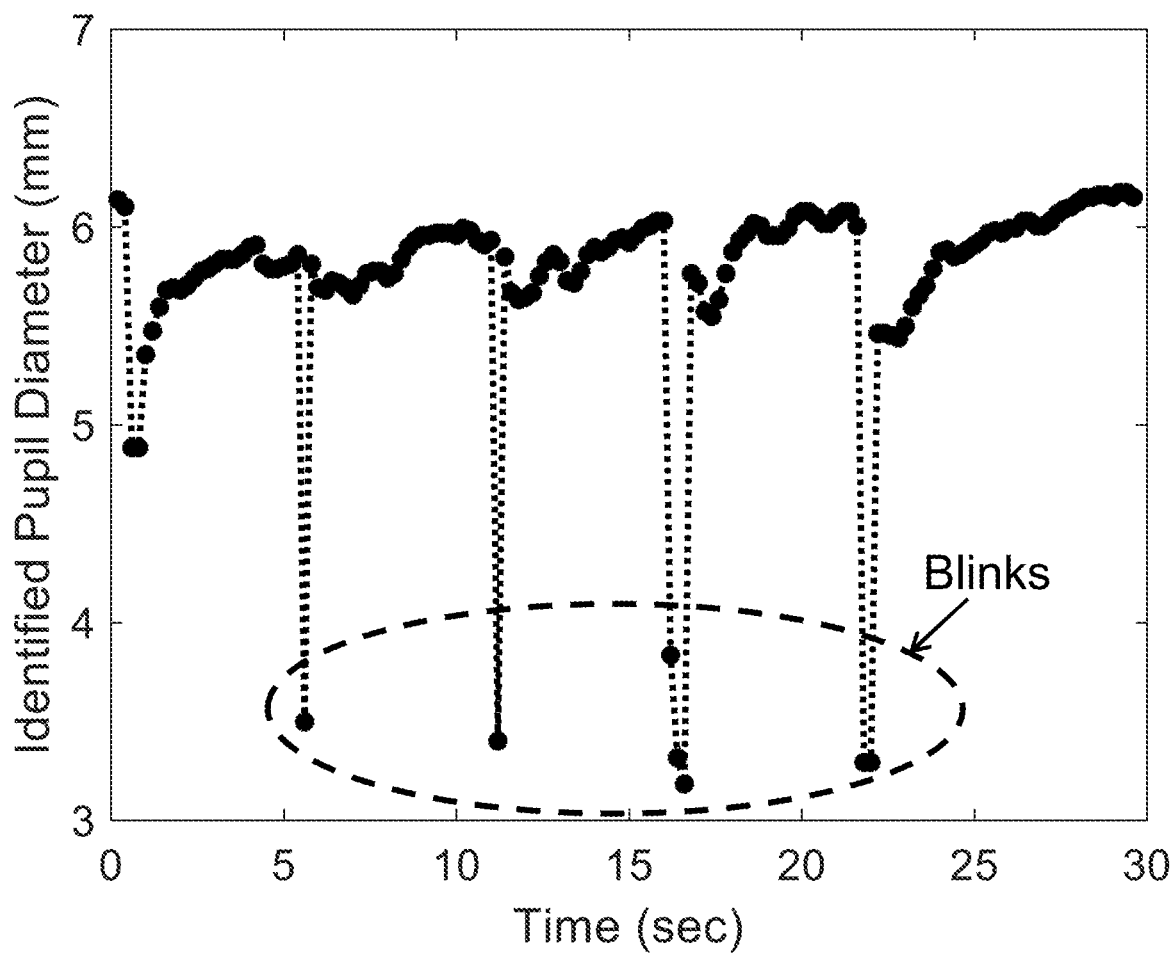
FIG. 47 shows an example plot of measured pupil diameter (mm) versus time, showing outlying points caused by blinks.

FIG. 47 shows an example plot of measured pupil diameter (mm) versus time, showing outlying points caused by blinks. These outlying points can be dropped by the software program, because the outlying points causes the pupil diameters to be underestimated when all of the data is time-averaged together as a set.

FIG. 48A shows a dynamic measurement of the spherical equivalent and the pupil's radius of a patient's eye, according to the present invention. These two parameters are indicative of the state of accommodation of the subject's eye. In this case, the 22 year-old female showed some small fluctuations in both the pupil size and in the measured spherical equivalent.

FIG. 48B shows a dynamic measurement of the spherical equivalent and the pupil's radius of a patient's eye, according to the present invention. The data from FIG. 48A presented again with an expanded scale shows that the spherical equivalent fluctuates during the measurement process, as does the pupil size. The correct "far-point" or distance refraction is for those points when the pupil size is largest, and the spherical equivalent is highest (most positive). Thus, recording these two parameters as a function of time can aid in determining the correct distance refraction and help eliminate instrument accommodation.

Figure 49:
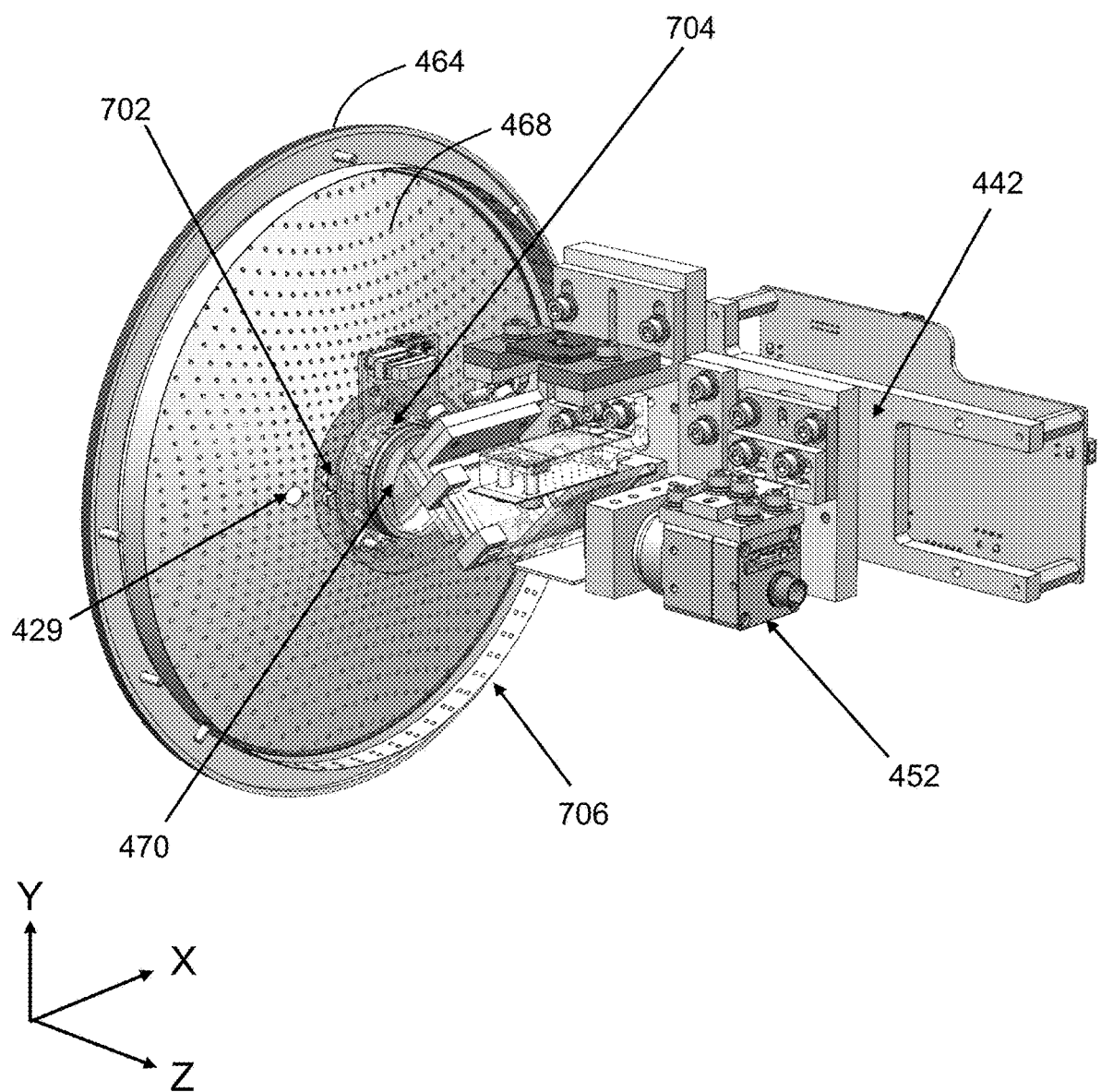
FIG. 49 shows a perspective view of the internal components of a NextWave™ aberrometer optical instrument, with the covers off, according to the present invention.

FIG. 49 shows a perspective view of the internal components of a NextWave™ aberrometer optical instrument, with the covers off, according to the present invention. Topographer cone 464 with conically-oriented holes 468 comprises a central rectangular aperture (18 mm×24 mm); a through-hole 429 for passing light from the eye to a range finder camera (not shown); a ring of LED lights 706 disposed around the outer circumference of the topographer cone 464; six LEDs 702 protruding through the front of the cone and oriented at the patient's eye; and back illuminating LEDs 704 for "flat" front of cone coverage. Wavefront sensor 452 is mounted to primary optics plate 442.

Figure 50:
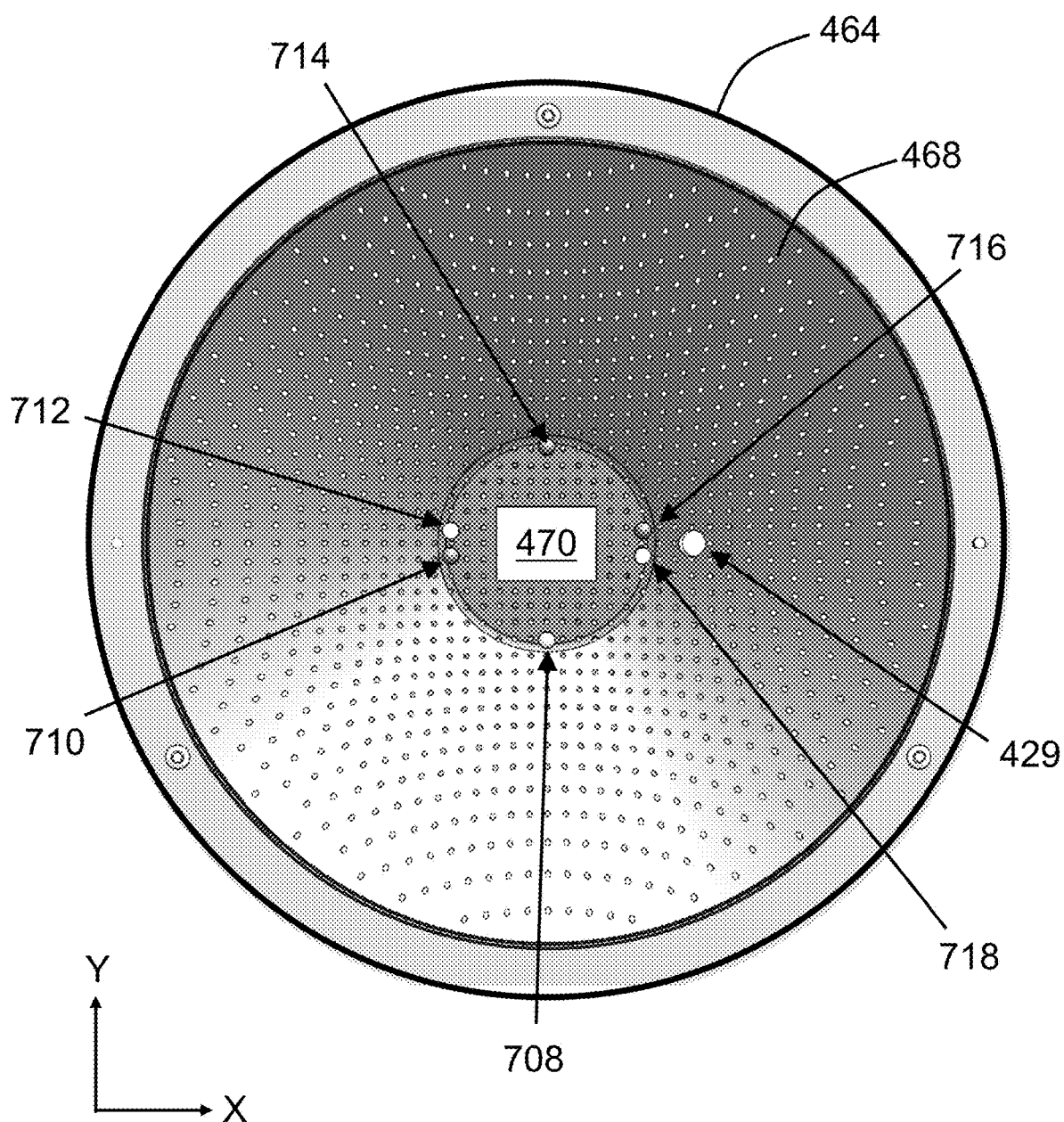
FIG. 50 shows a front elevation view of the internal components of a NextWave™ aberrometer optical instrument, with the covers off, according to the present invention.

FIG. 50 shows a front elevation view of the internal components of a NextWave™ aberrometer optical instrument, with the covers off, according to the present invention. Topographer cone 464 with conically-oriented holes 468 comprises a central rectangular aperture (18 mm×24 mm); a through-hole 429 for passing light from the eye to a range finder camera (not shown). LED 708 is a 555 nm visible LED; LED 710 is a 760 nm IR LED; LED 712 is a 930 nm IR LED; LED 714 is a 680 nm visible LED; LED 716 is a 760 nm IR LED; and LED 718 is a 930 nm IR LED. The 555 nm LED is green. It is used to constrict the pupil of the eye. The 760 nm LEDs are used to show an image of the eye with detail of the iris structures. Patients can barely see the 760 nm light, which may be slightly distracting to the patient. Detail in the iris can be used to show the rotational state of the eye, but when the iris is fully dilated (as might happen during a measurement) it can be hard to find details in the iris to find landmarks for rotation (cyclotorsion is the word usually used to describe the fact that the eye can rotate (clock) a little bit around the line of sight of the eye). The 930 nm LEDs are used to show an image of the eye. Detail of the iris is poor at this wavelength, but patients cannot see the 930 nm wavelength, so it is a good wavelength to use while the instrument is being aligned to the eye. The 680 nm LED is used to show scleral blood veins. Those can be useful for defining a rotational state of the eye. Light at a wavelength of 680 nm is usually considered to be visible, although just barely.

Figure 54:
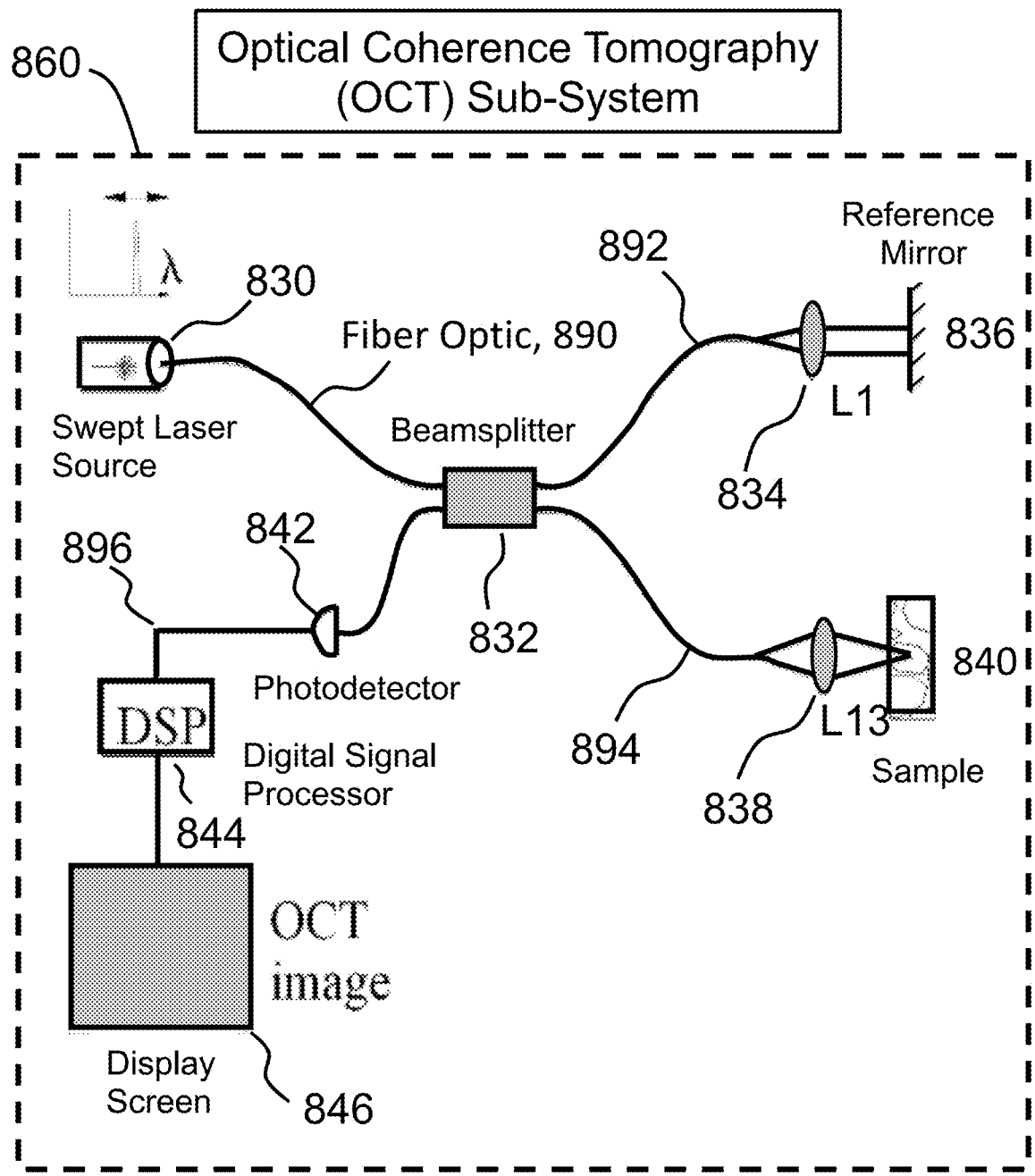
FIG. 54 shows a schematic optical layout of an OCT sub-system.

FIG. 54 shows a schematic optical layout of an OCT sub-system. The OCT-subsystem 860 connects into the Aberrometer of FIG. 2 by pointing the light coming out of the lens L13 towards the beamsplitter BS4. Light reflects off BS4 and BS3, then goes through BS2, BS1, L1 and QWP, then travels to the eye located at the object plane, then scatters back through, QWP, L1, BS1, BS2, reflects off BS3 and BS4, then re-enters the OCT-subsystem through the lens L13. The OCT sub-system in FIG. 54 comprises: a swept laser source 830 (with variable wavelengths) with X-Y scanning and high-speed data acquisition. The breadboard 860 can be used to verify the required signal-to-noise needed to detect internal structures reliably and to verify the required optical power and detection efficiency. It will also allow testing of various scan profiles and IOL detection algorithms. The acronyms used in FIG. 54 stand for the following: SS is a swept source 830, referring to a laser that scans in wavelength instead of time; PD is a photo detector 842; BS is a beam splitting fiber coupler 832; DSP is a digital signal processor 844; REF is a mirror 836 that provides a reference signal by reflecting light back into the fiber optic cable; and SMP is the sample region 840. The SS laser 830 launches light into a fiber optic cable 890. The beamsplitter 832 sends some light to the REF mirror 36 and some light to the SMP sample 840. Some light reflects off the REF mirror 836, through the BS 832, and then onto the PD photodetector 842. Some light scatters off the different layers in the SMP sample 840, goes back into the fiber 894, back through the BS 832, and onto the photodetector 842. Over a period of about a millisecond, the SS laser 830 sweeps through a range of wavelengths. As it does, the signal on the photodetector varies rapidly with time. The cause is that light from the REF mirror 836 and the SMP sample 840 is either constructively or destructively interfering. The DSP digital signal processor 844 analyzes the time series data using Fourier transforms techniques and converts the signal into a depth map of where there are scattering structures. This is a depth map over a single line through the sample. If the sample is moved across the beam, a cross sectional image can be created by the DSP 844 in conjunction with a recording device. The results can be displayed on a display screen 846.

The wavefront sensor can be a pyramid wavefront sensor. The fixation target can be compensated for subject astigmatism and defocus. The instrument can include a range-finder camera mounted at an angle to the instrument's optical axis to provide triangulation information for determining a distance from the eye to the instrument. The corneal topography can use full-gradient topography. A large field-of-view objective lens can be used to obtain eye images. Measured contact lens misalignment information can be analyzed statistically and presented graphically to an operator. The customized contact lens can be fabricated of silica hydrogel. The customized contact lens can be fabricated in a dry state and then hydrated. The customized contact lens can be fabricated from a polymer using cryogenic milling. A WFG customized contact lens can be created by laser-induced index of refraction patterning.

A topography of the anterior surface of the eye can be measured by the steps of:
(1) Providing an eye with fluorescein dye;
(2) Projecting a pattern of blue light onto the eye;
(3) Imaging the resulting fluorescence of the eye with a first imaging camera;
(4) Imaging the eye with a second camera arranged at an angle to the axis of the first camera; and
(5) Analyzing the resulting images to determine 3D topography of the anterior eye surface.

Any astigmatism can be compensated for by using electromechanically controlled cross-cylinder lenses in the aberrometer instrument. Fogging of a video display target can be controlled by electromechanically adjusting a position of the video target relative to a lens. Making subjective refraction measurements can use astigmatism and defocus controls. All of the dynamic measurements are obtained near simultaneously in a rapid sequence. The measurements can be recorded while changing the fixation target vergence in a sequence and then analyzed to determine subject's distance vision, and accommodation range. Fiducial marks on a contact lens are automatically located using image processing software.

We claim:

1. An instrument for dynamically measuring one or more optical parameters of a subject's eye, the instrument comprising:
   (a) a primary optical path, pointing towards the subject's eye, having a Z-axis that is coincident with the primary optical path;
   (b) a dynamically-adjustable video fixation target, aligned along the primary optical path, which is configured to compensate for astigmatism and defocus of the subject's eye;
   (c) a wavefront sensor, aligned along the primary optical path, and configured to dynamically measure wavefront aberrations of the subject's eye;
   (d) a movable Badal stage, having a first Z-axis position, which is movable along the primary optical path; and
   (e) a movable electromechanical stage, having a second Z-axis position, which is mounted to the movable Badal stage;
   wherein the wavefront sensor is attached to the movable Badal stage;
   wherein the dynamically-adjustable video fixation target is moveably attached to the movable electromechanical stage; and
   wherein the movable electromechanical stage is configured to move the dynamically-adjustable video fixation target along the primary optical path independently from any motion of the movable Badal stage along the primary optical path.

2. The instrument of claim 1, further comprising:
   optical means for projecting light onto a retina of the subject's eye; and
   imaging means for imaging light scattered from the retina onto the wavefront sensor.

3. The instrument of claim 1, wherein the wavefront sensor is a Shack-Hartmann wavefront sensor or a pyramid wavefront sensor.

4. The instrument of claim 1, further comprising a pair of electromechanically-controlled, independently-rotatable cylindrical lenses having equal and opposite power.

5. The instrument of claim 1, further comprising
   a corneal topographer; and
   an iris camera;
   wherein the wavefront sensor, the corneal topographer, and the iris camera are all mounted on an adjustable electromechanical subject alignment stage on the instrument.

6. The instrument of claim 1, further comprising:
   a range-finder camera mounted at an off-axis angle measured relative to the Z-axis of the primary optical path of the instrument;
   wherein the range-finder camera points towards a cornea of the subject's eye; and
   wherein the range-finder camera is configured to provide triangulation information useful for determining a Z-axis distance along the primary optical path from the cornea of the subject's eye to the instrument.

7. The instrument of claim 1,
   wherein the dynamically-adjustable video fixation target is configured to project one or more images towards the subject's eye; and
   wherein the one or more images is selected from a group consisting of:
   (a) an eye chart;
   (b) one or more individual letter(s);
   (c) one or more geometric patterns;
   (d) one or more scenic targets; or
   (e) one or more movie loops or moving GIFs; and/or
   (f) combinations thereof.

8. The instrument of claim 1, further comprising:
   (a) a recorder configured to dynamically record the one or more optical parameters of the subject's eye;
   (b) adjustment means for dynamically changing a vergence of the dynamically-adjustable video fixation target; and
   (c) a computer configured to dynamically analyze the one or more optical parameters of the subject's eye to determine a distance vision and an accommodation range of the subject's eye.

9. The instrument of claim 1, further comprising:
   (a) an iris camera light path;
   (b) a corneal topographer light path;
   (c) a Helmholtz light path;
   (d) a wavefront sensor light path;
   (e) a probe beam light path;
   (f) a video fixation target light path; and
   (g) a range-finder camera light path; and
   wherein the range-finder camera light path points towards a cornea of the subject's eye at an off-axis angle measured relative to the Z-axis, for triangulating a Z-axis distance from a cornea of the subject's eye to the instrument along the primary optical path.

10. The instrument of claim 9, wherein:
(a) the iris camera light path comprises incident light reflected from the subject's eye that passes through a Quarter Wave Plate QWP, a front lens L1, a first beamsplitter BS1, a second beamsplitter BS2, a third beamsplitter BS3, a TSA aperture of a telecentric stop, a tenth lens L10, and an eleventh lens L11, and then into the iris camera;
(b) the corneal topographer light path comprises light emitted by a plurality of conically-oriented holes in a topographer cone that illuminates the subject's eye, and then reflects off of the subject's eye, through the Quarter Wave Plate QWP, front lens L1, first beamsplitter BS1, second beamsplitter BS2, third beamsplitter BS3, telecentric stop aperture TSA, tenth lens L10, and eleventh lens L11, and then into the iris camera;
(c) the Helmholtz light path comprises Helmholtz light that is emitted from Helmholtz LED 12 and passes through a diffuser D12, then through a twelfth lens L12, and then through a Helmholtz Source plate HHS, which reflects off of the third beamsplitter BS3 through the second beamsplitter BS2, first beamsplitter BS1, front lens L1, and the Quarter Wave Plate QWP, then reflects off a cornea of the subject's eye, and then the Helmholtz light path reverses direction and goes back through the Quarter Wave Plate QWP, front lens L1, first beamsplitter BS1, second beamsplitter BS2, third beamsplitter BS3, telecentric stop aperture TSA, tenth lens L10, and eleventh lens L11, and finally on to the iris camera;
(d) the wavefront sensor light path comprises light reflected from the subject's eye passing through the Quarter Wave Plate QWP, front lens L1, first beamsplitter BS1, and then reflects off the second beamsplitter BS2, then through a second lens L2, then through a first polarizing beamsplitter PBS1, then reflects off of a second mirror M2, through a third lens L3, then through a Range Limiting Aperture RLA, then through a fourth lens L4, through a filter F1, and finally into a wavefront sensor WFS;
(e) the probe beam light path comprises probe beam light that is emitted by a super luminescent laser diode (SLD), then is carried by a fiber optic cable, then passes through a Fiber Optic Collimator (L5), then through second beamsplitter PBS2, reflects off a first partial beamsplitter PBS1, then through second lens L2, reflects off second beamsplitter BS2, then through first beamsplitter BS1, front lens L1, and the Quarter Wave Plate QWP, and then through a cornea of the subject's eye, thereby forming a spot of probe beam light on a retina of the subject's eye, wherein some of the probe beam light then scatters off the retina leaves the subject's eye and then goes back into the instrument along the wavefront sensor light path (d), where it finally illuminates the wavefront sensor;
(f) the video fixation target light path comprises video display light emitted from a micro video display that passes through a ninth lens L9, then an eighth lens L8, then through a pair of opposing Stoke's cell lenses SL1 and SL2, then reflected off a first mirror M1, then through a seventh lens L7, then through a sixth lens L6, and onto the first beamsplitter BS1 that redirects micro video display light through the front lens L1, then though the Quarter Wave Plate QWP, and finally into the subject's eye at an object plane; and
(g) the range-finder camera light path comprises light emitted by the subject's eye that passes through a thirteenth lens L13, a fourteenth lens L14, a fifteenth lens L15, and a sixteenth lens L16, and finally enters a first range-finder camera.

11. The instrument of claim 1, further comprising:
(1) a horizontal base support plate;
(2) a vertical support post attached to the horizontal base support plate;
(3) a primary optics plate attached to the vertical support post that holds a primary group of primary optical components;
(4) a secondary optics plate movably attached to the vertical support post, which holds a secondary group of secondary optical components;
(5) wherein the secondary optics plate is movable as a Badal stage in a vertical Y-direction along the primary optical path, relative to the primary group of primary optical components; and
(6) three orthogonal motors configured to move the vertical support post independently in X and/or Y and/or Z-directions;
wherein the three orthogonal motors are controllable by a joystick.

12. The instrument of claim 1, further comprising:
(1) a topographer cone comprising a central aperture and a plurality of holes disposed through the topographer cone, with a plurality of rear LED sources disposed circumferentially on a backside of the topographer cone that generates a uniform pattern of illuminated spots lit-up by rear LED light passing through the plurality of holes, which uniformly illuminates the subject's eye with a plurality of beamlets that are oriented at a range of off-axis angles of incidence;
(2) a first range-finder camera, and a second aperture in the topographer cone that passes light from the subject's eye through a plurality of first range-finder lenses and onto the first range-finder camera that is attached to the topographer cone;
(3) a pair of infrared LED sources disposed on a ring of the topographer cone located near the central aperture;
(4) a first visible LED light disposed on the ring of the topographer cone;
(5) a primary group of primary optical components, comprising:
(a1) a front lens, L1, disposed close to the central aperture of the topographer cone;
(b1) a first beamsplitter, BS1;
(c1) a second beamsplitter, BS2;
(d1) a third beamsplitter, BS3;
(e1) a telecentric stop, TSA;
(f1) a tenth lens, L10;
(g1) an eleventh lens, L11;
(h1) an iris imaging camera;
(i1) the first range-finder camera, which is attached to the topographer cone, that comprises a plurality of first range-finder lenses disposed in a tube that is attached to the topographer cone at one end and is attached to the first range-finder camera at an opposing end of the tube;
(j1) a twelfth LED, Helmholtz LED12;
(k1) a diffuser filter, D12;
(l1) a twelfth lens, L12; and
(m1) a Helmholtz source plate, HSS; and
(6) a secondary group of secondary optical components, comprising:
(a2) a second lens, L2;
(b2) a third lens, L3;
(c2) a fourth lens, L4;

(d2) a fiber optic collimator (FOC), L5;
(e2) a sixth lens, L6;
(f2) a seventh lens, L7;
(g2) an eighth lens L8;
(h2) a ninth lens, L9;
(i2) a first mirror, M1;
(j2) a second mirror, M2;
(k2) a first polarizing beamsplitter, PBS1;
(l2) a second polarizing beamsplitter, PBS2;
(m2) a range-limiting aperture, RLA;
(n2) a first filter, F1:
(o2) a Stoke's cell comprising a pair of independently-rotatable, cylindrical Stoke's cell lenses, SL1 and SL2, having equal and opposite power;
(p2) the video fixation target, which comprises a micro video display unit;
(q2) the wavefront sensor, WFS, comprising a lenslet array, LA, and a CCD camera; and
(r2) a fiber optic cable disposed in-between a secondary LED source, SLD1, and the fiber optic collimator, L5.

13. The instrument of claim 12,
wherein the Stoke's cell further comprises a first electromechanical control mechanism that is configured to rotate one or more of the pair of independently-rotatable, cylindrical Stoke's cell lenses; and
wherein the first electromechanical control mechanism comprises a belt-driven mechanism, a direct motor-driven mechanism, or a gear-driven mechanism.

14. The instrument of claim 12, further comprising a second polarizing beamsplitter, PBS2, that is located adjacent to the first polarizing beamsplitter, PBS1.

15. The instrument of claim 12, wherein the plurality of holes disposed through the topographer cone comprises a plurality of non-parallel holes that are conically-oriented at different angles all pointing towards the subject's eye.

16. The instrument of claim 12, further comprising a patient-controlled, motorized chin rest that holds a patient's head during optical measurements.

17. The instrument of claim 12, further comprising a second range-finder camera located on an opposite side of the topographer cone from the first range-finder camera.

18. The instrument of claim 12, further comprising a rectangular central aperture located in a center of the topographer cone.

19. The instrument of claim 18, further comprising a circular ring of LED lights surrounding the rectangular central aperture of the topographer cone, wherein the circular ring of LED lights comprises:
(1) a first LED emitting visible light at a first wavelength;
(2) a second LED emitting visible light a second wavelength that is different than the first wavelength;
(3) a third LED light and a fourth LED light emitting infrared light at a third wavelength; and
(4) a fifth LED light and sixth LED light emitting infrared light at a fourth wavelength that is different than the third wavelength.

20. The instrument of claim 12, wherein the front lens L1 has a larger diameter than any other lenses that are used in the instrument.

21. The instrument of claim 12, further comprising a Quarter Wave Plate (QWP) located in-between the front lens L1 and the subject's eye, wherein the QWP generates polarized light.

22. The instrument of claim 1, further comprising a corneal topographer configured to dynamically measure at least one corneal topography of the subject's eye.

23. The instrument of claim 22, wherein the corneal topographer is multiplexed with the wavefront sensor.

24. The instrument of claim 1, further comprising an iris camera configured to dynamically image an iris of the subject's eye and associated structures in the subject's eye.

25. The instrument of claim 24, wherein the iris camera is multiplexed with the wavefront sensor.

26. The instrument of claim 1, further comprising a measurement optical path and a video fixation target optical path, wherein the measurement optical path is separate from the video fixation target optical path.

27. The instrument of claim 1, further comprising an optical coherence topographer configured to dynamically measure a corneal shape, a corneal thickness, one or more parameters of an anterior segment of the eye, a total eye length, and/or a shape of a sclera of the subject's eye.

28. The instrument of claim 6, further comprising:
(a) means for measuring an instrument-to-eye distance; and
(b) means for calculating a topography of a cornea.

29. The instrument of claim 1, further comprising:
(a) means for objectively determining an objective refraction of the subject's eye; and
(b) means for subjectively determining a subjective refraction of the subject's eye.

30. The instrument of claim 1, further comprising a processor operatively connected to the wavefront sensor; wherein the processor is configured to compute values for astigmatism and defocus compensation.

31. The instrument of claim 1, further comprising means for making corrections by an operator of a Z-axis position of the dynamically-adjustable video fixation target.

32. The instrument of claim 29, further comprising:
(a) first electromechanical controls for adjusting the second Z-axis axial position along the primary optical path of the movable electromechanical stage holding the dynamically-adjustable video fixation target;
(b) a pair of electromechanically-controlled, independently-rotatable, cylindrical lenses having equal and opposite power; and
(c) second electromechanical controls for adjusting a rotation of at least one of the pair of electromechanically-controlled independently-rotatable, cylindrical lenses;
wherein the first and second electromechanical controls are configured to be used to refine the subjective refraction of the subject's eye based on trial and error feedback from the subject when reading an eye chart displayed on the dynamically-adjustable video fixation target.

33. The instrument of claim 1, further comprising third electromechanical control means for controlling an accommodation of the subject's eye by adjusting the first Z-axis position of the dynamically-adjustable video fixation target.

34. The instrument of claim 33, further comprising one or more fourth electromechanical control means for dynamically adjusting focus, astigmatism, and astigmatic axis of the subject's eye.

35. The instrument of claim 8, wherein the computer is configured to maximize a spherical equivalent and a pupil size of the subject's eye from a temporal sequence of eye measurements.

36. The instrument of claim 1, further comprising means for measuring corneal curvatures ($k_1$, $k_2$, and $k_2$ axis), horizontal visual iris diameter, and refraction sphere, cylinder, and axis.

37. The instrument of claim 1, further comprising operator-controlled electromechanical adjustment means for controlling astigmatism and defocus of the subject's eye, for subjectively making subjective refraction measurements of the subject's eye.

38. An instrument for dynamically measuring one or more optical parameters of a subject's eye, the instrument comprising:
- (a) a primary optical path, pointing towards the subject's eye, having a Z-axis that is coincident with the primary optical path;
- (b) a dynamically-adjustable video fixation target, aligned along the primary optical path and having a first Z-axis position, which is configured to compensate for astigmatism and defocus of the subject's eye;
- (c) a wavefront sensor, aligned along the primary optical path, which is configured to dynamically measure wavefront aberrations of the subject's eye;
- (d) a movable Badal stage, which is movable along the primary optical path; and
- (e) a movable electromechanical stage, which is mounted to the movable Badal stage, having a second Z-axis position;
- (f) a pair of independently-rotatable, cylindrical lenses aligned along the primary optical path, which have equal and opposite power; and
- (g) an electromechanical adjustment means for independently rotating at least one of the pair of independently-rotatable, cylindrical lenses;

wherein the wavefront sensor is attached to the movable Badal stage;

wherein the dynamically-adjustable video fixation target is moveably attached to the movable electromechanical stage; and wherein the movable electromechanical stage is configured to move the dynamically-adjustable video fixation target along the primary optical path independently from any motion of the movable Badal stage along the primary optical path.

* * * * *